US011160650B2

(12) United States Patent
Ma

(10) Patent No.: US 11,160,650 B2
(45) Date of Patent: Nov. 2, 2021

(54) OCULAR SYSTEMS, DEVICES, AND METHODS

(71) Applicant: Joseph J. K. Ma, North York (CA)

(72) Inventor: Joseph J. K. Ma, North York (CA)

(73) Assignee: Joseph J. K. Ma, North York (CA)

( * ) Notice: Subject to any disclaimer, the term of this patent is extended or adjusted under 35 U.S.C. 154(b) by 0 days.

(21) Appl. No.: 17/196,241

(22) Filed: Mar. 9, 2021

(65) Prior Publication Data

US 2021/0220119 A1 Jul. 22, 2021

Related U.S. Application Data

(63) Continuation of application No. 17/032,950, filed on Sep. 25, 2020, now Pat. No. 10,973,625, which is a continuation of application No. PCT/CA2019/051719, filed on Nov. 29, 2019.

(60) Provisional application No. 62/773,666, filed on Nov. 30, 2018, provisional application No. 62/773,827, (Continued)

(51) Int. Cl.
A61F 2/16 (2006.01)
G02F 1/01 (2006.01)
G02F 1/23 (2006.01)
G02F 1/29 (2006.01)
(Continued)

(52) U.S. Cl.
CPC ............ *A61F 2/1635* (2013.01); *A61F 2/164* (2015.04); *G02F 1/0121* (2013.01); *G02F 1/23* (2013.01); *G02F 1/29* (2013.01); *A61F 2/1624* (2013.01); *A61F 2/1659* (2013.01); *A61F 2002/1683* (2013.01); *A61F 2002/1696* (2015.04); *A61F 2002/482* (2013.01); *A61F 2250/0002* (2013.01); *A61F 2250/0026* (2013.01); *A61F 2250/0068* (2013.01); *G02B 26/005* (2013.01); *G02F 2203/055* (2013.01)

(58) Field of Classification Search
CPC .... A61F 2/1635; A61F 2/1613; A61F 2/1659; A61F 2002/1696; A61F 2250/0026; A61F 2/1624; G02F 2203/055; G02B 26/005
See application file for complete search history.

(56) References Cited

U.S. PATENT DOCUMENTS

| 5,880,872 A | 3/1999 | Udaka |
| 5,903,382 A | 5/1999 | Tench et al. |
| 6,067,184 A | 5/2000 | Bonhote et al. |

(Continued)

FOREIGN PATENT DOCUMENTS

| CA | 2611851 C | 12/2014 |
| EP | 1851585 B1 | 6/2018 |

(Continued)

OTHER PUBLICATIONS

International Search Report and Written Opinion of corresponding International Application No. PCT/CA2019/051719 dated Apr. 3, 2020, 20 pages.

(Continued)

*Primary Examiner* — Javier G Blanco
(74) *Attorney, Agent, or Firm* — Bereskin & Parr LLP/S.E.N.C.R.L., S.R.L.

(57) ABSTRACT

Various embodiments are described herein for an ocular device implantable in a user's eye and which has an adjustable optical element for varying one or more optical properties for the eye such as, but not limited to, providing a dynamically adjustable aperture stop to control the amount of incoming light, filtering incoming light, polarizing incoming light, and/or varying a depth of field for the eye.

20 Claims, 19 Drawing Sheets

Related U.S. Application Data filed on Nov. 30, 2018, provisional application No. 62/849,308, filed on May 17, 2019.

(51) Int. Cl.
*A61F 2/48* (2006.01)
*G02B 26/00* (2006.01)

(56) References Cited

U.S. PATENT DOCUMENTS

| | | | |
|---|---|---|---|
| 7,888,626 | B2 | 2/2011 | Slinger et al. |
| 8,446,341 | B2 | 5/2013 | Amirparviz et al. |
| 8,553,222 | B2 | 10/2013 | Brady et al. |
| 9,759,984 | B1 | 9/2017 | Xu et al. |
| 9,851,613 | B2 | 12/2017 | Noble et al. |
| 2009/0097096 | A1 | 4/2009 | Noh et al. |
| 2013/0073038 | A1 | 3/2013 | Azar |
| 2014/0268029 | A1 | 9/2014 | Pugh et al. |
| 2015/0109652 | A1 | 4/2015 | Milliron et al. |

FOREIGN PATENT DOCUMENTS

| | | |
|---|---|---|
| WO | 0174444 A1 | 10/2001 |
| WO | 2005033782 A2 | 4/2005 |
| WO | 2009117506 A2 | 9/2009 |
| WO | 2016160759 A1 | 10/2016 |

OTHER PUBLICATIONS

Anat Levin et al., Image and Depth from a Conventional Camera with a Coded Aperture, ACM Transactions on Graphics, vol. 26, No. 3, Article 70, Jul. 2007, pp. 70-1 to 70-9.

Ashok Veeraraghavan et al., Dappled Photography: Mask Enhanced Cameras for Heterodyned Light Fields and Coded Aperture Refocusing, ACM Transactions on Graphics, vol. 26, No. 3, Jul. 29, 2007, 12 pages.

Hernandez et al., Bistable Black Electrochromic Windows Based on the Reversible Metal Electrodeposition of Bi and Cu, ACS Energy Letter, 2018, vol. 3, pp. 104-111.

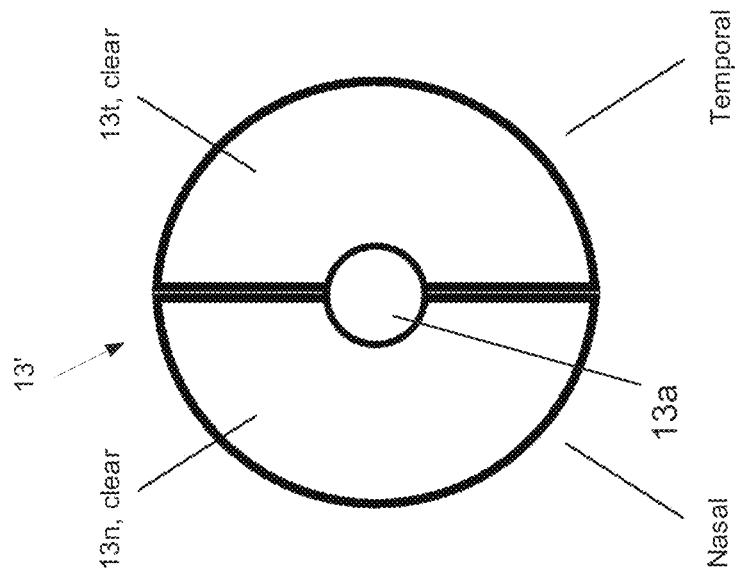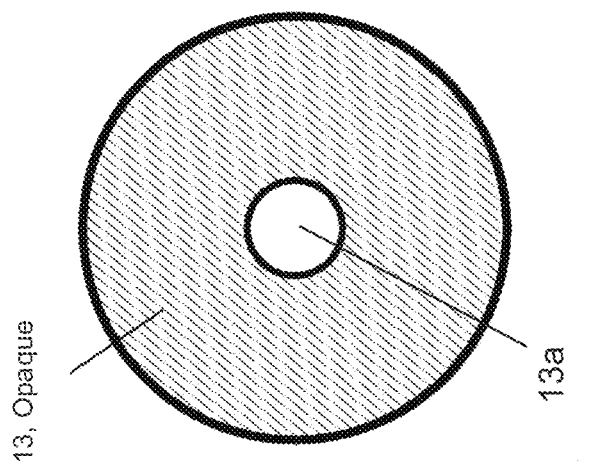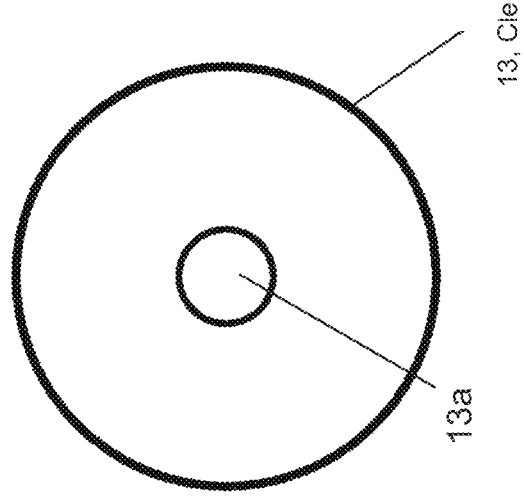

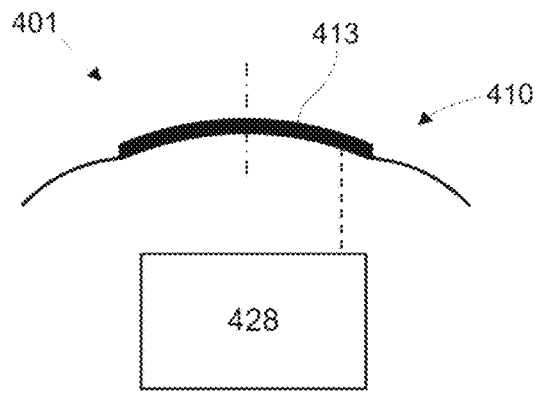
FIG. 12
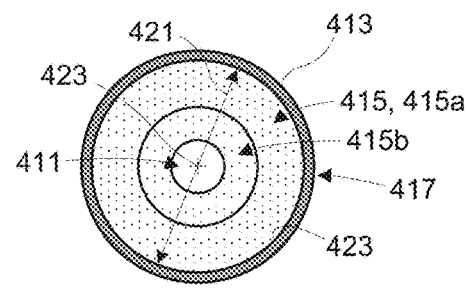
FIG. 13A
FIG. 13B
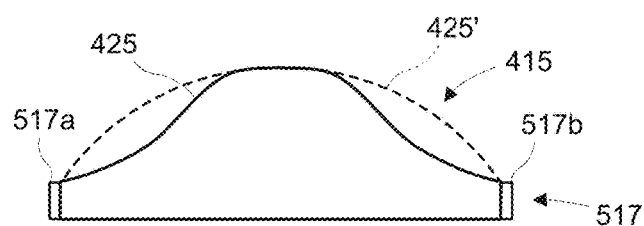
FIG. 14A
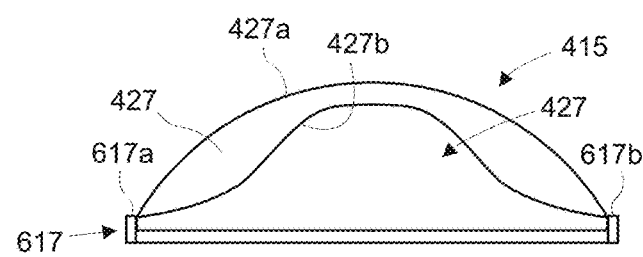
FIG. 15
FIG. 14B
FIG. 14C

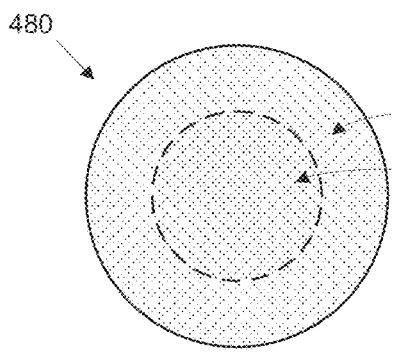 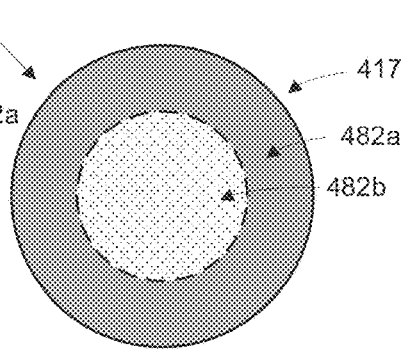
FIG. 16A    FIG. 16B
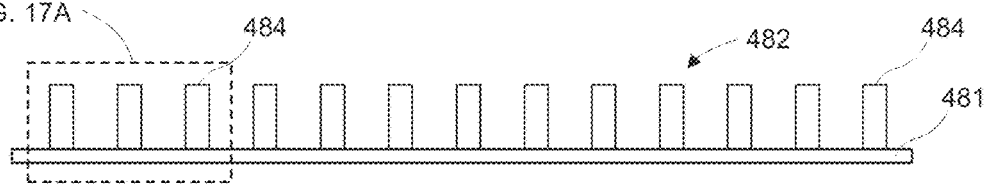
FIG. 17
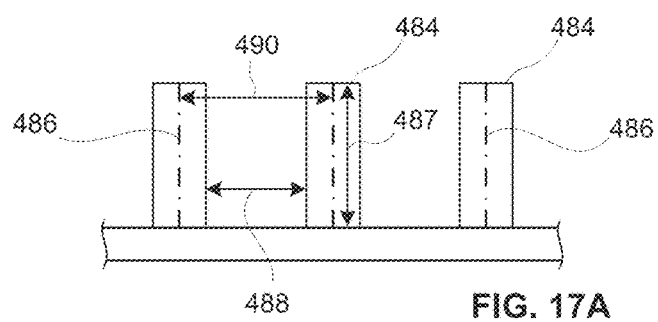 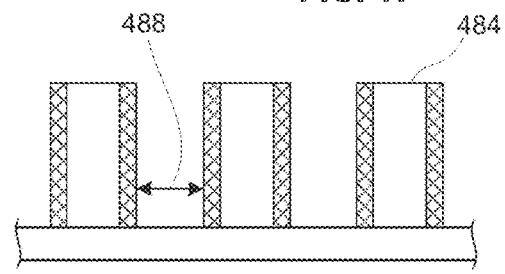
FIG. 17A    FIG. 17B
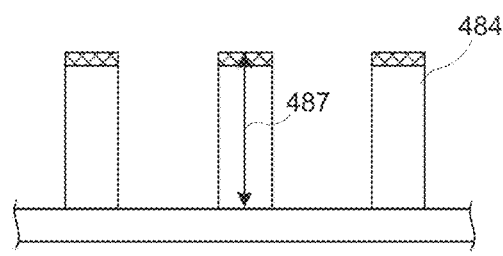 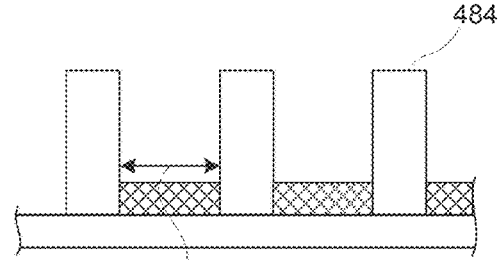
FIG. 17C    FIG. 17D
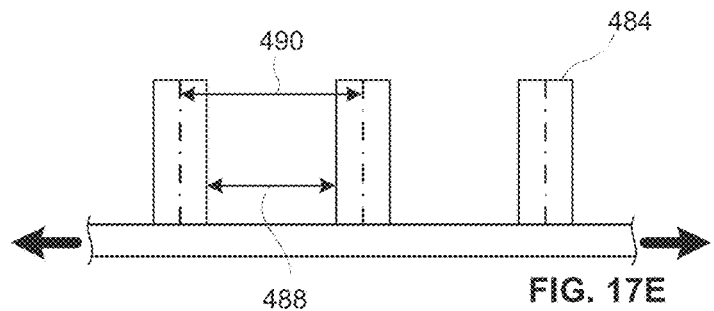
FIG. 17E

OCULAR SYSTEMS, DEVICES, AND METHODS

CROSS-REFERENCE TO RELATED APPLICATIONS

This application is a continuation of U.S. patent application Ser. No. 17/032,950 filed Sep. 25, 2020, which is a continuation of International Application No. PCT/CA2019/051719 filed Nov. 29, 2019, which claims the benefit of U.S. Provisional Application No. 62/773,666 filed Nov. 30, 2018; U.S. Provisional Application No. 62/773,827 filed Nov. 30, 2018; and U.S. Provisional Application No. 62/849,308 filed May 17, 2019, each of which is incorporated herein by reference in its entirety. The international Patent Cooperation Treaty application entitled OPTIC SYSTEMS, DEVICES, AND METHODS, filed on Nov. 29, 2019, listing Inventor JOSEPH J. K. MA, and having International Application No. PCT/CA2019/051718, is hereby incorporated herein by reference in its entirety.

FIELD

Various embodiments are described herein that generally relate to ocular systems, devices, and methods.

INTRODUCTION

The iris is an annular structure that is located in the anterior chamber of the eye behind the cornea and in front of the lens in the eye. The iris has an adjustable aperture that is called the pupil. The iris comprises of connective tissue and muscle fibers that allow it to change its size and control the size of the pupil by expanding the pupil (i.e. dilating) or contracting the pupil. The iris therefore controls the amount of light that enters the eye, which is important as this affects the perception of vision, glare and depth of field, similar to the aperture of a camera.

The amount of light, accommodation and physiologic responses to emotional stimuli can also affect the size of the pupil by innervating either or both of the sympathetic nervous system (causing pupil dilation) and the parasympathetic nervous system (resulting in pupil constriction) to varying degrees.

The iris also defines the primary perceived eye color for a person or an animal. For example, the iris can have a variety of colors including, but not limited to, brown, blue, green, grey and hazel. These colors are created from a combination of structural colour (the microstructure of the stroma of the iris results in a bluish colour in the absence of pigment) and available pigment. For example, significant amounts of melanin in the iris epithelium results in a brown color. The distribution of colour in the iris can give rise to the perception of a changing colour of the iris, especially in what is commonly referred to as a hazel iris colour. For example, in a hazel coloured eye, if the pigment is primarily confined to a circular area circumscribing the pupil, an iris may appear darker and more brownish when the pupil is dilated and more bluish or greenish when the pupil is constricted and the mid-peripheral bluish iris stroma (areas without pigment) is stretched.

Some people do not have either a portion, a section or all of the iris, either by birth (referred to as congenital) or acquired (usually from either trauma or surgery). Trauma from blunt force or injury including that from explosive devices, air-bags and firecrackers can cause the loss of at least part of the entire visible iris. The absence of a part or all of the iris is both cosmetically obvious and can prevent one from effectively controlling the amount of light that enters their eye, which can lead to severe glare and difficulty with vision. In addition, some people with an intact iris cannot significantly dilate or constrict their pupils either due to ischemia, neuropathy, injury of the iris sphincter, atrophy of the required musculature for dilation from use of medications (such as alpha blockers e.g. Tamsulosin), surgical trauma, or other reasons.

Currently, methods of replacing the iris rely either on placing an opaque disk or a section of an optically opaque disk over the area of the iris defect. This optically opaque disk can be composed of either a hard (e.g. PMMA (Poly (methyl methacrylate)) or soft (e.g. silicone) material. Sometimes this opaque disk is painted on its external surface to match the appearance of the contralateral eye. However, these disks are not optically dynamic, and thus cannot perform the aperture function of a normal iris. They cannot respond to either ambient light or innervation. In addition, these disks limit the field of view of the internal structures of the eye, which can hinder medical examinations and medical treatments such as either the examination or treatment of the peripheral retina. Functionally, these opaque disks can also affect either or both the sensitivity and visual field results of a subjectively administered visual field test.

An alternative technique to replace the iris includes the use of a pupillary cerclage with a purse string suture that can help to decrease the size of the pupil if enough of the iris is intact. However, since all or part of the pupillary sphincter muscle is often damaged in these instances, and due to the restricted diameter of the purse string as it is tied, the pupil is often is also static in these types of iris repairs.

Cosmetically changing the colour of iris has also been sought out as a cosmetic procedure. Currently, this can be achieved by use of an annular disk similar to the disks described above for iris repair, which has the same limitations of being an immobile disk that cannot change the pupil size. There are also surgical methods, including the use of a laser designed to cause cells in the eye to phagocytize melanin and therefore change the colour of a darker (e.g. brown) iris to a blue iris without pigment. This process however is not currently easily reversible, and would likely only be able to conceivably lighten, but not darken the colour of the iris.

SUMMARY

According to some aspects, an intraocular prosthesis system includes (a) an optical device implantable in an eye, the optical device having at least one adjustable optical element operable to vary a depth of field for the eye; and (b) a controller configured to control adjustment of the optical element for varying the depth of field.

In some examples, the system further includes one or more environment sensors for detecting environmental conditions and generating environment sensor signals indicative of the environmental conditions, and wherein the controller is configured to control adjustment of the optical element based at least on the environment sensor signals to provide a suitable depth of field for the environmental conditions.

In some examples, the environmental conditions comprise a distance to one or more objects of interest. In some examples, the one or more sensors include a rangefinder operable to estimate the distance to the one or more objects of interest and generate rangefinder signals indicative of the distance, and wherein the controller is configured to control adjustment of the optical element based on at least the rangefinder signals to provide the suitable depth of field.

In some examples, the environmental conditions comprise environmental illumination. In some examples, the one or more sensors include at least one illumination sensor operable to measure the environmental illumination and generate illumination signals indicative of the environmental illumination, and wherein the controller is configured to control adjustment of the optical element based on at least the illumination signals to provide the suitable depth of field.

In some examples, the system further includes one or more intraocular sensors for detecting intraocular conditions and generating intraocular sensor signals indicative of the intraocular conditions, and the controller is configured to control adjustment of the optical element based on the intraocular sensor signals to provide a suitable depth of field for the intraocular conditions. In some examples, the intraocular conditions comprise electrical activity in the eye corresponding to, in some examples, contraction of the ciliary body in the eye.

In some examples, the optical element comprises at least one optical portion and an occlusion mechanism operable by the controller to transition the optical portion between a transparent state in which the optical portion is generally transparent for providing a first depth of field for the eye and an occluded state in which the optical portion is at least partially occluded relative to the transparent state for providing a second depth of field for the eye, the second depth of field different from the first depth of field.

In some examples, the occlusion mechanism is configured to transition the optical portion through at least one of electrochromism and electrodeposition.

In some examples, the at least one optical portion comprises at least one of: (i) one or more diffractive zones and (ii) one or more refractive zones.

In some examples, the at least one optical portion comprises an array of meta-lens wave-guide structures.

In some examples, the occlusion mechanism comprises an adjustable aperture stop operable by the controller to adjust an aperture size for the eye for varying the depth of field. In some examples, the at least one optical element comprises a plurality of the optical portions arranged concentrically, and the occlusion mechanism is configured to reversibly occlude each optical portion independently for adjusting the aperture size.

In some examples, the at least one optical element comprises at least one optical portion having an adjustable morphology, and a morphology adjustment mechanism operable by the controller to transition the optical portion between at least a first morphology for providing a first depth of field for the eye and a second morphology for providing a second depth of field for the eye, the second depth of field different from the first depth of field.

In some examples, the at least one optical portion comprises a lens surface adjustable between the first morphology and the second morphology.

In some examples, the first morphology corresponds to an aspheric shape, and the second morphology corresponds to a spheric shape relative to the aspheric shape.

In some examples, the at least one optical portion comprises one or more diffractive zones adjustable between the first morphology and the second morphology.

In some examples, the at least one optical portion comprises an array of meta-lens wave-guide structures adjustable between the first morphology and the second morphology.

In some examples, the at least one optical element comprises at least one optical portion having an adjustable refractive index and a refraction adjustment mechanism operable by the controller to adjust the refractive index for varying the depth of field.

In some examples, the at least one optical portion comprises a lens casing having an internal chamber containing nematic liquid crystal, and the refraction adjustment mechanism comprises one or more electrodes adjacent the chamber and operable by the controller to apply an electric field to the nematic liquid crystal for adjusting the refractive index to change the depth of field for the eye.

In some examples, the lens casing and the nematic liquid crystal have a common first refractive index corresponding to a first depth of field for the eye in absence of the electric field, and wherein the lens casing has the first refractive index and the nematic liquid crystal has a second refractive index different from the first refractive index when the electric field is applied to provide a second depth of field for the eye.

In some examples, the lens casing includes an exterior lens surface having a first lens shape, and an interior lens surface defining at least a portion of the internal chamber and having a second lens shape different from the first lens shape.

In some examples, one of the first lens shape and the second lens shape is spheric relative to the other one of the first lens shape and the second lens shape, and the other one of the first lens shape and the second lens shape is aspheric relative to the one of the first lens shape and the second lens shape.

In some examples, the optic element comprises an adjustable meta-lens assembly operable to vary the depth of field for the eye, and the controller is configured to control adjustment of the meta-lens assembly for varying the depth of field.

In some examples, the meta-lens assembly includes at least one array of meta-lens wave-guide structures, and a wave-guide adjustment mechanism for adjusting properties of the wave-guide structures to vary the depth of field.

In some examples, the wave-guide adjustment mechanism comprises an occlusion mechanism configured to reversibly occlude at least a portion of the at least one array for varying the depth of field.

In some examples, the occlusion mechanism is configured to reversibly occlude the at least a portion of the array through at least one of electrodeposition and electrochromism.

In some examples, the at least one array comprises at least one first set of wave-guide structures and at least one second set of wave-guide structures, and wherein the occlusion mechanism is configured to reversibly occlude at least one of the first set and the second set of wave-guide structures while the other one of the first set and the second set of wave-guide structures remains unoccluded to vary the depth of field. In some examples, the first set is configured for near vision focus, and the second set is configured for distance vision focus. In some examples, the occlusion mechanism is configured to reversibly occlude the first set of wave-guide structures while the second set remains unoccluded to facilitate distance vision focus. In some examples, each of the first set and the second set is concentric with an axis of the meta-lens assembly, and the second set is radially inward of the first set.

In some examples, each wave-guide structure projects from a substrate along a central axis and has a cross-sectional area normal to the axis, and wherein the cross-sectional area is adjustable for varying the depth of field. In some examples, the wave-guide structures comprise electrodeposition sites, the electrodeposition sites platable with ions from an electrolyte medium to increase the cross-sectional area and strippable of the ions to reduce the cross-sectional area.

In some examples, adjacent wave-guide structures have a wave-guide gap therebetween through which electromagnetic radiation is guided, and a size of the wave-guide gap between at least some of the adjacent wave-guide structures is adjustable for varying the depth of field.

In some examples, the wave-guide adjustment mechanism comprises a morphology adjustment mechanism configured to adjust a morphology of the at least one array for varying the depth of field.

In some examples, adjacent wave-guide structures have a center-to-center distance, and the center-to-center distance of at least some of the wave-guide structures is adjustable by the morphology adjustment mechanism for varying the depth of field.

In some examples, the meta-lens assembly comprises a deformable substrate from which the wave-guide structures project, and the morphology adjustment mechanism is configured to deform at least a portion of the substrate for adjusting the center-to-center distance.

According to some aspects, an optical platform system includes (a) a substrate implantable in an eye, the substrate having an aperture stop defining an aperture for the eye; (b) at least one sensor coupled to the substrate for monitoring one or more properties of the eye; (c) an upgrade interface on the substrate for installation of an optical element over the aperture stop; and (d) a controller for controlling operation of the platform system.

In some examples, the upgrade interface comprises a recessed area in the substrate, the recessed area shaped to receive the optical element.

In some examples, the upgrade interface comprises at least one connector configured to connect the optical element when received in the recess for communication between the optical element and platform components.

In some examples, wherein the upgrade interface comprises actuators for moving the optical element into alignment with a specific visual axis.

In some examples, the system further includes at least one coil coupled to the substrate for receiving wireless signals, the coil in communication with the controller.

In some examples, the substrate is flexible to facilitate implantation thereof.

In some examples, the at least one sensor is configured for sensing electrical activity in the eye.

According to some aspects, a method of measuring an analyte in aqueous humour of an eye includes: (a) transmitting electromagnetic radiation through the aqueous humour and onto a prosthetic iris device implanted in the eye posterior of the aqueous humour; (b) detecting electromagnetic radiation reflected from the aqueous humour and the iris device; and (c) determining an analyte value for the analyte based at least in part on the electromagnetic radiation detected in step (b).

In some examples, step (c) includes determining one or more apparent optical properties of the aqueous humor and iris device based on the electromagnetic radiation detected in step (b), and comparing the apparent optical properties to one or more corresponding baseline optical properties for the aqueous humour and iris device.

In some examples, step (c) includes generating at least one image of the aqueous humour and iris device based on the electromagnetic radiation detected in step (b), and identifying a deviation in one or more image properties between the at least one image and one or more baseline images for the aqueous humour and iris device, the deviation corresponding to the analyte value. In some examples, the electromagnetic radiation comprises laser light, and the analyte level is determined at least in part through laser spectroscopy. In some examples, the electromagnetic radiation comprises polarized light, and the analyte value is determined based at least in part through polarimetry.

In some examples, during step (b), the iris device is in a first state, and the method further comprises (d) transitioning the iris device to a second state different from the first state, and (e) detecting electromagnetic radiation reflected from the aqueous humour and the iris device in the second state. In some examples, step (c) includes determining the analyte value based further on the electromagnetic radiation detected in step (e).

In some examples, the first state corresponds to a first value of an optical property of the iris device and the second state corresponds to a second value of the optical property, the second value different from the first value. In some examples, the optical property comprises reflectance.

In some examples, the method further includes applying a charge voltage to transition the iris device from the first state to the second state. In some examples, the charge voltage is applied between a working electrode and a counter electrode of the iris device. In some examples, transitioning the iris device from the first state to the second state comprises at least one of: nanoplating the working electrode with ions from an electrolyte in the iris device, and stripping the working electrode of the ions. In some examples, the charge voltage is applied according to a predetermined polarity, magnitude, and duration.

In some examples, the analyte value corresponds to blood glucose level.

According to some aspects, a dynamic light modulating ocular device with at least one changing light property includes: an optically adjustable element, the adjustable element having at least one sub-component that dynamically modulates light transmission for at least a portion of a spectral range of incoming electromagnetic energy; and a controller that is communicatively coupled to the optically adjustable element to control the modulation of the electromagnetic energy by the optically adjustable element.

In some examples, the device further includes a transparent, biocompatible coating sealing at least the adjustable element.

In some examples, the at least one sub-component is adapted to dynamically modulate light transmission by implementing one of a chemical, electrochemical, mechanical, or electromechanical process.

In some examples, the at least one sub-component comprises one or more of at least one reversible nanoplating electrode, electrochromic material, suspended particles, nanocrystals, and MEMS sheets of metal having a micrometer scale that bend and stretch when receiving an applied voltage.

In some examples, the at least one sub-component is adapted to dynamically modulate light transmission by changing at least one of reflectance, absorbance, and polarization of the incoming electromagnetic energy.

In some examples, the device is designed to be implanted intraocularly or placed outside of a user's eye.

In some examples, the device includes at least one tracking marker that reflects or emits electromagnetic energy, including visible light and radiofrequency energy, to allow for tracking of the visual axis of the eye in which the device is implanted.

In some examples, the device further comprises at least one intraocular lens located at a front, rear, or central portion of the device. In some examples, the at least one intraocular lens comprises a stack of monofocal or multifocal intraocular lenses.

In some examples, the coating comprises a channel to allow for fluid ingress or fluid egress through the device to prevent build-up of fluid and increased pressure when the device is located inside an eye.

In some examples, the coating is water impermeable and transparent. In at least one embodiment, the coating has a hydrophobic external surface.

In some examples, the device further comprises one or more light sources controllable by the controller to project light signals directly onto a retina of the eye in which the device is implanted. In some examples, the light source comprises at least one of an OLED, an LED, and a laser light source. In some examples, the light signals are for communicating information to a person having the eye in which the device is implanted.

In some examples, the device further comprises at least one electrode within the coating and disposed adjacent to the at least one sub-component to control an area thereof that is used to modulate the incoming electromagnetic energy.

In some examples, the device further comprises a first electrode and a second electrode, and at least one charge storage element within the coating, the first and second electrodes coupled to the at least one charge storage element for receiving different amounts of charge during use to provide different voltages to the at least one subcomponent of the optically adjustable element for changing an adjustable light transmission property of the device during operation.

In some examples, the optically adjustable element has at least two sections that are separately controllable by the controller to modulate the incoming electromagnetic energy in different ways to communicate information to a person having an eye in which the device is implanted.

In some examples, the device further comprises a transmitter communicatively coupled to the controller to control at least one portion of the optically adjustable element wirelessly. In some examples, the at least one portion of the optically adjustable element is controlled wirelessly to communicate information to a person having an eye in which the device is implanted.

In some examples, the optically adjustable element is controlled wirelessly to decrease or increase transmission of electromagnetic energy through the device to, for example, communicate with a person having an eye in which the device is implanted.

In some examples, the optically adjustable element comprises multiple elements that are individually controllable to modulate incoming electromagnetic energy for communicating information to a person having an eye in which the device is implanted.

In some examples, the information includes at least one of directional information and coded information.

In some examples, the device further comprises one or more lenses arranged to one another to manipulate a focus of incoming light.

In some examples, the device further comprises one or more micro electromechanical actuators that are coupled to the one or more lenses to adjust at least one of an angle and location of the lenses. In some examples, the device further comprises at least one layer of micro piezo-electric actuators disposed on the outer surface of the coating and configured to at least one of sense and move the device within its implanted space. In some examples, the implanted space includes a lenticular capsular bag.

In some examples, the device further comprises an antenna that is disposed on or within the coating for at least one of receiving a wireless signal from an external device and sending a wireless signal to the external device, the wireless signal for initiating one or more operations associated with the device. The operations comprise at least one of controlling the device, providing energy for the device, transmitting data to the external device, and transmitting data to the ocular device. In some examples, the external device comprises a mobile device. The mobile device can be, for example, a smart phone, an ear bud, and/or another device that can be transported (e.g. held or worn) by a user.

In some examples, the controller is configured to determine whether one or more security conditions are satisfied prior to performing an operation based on an operation request received from the external device, and to perform the operation only if the security conditions are satisfied. In some examples, the one or more security conditions are based on at least one of proximity of the external device to the ocular device and signals emitted from the external device.

In some examples, the optically adjustable element is controllable to change a position of a central optical aperture of the device to optimize a path of incoming light.

In some examples, the device further comprises a rangefinder adapted to provide a signal to control the optically adjustable element to increase a size of an aperture when the distance of a detected object is larger than a distance threshold or to decrease the aperture of the device when the distance of the detected object is smaller than the distance threshold.

According to some aspects, a dynamic light modulating device with at least one adjustable optical property comprises: an optically adjustable element adapted to dynamically modulate incoming electromagnetic energy through nanoplating, the optically adjustable element including at least one stack having: at least one working electrode having a substrate and a plurality of deposition sites that are reversibly nanoplatable through electrodeposition to adjust the optical property; at least one counter electrode; a non-conducting spacer separating the at least one working electrode and the at least one counter electrode; an electrolyte medium between the at least one working electrode and the at least one counter electrode to facilitate the electrodeposition; and an inert coating sealing the device. The working electrodes (or portions thereof) are generally transparent when not plated.

In some examples, the substrate is made of inert material and is structured for providing the deposition sites.

In some examples, the substrate has a surface that faces the electrolyte medium and the plurality of deposition sites are formed on the surface of the substrate.

In some examples, the device is flexible to facilitate implantation into the eye.

In some examples, the device further comprises at least one coil that functions as an antenna for receiving at least one of communication signals, power, and voltage to activate the device wirelessly via induction.

In some examples, the device further comprises an integrated circuit configured to generate and provide control signals to at least one of sensors an actuators on the device, and control power usage, signal reception, and signal transmission for the device.

In some examples, the deposition sites are formed of metallic nanowires. In some examples, the metallic nanowires are made of a noble metal. In some examples the noble metal comprises platinum.

In some examples, the deposition sites are formed on the surface of the at least one transparent electrode and comprise nanowires made of silver or another conductive metal, with platinum or other noble metal coating or seeding.

In some examples, the deposition sites comprise carbon. In some examples the carbon includes at least one of graphene and carbon nano-tubes with a platinum or other noble metal coating or seeding.

In some examples, the deposition sites comprise Tin Oxide with platinum or other noble metal coating or seeding. In some examples, the Tin Oxide comprises at least one of Indium Tin Oxide and Fluorine Tin Oxide.

In some examples, the electrolyte comprises metal ions that are platable onto at least some deposition sites on the at least one transparent electrode during use in a reversible fashion when a charge voltage applied across the at least one working electrode and the counter electrode.

In some examples, the metal ions comprise at least one of gold, copper, silver, and a non-ferromagnetic metal.

In some examples, the counter electrode is made of at least one of gold, silver, copper, and a non-ferromagnetic metal.

In some examples, the device further includes a transparent backplate within the coating, the transparent backplate provided by an additional optical element arranged on a side of the device opposite a first one of the at least one working electrode, wherein the counter electrode is positioned intermediate the first one of the at least one working electrode and the backplate. In some examples, the first one of the at least one working electrode, the backplate, and the spacer at least partially enclose a chamber holding the electrolyte medium.

In some examples, the backplate comprises at least one of clear transparent film and a lens surface.

In some examples, the least one working electrode has a plurality of patterns of deposition sites that are electrically isolated and controllable by separate circuits to achieve different nanoplating patterns. In some examples, the nano-plating patterns comprises at least one of (1) multiple concentric rings for variable pupil size and (2) nasal and temporal portions for directional augmented reality.

In some examples, the at least one working electrode comprises a first electrode and a second electrode spaced apart from the first electrode.

In some examples, the first electrode has a first plurality of deposition sites to provide a first pattern when the first electrode is plated and the second electrode has a second plurality of deposition sites to provide a second pattern different from the first pattern when the second transparent electrode is plated.

In some examples, the first and second patterns provide the device with different sized apertures when one of the first or second electrodes receives plating.

In some examples, when the first and second electrodes do not receive plating, a portion of the device covered by the first and second electrodes is transparent.

In some examples, when the first and second electrodes both receive plating at the same time a portion of the device covered by the first and second transparent electrodes is opaque.

In some examples, the first and second aperture patterns each apply a different modulation to incoming electromagnetic energy, wherein when only the first electrode receives plating the incoming electromagnetic energy is modulated to have a first type of polarization and when only the second electrode receives plating the incoming electromagnetic energy is modulated to have a second type of polarization.

In some examples, the device comprises one or more transparent porous electrodes disposed within the electrolyte medium, wherein a given porous electrode is electrically isolated from other electrodes in the device and is selectively platable with ions from the electrolyte medium during use to reversibly modify a transparency of the porous electrode when a charge voltage is applied thereto.

In some examples, reversible plating of ions from the electrolyte medium on the porous electrode is controlled by applying charge voltages to the electrode either independently or together with the at least one working electrode or an additional porous electrode.

In some examples, the porous electrodes have a different plurality of deposition sites to provide the device with at least one of different aperture patterns, different aperture sizes, different modulations of incoming electromagnetic energy, and changes in speed of aperture formation when the additional porous electrodes are nano-plated alone or in combination with other electrodes of the device.

In some examples, the device comprises a reservoir of additional electrolyte medium, the additional electrolyte medium in fluid communication with each electrode to provide additional ions to facilitate faster plating. In some examples, the reservoir of additional electrolyte medium is located outside of a visual axis of the adjustable element.

In some examples, the at least one working electrode has a plurality of deposition sites arranged so that the plating occurs when a charge voltage is applied to the at least one working electrode to form at least one plated pattern. In some examples, the plated pattern provides an aperture having an adjustable shape or size.

In some examples, the device further comprises multiple stacks positioned on top of one another where each stack comprises different working electrodes with respective patterns of deposition sites that are different in each stack to provide different apertures, patterns, or combinations thereof, when the different working electrodes receive charge voltages either independently or together to undergo nanoplating.

In some examples, the electrodeposition sites are arranged to provide microgates when plated, the microgates for adjusting the transparency and reflectivity to specific electromagnetic wavelengths.

In some examples, a plurality of deposition sites have locations, shapes, and periodicities that are predefined to, when plated, reflect a specific portion of the spectral wavelengths of incoming electromagnetic energy, while transmitting and/or absorbing other spectral wavelengths of the incoming electromagnetic energy.

In some examples, the locations, shapes, and periodicities of the deposition sites are arranged to provide a plurality of branches that create a black appearance for at least one portion of the at least one working electrode when plating occurs on the at least one working electrode by reflecting the incoming electromagnetic energy internally and absorbing the incoming electromagnetic energy.

In some examples, the locations of the deposition sites are shaped and spaced to intentionally reflect wavelengths corresponding to a certain visible color of the incoming light while absorbing or intentionally transmitting wavelengths of the other visible colors of the incoming light to allow the device to have a color that is the same as a targeted reflected visible color to allow the user to view wavelengths corresponding to the transmitted wavelengths.

In some examples, the coating is water impermeable and transparent. In at least one embodiment, the coating has a hydrophobic external surface.

According to some aspects, an intraocular optical platform system for powering and controlling an intraocular device wirelessly, the intraocular device being defined according to any one of the embodiments described in accordance with the teachings herein, wherein the platform system comprises at least one coil for receiving wireless signals for communication or power purposes; and a controller that is coupled to the at least one coil and is configured for generating control signals based on the received wireless signals.

In some examples, the platform system further includes at least one energy storage element for storing energy to provide power for the platform system.

In some examples, the at least one energy storage element comprises at least one of a capacitor, a supercapacitor, a battery, an RF energy harvester, and a metamaterial RF energy harvester.

In some examples, the platform system comprises at least one sensor and the controller is coupled with the at least one sensor and the at least one coil to receive data measured by the at least one sensor and transmit the measured data to an external device.

In some examples, the at least one sensor comprises at least one biomarker sensor for monitoring a corresponding biomarker level in an intraocular fluid space of an eye when the platform is implanted in the eye, wherein the at least one biomarker sensor comprises at least one of a glucose sensor, a protein sensor, an enzyme sensor, a cytokinin sensor, a pressure sensor, a spectrometer, and a motion sensor.

In some examples, the at least one sensor comprises a pressure sensor that is configured to monitor the pressure in a portion of the eye in which the platform is located.

In some examples, the at least one sensor comprises a sensor for sensing, either directly or indirectly, electrical activity corresponding to an intentional innervation or contraction of a ciliary muscle by measuring changes in electrical charge at the position of the sensor, or measuring changes in mechanical force at the position of the sensor.

In some examples, the platform system further comprises a memory chip that is coupled to the controller and configured to store the measured data from the at least one sensor with a time stamp to reduce a frequency of communication between the platform and an external device.

In some examples, the platform system further comprises at least one photovoltaic element or at least one photodiode adapted to supply power to the device.

In some examples, the platform system further comprises self-centering elements that are disposed at peripheral edges of the platform and are configured to center the platform system when implanted in an eye.

In some examples, the self-centering elements include sensors to measure ciliary body contraction or electrical activity at the location of the sensors of the self-centering elements in the eye.

In some examples, the platform system further comprises piezo-electric devices that generate energy when the piezo-electric devices are activated either directly or indirectly by the contraction of the ciliary body muscle and the generated energy for sensing the presence of contractions and/or supply voltage to the platform.

In some examples, the platform system further comprises an upgrade interface module having a port with connectors for connection with upgraded components for upgrading the platform system.

In some examples, the platform system further comprises a communication chip that is configured to relay information from the controller to an external device.

In some examples, the communication chip comprises a Bluetooth low energy chip or an RFID.

In some examples, the device further comprises a plurality of micro-reservoirs of micro-dosed medication releasable to provide the medication to the eye in which the platform system is implanted when a wireless signal is sent to the controller or a condition requiring the medication is sensed.

According to some aspects, a method of measuring accommodation convergence in a person's eye comprises: implanting a device with electromagnetic markers in or on the eye; tracking the electromagnetic markers in 3-dimension space and time, using an observing device having a sensor, where the electromagnetic markers are tracked relative to each other and to a standard position of the observing device to generate a tracked pattern; and determining that accommodation convergence is occurring when the relative positions, torsional movements and 3-dimensional movements of the markers relative to each other over time in the tracked pattern are the same as a pre-defined pattern for the person where the pre-defined pattern is obtained when the person's eye undergoes accommodation convergence.

According to some aspects, a method of compensating for accommodative convergence that occurs in an eye comprises: detecting that accommodative convergence has occurred in the eye; and increasing a depth of field of the eye by decreasing an aperture size of a device that is implanted in or on the eye and the device provides a variable aperture by using an electrochemical, electromechanical, or mechanical mechanism.

According to some aspects, a method of controlling and/or powering a device located in the eye and having an optically adjustable element comprises: sending an electrical, RF, or electromagnetic control signal from an external device; receiving the control signal by a sensor or a receiver at the optically adjustable element; and initiating an electrical, electro-mechanical, electro-chemical or chemical process at the optically adjustable element in response to the received control signal.

In some examples, the method comprises controlling separate sections of the optically adjustable element to modulate incoming light individually or together according to spatial and/or temporal patterns that are encoded in the control signal, to communicate with an individual who uses the optically adjustable element.

In some examples, the device comprises an upgrade interface module and the method further comprises upgrading the device by: connecting a new component to the upgrade interface module while the device is implanted in the eye.

According to some aspects, a method of implanting a device into a user's eye, the device defined according to any one of the appropriate embodiments described herein, comprises: making an incision in the eye; inserting a portion of the device through the incision in the eye; inserting remaining components of the device through the incision; and assembling the components of the device while the components are in the eye.

In some examples, the device comprises an upgrade interface module and the method further comprises upgrading the device by connecting a new component to the upgrade interface module.

According to some aspects, a method of decreasing dysphotopsias and night vision symptoms associated with a multifocal intraocular lens having diffractive elements for a person having an existing intraocular lens and a switchable implanted device that is defined according to any one of the appropriate embodiments described herein, comprises: implanting the device with a specific orientation and positioning to align portions of the device that undergo nanoplating during use with corresponding portions of the multifocal intraocular lens where at least one of the diffractive elements is located such that when nanoplating at the portions of the device occurs to create opaque zones, the corresponding portions of the multifocal intraocular are masked by the opaque zones to decrease night vision symptoms; controlling the device to activate nanoplating either manually with an external device or automatically via a learning predictive algorithm when the person is not interested in reading and wishes to see objects at a distance without stray light and dysphotopsias caused by certain diffractive elements of the multifocal lens; and controlling the device to undergo reverse nanoplating either (1) manually via the external device when the user wishes to read to remove the opaque zones of the device that are in front of certain diffractive components of the lens, or (2) automatically when the learning predictive algorithm predicts a likelihood of reading for the person.

According to some aspects, a method of decreasing dysphotopsias and night vision symptoms associated with a refractive zonal lens having zonal refractive elements for a person having an existing intraocular lens and a switchable device that is defined according to any one of the appropriate embodiments described herein, comprises: implanting the device with a specific orientation and positioning to align portions of the device that undergo nanoplating during use with corresponding portions of the refractive zonal lens where at least one of the refractive elements is located such that when the nanoplating at the portions of the device occurs to create opaque zones, the corresponding portions of the refractive zonal lens are masked by the opaque zones; controlling the device to activate nanoplating either (1) manually with an external device when the person wishes to see objects at a distance without stray light and dysphotopsias caused by the zonal refractive components and the person is not interested in reading, or (2) automatically with a learning predictive algorithm that predicts a likelihood of the person not reading; and controlling the device to undergo reverse nanoplating either (1) manually via the external device when the user wishes to read to remove the opaque zones of the device that are in front of certain zonal refractive components of the lens, or (2) automatically when the learning predictive algorithm predicts a likelihood of reading for the person.

In some examples, the lens comprises two or more refractive zones and the portions of the device are nanoplated to modulate incoming light so light is not transmitted to at least one of the refractive zones and the lens functions as a regular monofocal lens to improve visual comfort and visual function.

In some examples, the lens comprises one or more diffractive optical elements and the portions of the device are nanoplated to modulate incoming light so light is not transmitted to at least one of the one or more diffractive optical elements of the lens to improve visual comfort and visual function when the individual wishes to see distance with minimal stray light or dysphotopsias.

In some examples, the lens comprises one or more phase shift elements and the portions of the device are nanoplated to modulate incoming light so light is not transmitted to at least one of the one or more phase shift elements of the lens to improve visual comfort and visual function when the user wishes to see distance vision with minimal stray light or dysphotopsias.

According to some aspects, a method of improving dark adaptation of a user by controlling an amount of light that enters into an eye of a person when the eye includes a device for modulating incoming light, the device being defined according to any one of the appropriate embodiments described herein, comprises: controlling the device to decrease an aperture of the device to minimize the amount of light transmitted through the device to allow for increased dark adaptation to occur in the eye under ordinary illumination; and controlling the device to rapidly increase the aperture of the device to increase and allow for increased light transmission when the user is suddenly transitioned into a dark environment, wherein the device is controlled either by direct communication from the person to the device and/or is triggered by a sensor that is used to sense when the visual environment of the person is either suddenly darkened or ambient lighting is lowered acutely in a short period of time that is faster than the person is naturally able to dark adapt to ambient illumination in the person's visual environment.

According to some aspects, a method of controlling an amount of light that enters into an eye of a person when the eye includes a device for modulating incoming light, the device being defined according to any one of the appropriate embodiments described herein, comprises: controlling the device to decrease an aperture of the device to increase the depth of field for the person to allow the person to read or view a near object in detail; wherein the device is controlled either by communication with a controller of the device by the person, or the controller is triggered by a sensor or a reading algorithm that is used to predict a likelihood that the person wishes to read something at a near distance wherein the reading algorithm takes into account the person's level of focus, context and visual task.

According to some aspects, a method of optimizing a visual dynamic range of a person by controlling an amount of light that enters into an eye of the person when the eye includes a device for modulating incoming light, the device being defined according to any one of the appropriate embodiments described herein and being configured to provide variable aperture sizes, comprises: determining optimal aperture sizes for a maximum functional dynamic range for performing a given task under different ambient lighting conditions for the person; detecting a change in illumination in an environment of the person; and providing an applied voltage of a predetermined charge, pattern, magnitude and duration when the change in illumination is detected to change the aperture size of the device to one of the optimal aperture sizes for the illumination of the environment of the person to result in the optimal dynamic range for a task for a specific individual.

In another broad aspect, a method is provided of improving regulation of circadian rhythm of a person by controlling an amount of light that enters into an eye of the person when the eye includes a device for modulating incoming light, the device being defined according to any one of the appropriate embodiments described herein, and being configured to provide variable aperture sizes, wherein the method comprises: (a) detecting ambient illumination levels at various time points throughout the day using at least one illumination sensor; (b) determining an effective pupil size based on the detected ambient illumination level at a given time point and the person's circadian rhythm for the given time point; and (c) providing a charge voltage to an element of the device according to a predetermined polarity, pattern, magnitude, and duration to set the aperture size to correspond to the effective pupil size.

In some examples, the method comprises controlling at least one element of the device to undergo nanoplating to provide a smaller aperture size and allow less light transmission when the person's circadian rhythm indicates that the person should prepare for sleep regardless of high intensity illumination levels in the person's environment. In other embodiments, the transparency level is altered to change the amount of blue light transmitted to the person's eye.

In some examples, the method comprises controlling at least one element of the device to undergo reverse nano-plating to provide a larger aperture size when more light is necessary for fulfilling a task or the person is in the early morning component of their circadian rhythm and should be exposed to more light.

In some examples, the method further comprises determining an effective transparency based on the detected ambient illumination level at the given time point and the person's circadian rhythm for the given time point, and wherein the charge voltage provided in step (c) sets the transparency of the device to correspond to the effective transparency.

According to some aspects, a method of improving regulation of circadian rhythm of a person having an eye with an implanted ocular device for modulating incoming light includes: (a) determining a suitable amount of light for entering the person's eye at a given time point based on a predetermined circadian rhythm for the person; and (b) providing a charge voltage to an optically adjustable element of the device at around the given time point to set the amount of light entering the person's eye to correspond to the suitable amount of light. In at least one embodiment, in response to the charge voltage, the optically adjustable element adjusts at least one of an aperture size, a transparency level, and a blue light filtration level. In at least one embodiment, the charge voltage is provided according to a predetermined polarity, pattern, magnitude, and duration.

According to some aspects, a method of identifying accommodation convergence in a person's eye, includes: (a) tracking markers of an ocular device implanted in or on the eye, the markers tracked using an observing device having a tracking sensor, the markers tracked relative to each other and to a position of the observing device to generate a tracked pattern; (b) comparing the tracked pattern to a pre-defined marker pattern for the person, the pre-defined marker pattern obtained during accommodation convergence in the person's eye; and (c) determining that accommodation convergence is occurring when the tracked pattern corresponds to the pre-defined marker pattern.

In some examples, step (a) includes tracking the markers in 3-dimensional space and time.

In some examples, step (c) includes determining that the positions, torsional movements, and 3-dimensional movements of the markers relative to each other over time in the tracked pattern correspond to that in the pre-defined marker pattern.

According to some aspects, a method of controlling operation of an ocular optic device to compensate for accommodative convergence in the eye includes operating a controller in communication with the device to: (a) determine that accommodative convergence has occurred in the eye based at least in part on input from one or more sensors; and (b) in response to (a), generate a control signal for adjusting the optic device to extend a depth of field for the eye.

In some examples, adjusting the optic device comprises decreasing an aperture size provided by the optic device.

In some examples, adjusting the optic device comprises initiating at least one of a chemical, electrochemical, electromechanical, and mechanical process.

According to some aspects, a method of controlling operation of an adjustable intraocular optic device implanted in an eye, includes: transmitting a control signal from an external device, the control signal receivable by the optic device for initiating an adjustment process to adjust an optical element of the device.

In some examples, the method includes receiving the control signal at the optic device, and in response to receiving the control signal, initiating the adjustment process.

In some examples, the control signal is received by at least one of a sensor and a receiver of the optic device.

In some examples, the adjustment process comprises at least one of mechanical, electro-mechanical, electro-chemical, and chemical process.

In some examples, the control signal comprises at least one of an electrical, RF, or electromagnetic signal.

In some examples, the adjustment process comprises modulating incoming light according to a pattern encoded in the control signal to communicate information to an individual having the eye in which the optic device is implanted.

In some examples, the adjustment process includes controlling separate sections of the optical element to modulate incoming light according to the pattern.

In some examples, the separate sections are controllable individually to modulate the incoming light according to the pattern.

In some examples, the separate sections are controllable together to modulate the incoming light according to the pattern.

In some examples, the pattern comprises at least one of a spatial pattern and a temporal pattern.

In some examples, the optic device comprises an upgrade interface module and the method further comprises upgrading the device by connecting a new component to the upgrade interface module while the device remains implanted in the eye.

According to some aspects, a method of controlling operation of an ocular optic device implantable in an eye to reduce dysphotopsias and night vision symptoms associated with optical elements of an intraocular lens implantable in the eye, includes operating a controller in communication with the device to: generate a first control signal for transitioning one or more optical portions of the optic device from a generally transparent state, in which the optical elements are optically active, to a generally opaque state, in which at least some of the optical elements are masked by the optical portions and optically inactive for reducing dysphotopsias and night vision symptoms.

In some examples, the lens comprises a multifocal lens and the optical elements comprise diffractive elements.

In some examples, the lens comprises a refractive zonal lens and the optical elements comprise zonal refractive elements.

In some examples, the lens comprises one or more phase shift elements, and when the one or more optical portions are in the opaque state, light is not transmitted to at least one phase shift element to improve visual comfort and visual function when the user wishes to see distance vision with minimal stray light or dysphotopsias.

In some examples, the transitioning comprises nanoplating the optical portions to reduce an opacity of the optical portions.

In some examples, the method includes operating the controller to generate a second control signal for transitioning the one or more optical portions back to the transparent state.

In some examples, the method includes receiving the first control signal at the optic device and initiating the transitioning of the one or more optical portions.

In some examples, the control signal is transmitted to the optic device from an external device.

In some examples, the control signal is generated via user input.

In some examples, the first control signal is generated automatically based on sensor input.

In some examples, the first control signal is generated automatically based on input from a predictive algorithm.

In some examples, the lens functions as a monofocal lens when the one or more optical portions are in the opaque state.

According to some aspects, a method of controlling operation of an adjustable ocular optic device to facilitate dark adaptation for an eye of a user, includes operating a controller in communication with the device to: (a) generate a first control signal for adjusting the optic device to reduce an amount of light being transmitted into the eye to facilitate dark adaptation under ordinary illumination; (b) determine that environmental illumination has decreased based at least in part on input from one or more sensors; and (c) in response to (b), generate a second control signal for adjusting the optic device to increase the amount of light being transmitted into the eye.

In some examples, adjusting the optic device in (a) includes decreasing an aperture size provided by the ocular device, and adjusting the optic device in (c) includes increasing the aperture size.

In some examples, adjusting the optic device in (a) includes decreasing a transparency of an optical element of the optic device, and adjusting the optic device in (c) includes increasing the transparency of the optical element.

In some examples, the one or more sensors include at least one illumination sensor for generating sensor signals indicative of the environmental illumination.

In some examples, the controller determines that the environmental illumination has decreased in response to determining, based at least in part on the input from the illumination sensor, that a rate at which the environmental illumination is decreasing is greater than a rate at which the eye is able to naturally adapt to the darkening environment.

According to some aspects, a method of controlling operation of an adjustable ocular optic device to adjust a depth of field for an eye, includes operating a controller in communication with optic device to: (a) determine at least one of environmental conditions and intraocular conditions based at least in part on input from one or more sensors; (b) determine an optimal depth of field for the eye based on the at least one of environmental conditions and intraocular conditions; and (c) generate a control signal for adjusting the optic device to provide the optimal depth of field for the eye.

In some examples, adjusting the optic device includes adjusting an aperture size of an aperture provided by optic device to provide the optimal depth of field.

In some examples, the method further includes operating the controller to determine that a present depth of field being provided by the optic device is different from the optimal depth of field.

In some examples, a method of controlling operation of an ocular optic device to optimize a visual dynamic range for an eye of a user, includes operating a controller in communication with the device to: (a) determine a first illumination level for an environment of the user based at least in part on input from one or more sensors; (b) select a first optimal pupil size for the first illumination level, the first optimal pupil size selected from a plurality of optimal pupil sizes pre-determined for a functional dynamic range for performing a given task under different illumination levels; and (c) generate a first control signal for adjusting an aperture size of an aperture provided by the optic device to correspond to the first optimal pupil size.

In some examples, the method further includes operating the controller to: after (c), (d) determine a change from the first illumination level to a second illumination level for the environment; (e) select a second optimal pupil size for the second illumination level from the plurality of optimal pupil sizes; and (f) generate a second control signal for adjusting the aperture size to correspond to the second optimal pupil size.

In some examples, adjusting the aperture size comprises providing an applied voltage of a predetermined charge, pattern, magnitude, and duration to at least one element of the optic device.

According to some aspects, a method of controlling operation of an ocular optic device to optimize a visual dynamic range for an eye of a user, includes operating a controller in communication with the device to: (a) determine a first illumination level for an environment of the user based at least in part on input from one or more sensors; (b) select an optimal first transparency level for the first illumination level, the optimal first transparency level selected from a plurality of optimal transparency levels pre-determined for a functional dynamic range for performing a given task under different illumination levels; and (c) generate a first control signal for adjusting a transparency level of an optical element of the optic device to correspond to the first optimal transparency level.

In some examples, the optimal first transparency level corresponds to filtration of a predetermined wavelength range of electromagnetic radiation.

In some examples, the method further includes operating the controller to: after (c), (d) determine a change from the first illumination level to a second illumination level for the environment; (e) select a second optimal transparency level for the second illumination level, the second optimal transparency level selected from the plurality of optimal transparency levels; and (f) generate a second control signal for adjusting the transparency level of the optical element to correspond to the second optimal transparency level.

According to some aspects, a method of controlling operation of an ocular optic device to optimize a visual dynamic range for an eye of a user, includes operating a controller in communication with the device to: (a) determine an illumination level for an environment of the user based at least in part on input from one or more sensors; (b) select an optimal pupil size for the illumination level; (c) select an optimal first transparency level for the first illumination level, the optimal pupil size and the optimal transparency level selected from a plurality of optimal pupil sizes and transparency levels pre-determined for a functional dynamic range for performing a given task under different illumination levels; and (d) generate a control signal for adjusting (i) a transparency level of an optical element of the optic device to correspond to the optimal transparency level, and (ii) an aperture size of an aperture provided by the optic device to correspond to the optimal pupil size.

According to some aspects, a method of controlling operation of an adjustable ocular optic device to regulate circadian rhythm of a user, includes operating a controller in communication with the device to: (a) determine an optimal amount of light for entering the user's eye at a given time point based on a predetermined circadian rhythm for the user; and (b) generating a control signal for adjusting the optic device at around the given time point so that the amount of light entering the person's eye corresponds to the optimal amount of light.

In some examples, adjusting the optic device comprises adjusting at least one of an aperture size, a transparency level, and a blue light filtration level of the optic device.

In some examples, the method further includes operating the controller to: determine an environmental illumination level based at least in part on input from one or more sensors; determine an optimal pupil size based on the environmental illumination level and the predetermined circadian rhythm; and wherein adjusting the optic device comprises adjusting an aperture size of an aperture provided by the optic device to correspond to the optimal pupil size.

In some examples, adjusting the optic device comprises providing an applied voltage of a predetermined charge, pattern, magnitude, and duration to at least one element of the optic device.

In some examples, adjusting the optic device comprises nanoplating at least one element of the optic device to adjust at least one of an aperture size and a transparency level of the optic device.

According to some aspects, a method of coordinating operation of an adjustable first optic device implantable in a first eye of a user and an adjustable second optic device implantable in a second eye of a user, includes operating a controller in communication with the first optic device and the second optic device to: (a) determine a first function for the first eye and a second function for the second eye based at least in part on input from one or more sensors; (b) generate a first control signal for adjusting the first optic device to provide the first function for the first eye; and (c) generate a second control signal for adjusting the second optic device to provide the second function for the second eye.

In some examples, the first function comprises a first function type, and the second function comprises a second function type different from the first function type.

In some examples, wherein each of the first function type and the second function type is selected from the group consisting of: a transparency level, aperture size, depth of field, depth of field near limit, filtration of an electromagnetic wavelength range, and visual information, provided by a respective optic device for a respective eye.

In some examples, the first function comprises a first transparency level provided by the first optic device, and the second function comprises a second transparency level provided by the second optic device, the first transparency level different from the second transparency level.

In some examples, the first function comprises a first aperture size provided by the first optic device, and the second function comprises a second aperture size provided by the second optic device, the second aperture size different from the first aperture size.

In some examples, the first function comprises a first depth of field, and the second function comprises a second depth of field, the second depth of field different from the first depth of field.

In some examples, the first function comprises near vision focus, and the second function comprises distance vision focus.

In some examples, the first function comprises filtration of a first electromagnetic wavelength range by the first optic device, and the second function comprises filtration of a second electromagnetic wavelength range by the second optic device, the second electromagnetic wavelength range different from the first electromagnetic wavelength range.

In some examples, the first function comprises first visual information provided by the first optic device, and the second function comprises second visual information provided by the second optic device, the second visual information different from the first visual information.

In some examples, the first function and the second function are complementary to improve functional vision for a given task.

In some examples, the controller determines the first function and the second function to facilitate dark adaptation for at least one of the first eye and the second eye.

In some examples, the controller determines the first function and the second function to provide an optimized visual dynamic range for a given task, for at least one of the first eye and the second eye.

In some examples, the method further includes receiving the first control signal at the first optic device when implanted in the first eye and initiating adjustment of the first optic device to provide the first function for the first eye, and receiving the second control signal at the second optic device when implanted in the second eye and initiating adjustment of the second optic device to provide the second function for the eye.

In some examples, the first and second control signals are generated at an external device.

In some examples, the first and second control signals are generated at around the same time for initiating adjustment of the first and second optic devices generally simultaneously.

In some examples, the one or more sensors comprise at least one environment sensor for generating sensor signals indicative of environmental conditions.

In some examples, the environment sensor comprises at least one of: an illumination sensor for generating sensor signals indicative of environmental illumination, and a rangefinder for measuring distance to an object of interest.

In some examples, the one or more sensors comprise one or more intraocular sensors for generating sensor signals indicative of intraocular conditions in at least one of the first eye and the second eye.

Other features and advantages of the present application will become apparent from the following detailed description taken together with the accompanying drawings. It should be understood, however, that the detailed description and the specific examples, while indicating one or more embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIGS. 2A-2C are schematic front views of the intraocular prosthesis system of FIGS. 1A-1C in different states.

FIG. 12 is a schematic of another example intraocular prosthesis system.

FIGS. 13A and 13B are front schematic views of an example adjustable optical element for an intraocular prosthesis system like that of FIG. 12, and showing an occludable optical portion of the optical element in different states.

FIG. 14A is a side schematic view of another example adjustable optical element having an optical portion with an adjustable morphology;

FIG. 14B is a side schematic view of a diffractive lens portion in a first morphology;

FIG. 14C is a side schematic view of the diffractive lens portion of FIG. 14B in a second morphology;

FIG. 15 is a side schematic view of another example adjustable optical element having an optical portion with an adjustable refractive index.

FIGS. 16A and 16B are front schematic views of an example adjustable meta-lens assembly shown in different states for an intraocular prosthesis system like that of FIG. 12.

FIG. 17 is a side schematic view of portions of the meta-lens assembly of FIGS. 16A and 16B.

FIG. 17A is an enlarged view of a portion of FIG. 17.

FIGS. 17B-17E are similar to FIG. 17A, but show waveguide structures of the meta-lens assembly in different adjustment states.

Figure 1A:
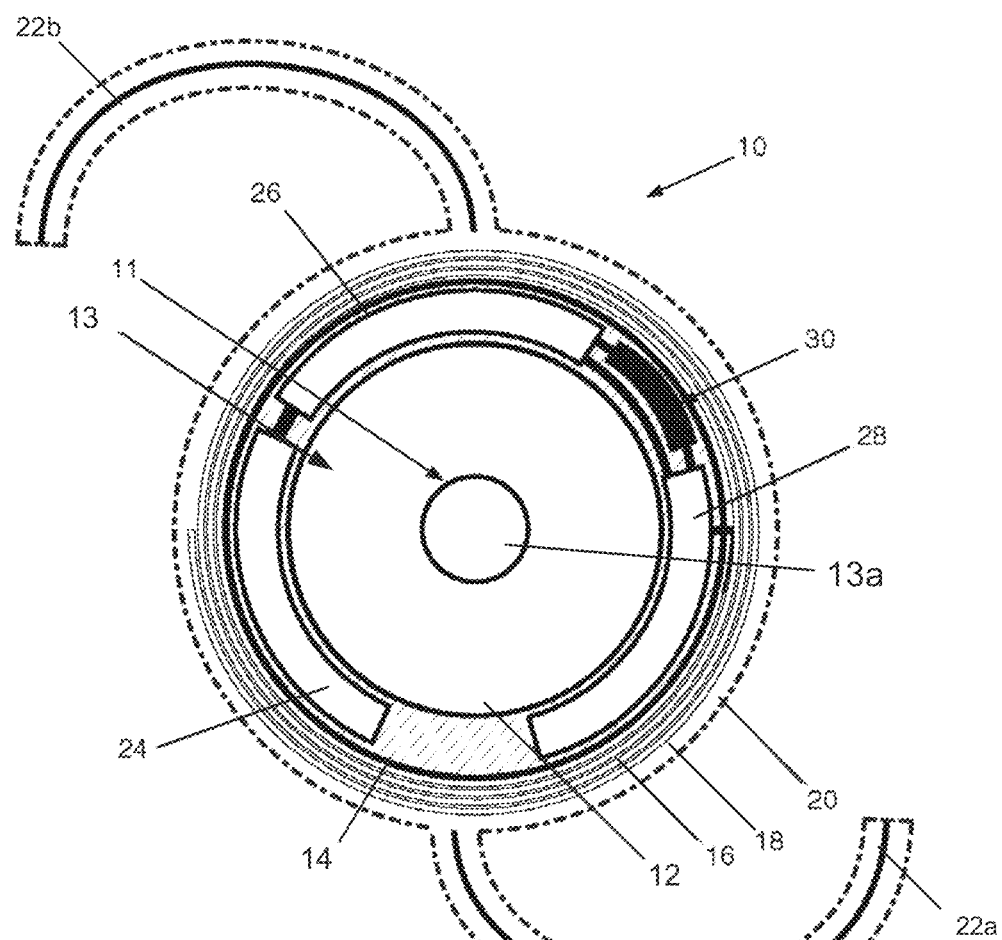
FIGS. 1A-1B are front and side views of an example embodiment of an intraocular prosthesis system in accordance with the teachings herein.

Further aspects and features of the example embodiments described herein will appear from the following description taken together with the accompanying drawings.

DETAILED DESCRIPTION OF THE EMBODIMENTS

Various systems, devices or methods will be described below to provide an example of at least one embodiment of the claimed subject matter. No embodiment described herein limits any claimed subject matter and any claimed subject matter may cover systems, devices, or methods that differ from those described herein. The claimed subject matter is not limited to systems, devices, or methods having all of the features of any one system, process, or device described below or to features common to multiple or all of the systems, devices, or methods described herein. It is possible that a system, device, or method described herein is not an embodiment of any claimed subject matter. Any subject matter that is disclosed in a system, device, or method described herein that is not claimed in this document may be the subject matter of another protective instrument, for example, a continuing patent application, and the applicants, inventors, or owners do not intend to abandon, disclaim, or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures, and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical, or communicative connotation. For example, as used herein, the terms coupled or coupling can indicate that two or more elements or devices can be directly connected to one another or connected to one another through one or more intermediate elements or devices via an electrical element, an electrical signal, or a mechanical element depending on the particular context. Furthermore, the term "communicative coupling" indicates that an element or a device can electrically, or wirelessly send data to or receive data from another element or device depending on the particular embodiment.

It should also be noted that, as used herein, the wording "and/or" is intended to represent an inclusive-or. That is, "X and/or Y" is intended to mean X or Y or X and Y, for example. As a further example, "X, Y, and/or Z" is intended to mean X or Y or Z or any combination thereof (i.e. X and Y, X and Z, Y and Z, or X, Y, and Z).

It should also be noted that terms of degree such as "substantially", "about" and "approximately" as used herein mean a reasonable amount of deviation of the modified term such that the end result is not significantly changed. These terms of degree may also be construed as including a deviation of the modified term, such as but not limited to 1%, 2%, 5% or 10%, if this deviation does not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about", which means a variation of up to a certain amount of the number to which reference is being made if the end result is not significantly changed, such as but not limited to 1%, 2%, 5% or 10%, for example.

In accordance with the teachings herein there is provided a intraocular prosthesis system, which in some examples comprises a bionic iris device (also referred to as a prosthetic iris device), and that is structured and configurable to vary one of its properties to provide a useful function when implanted in an eye of a user. The user can be a human or an animal. For example, the bionic iris device can vary one of its properties in order to operate as a dynamic iris prosthesis and mimic or replace the function of the iris when implanted in an eye. For example, the bionic iris device can be used to vary the amount of light that is transmitted to the interior of the eye.

In an example embodiment, the dynamic functional iris prosthesis device has the ability to vary the opacity of specific components of the device between various levels of transparency and opacity. One function of varying transparency allows the device to effectively change the pupil aperture size, similar to the function of a normal iris to improve and potentially enhance the visual perception and depth of field of the user. Another function of varying transparency can include adjusting the amount of blue light transmitted to the user to affect the user's circadian rhythm.

In at least one embodiment, the device may be powered or triggered for use by a photovoltaic power source.

In another example use, the bionic iris device can be used to implement small aperture optics and achieve certain optical, refractive, diffractive, and/or other effects to improve (e.g. dynamically adjust) the depth of field for users, which allows for images to be sharp through a larger range of distances, which may help with difficulties encountered with near vision in the setting of presbyopia.

In another example use, an optical property of at least one embodiment of the bionic iris device can be controlled and varied, when implanted bilaterally in both eyes of an individual, to improve the dark adaptation of an individual transitioning quickly between bright and dark environments.

In another example use, an optical property of at least one embodiment of the bionic iris device can be controlled and varied to optimize an individual's dynamic range to improve functional vision.

In another example use, an optical property of at least one embodiment of the bionic iris device can be controlled and varied, when implanted bilaterally in both eyes of an individual, to improve the regulation of an individual's circadian rhythm. This may be especially helpful when the individual is engaged in shiftwork or switching time zones, or is often in very bright environments even late into the evening, close to or during the designated resting portion of that individual's circadian rhythm.

In another example use, a property of the bionic iris device can be varied to provide augmented reality to the user and to provide additional information to a user beyond what is apparent. For example, the bionic iris device can be configured to display visual elements in the user's field of view.

In another example use, a property of the bionic iris device can be varied to change an outward appearance of the user's eye. For example, a property of the bionic iris device can be varied to change the user's eye color and/or pattern. In another embodiment of the device an externally visible portion of the device can be used for tracking, including but not limited to tracking the visual axis, gaze, and position of the eye in 3-dimensional space including cyclotorsion and time.

In another example embodiment, at least one sensor can be incorporated into the bionic iris device to perform a measurement of the user. For example, the bionic iris device can have a sensor that is used for sensing ambient lighting, and/or at least one biomarker sensor to measure at least one corresponding biomarker in the user's eye. The sensor may also be a sensor that can detect motion, electrical activity, position, pressure, or temperature and the sensor may be active or passive. The pressure sensor may be advantageous since many patients who require an iris prosthesis due to trauma or congenital etiologies also have difficulty with having high pressures which can cause nerve damage, and therefore monitoring pressure may be especially beneficial in these settings.

In some embodiments, the device can also be configured to be used anterior to the eye, including but not limited to the surface of the cornea or in other embodiments, designed to float on the tear film anterior to the cornea.

In another example embodiment, the bionic iris device can include certain electronic components for performing certain functions. For example, in at least one embodiment, the bionic iris device comprises an electronic component for wirelessly receiving energy at different frequencies where the energy is used to power the bionic iris device. In at least one embodiment, the device may be powered by resonance induction power. In at least one other embodiment, the device may be powered by direct induction. In at least another embodiment the device may be powered by radiowaves. In at least another embodiment, the device may be powered by a network of radiowaves of different frequencies.

In another embodiment, the device comprises an electronic component for providing a memory for storing data. In yet another embodiment, the device comprises a component for storing electric power such as a capacitor or a battery.

In another example embodiment, the bionic iris device comprises an upgrade interface module that has a port (i.e. an upgrade port) that allows for upgrades to the operation and functionality of the device by allowing for other electronic components to be implanted. The upgrade port can be implemented to allow for implantations in various stages for gradual upgrades over time. In some embodiments, there is redundant circuitry to allow for upgrades where circuitry can be either changed, severed or re-routed by, for example, severing a connection on the device with the use of a focused laser such as a Femtosecond laser, a YAG laser or an Argon laser, without the need to enter the eye.

In least one embodiment described herein, there is provided a method to selectively optically shield (e.g. occlude), on demand, components or portions of a lens, such as the refractive or diffractive elements or portions of a multifocal lens, and thus either decrease or eliminate night vision symptoms (e.g. visual artifacts such as halos) or dysphotopsias associated with the shielded components.

In another embodiment, any type of lens (e.g. monofocal, multifocal, refractive, diffractive, meta-) can be combined and/or integrated with the device to be utilized together.

In at least one embodiment, the device may be able to selectively optically shield specific components in specific patterns to allow for light to be polarized. In different embodiments, this polarization may involve either part of the optical component of the device or the entire field of view.

Figure 1B:
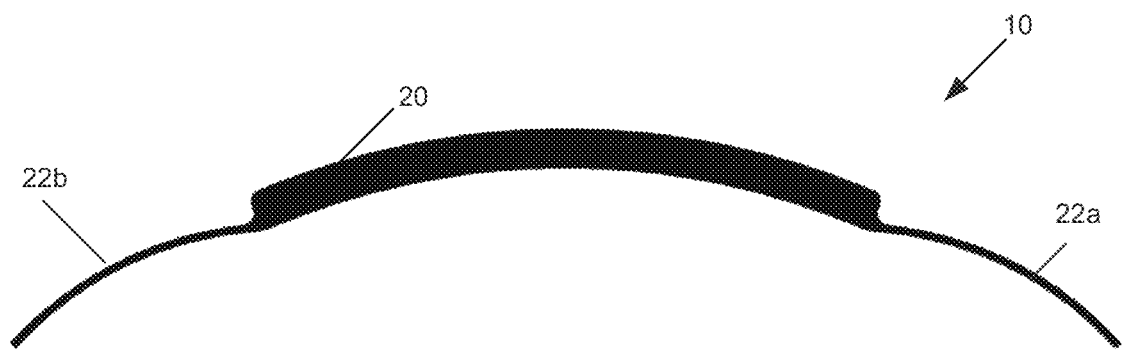

Referring now to FIGS. 1A-1B, shown therein are front and side views of an example embodiment of an intraocular prosthesis system in the form of a bionic iris device 10 in accordance with the teachings herein. The device 10 is a dynamic functional intraocular prosthesis that can mimic the function of the iris. The device 10 comprises an optically adjustable element 13 (also referred to as an adjustable optical element 13) that mimics the pupil, a non-conductive substrate 18, electrical circuitry including a working first electrode 12 that is generally transparent in at least one state, a counter electrode 14, an antenna 16, a controller 28 (which is optional), an energy storage element 26 (which is optional), and an upgrade interface module 30 (which is optional). The device 10 also includes haptics 22a and 22b (which are both optional, and can comprise transducers in some embodiments) as well as a membrane 20 (also referred to as coating 20) which covers the entire device 10. The membrane 20 can comprise, for example, a biocompatible coating (e.g. a thin coating of silicone) sealing the device components.

It should be understood that there can be other embodiments in which the elements of the device 10 are arranged differently or other elements are included or removed. For example, in other embodiments, the electrical circuitry may include at least one battery and/or at least one piezoelectric component and or light source.

Figure 1C:
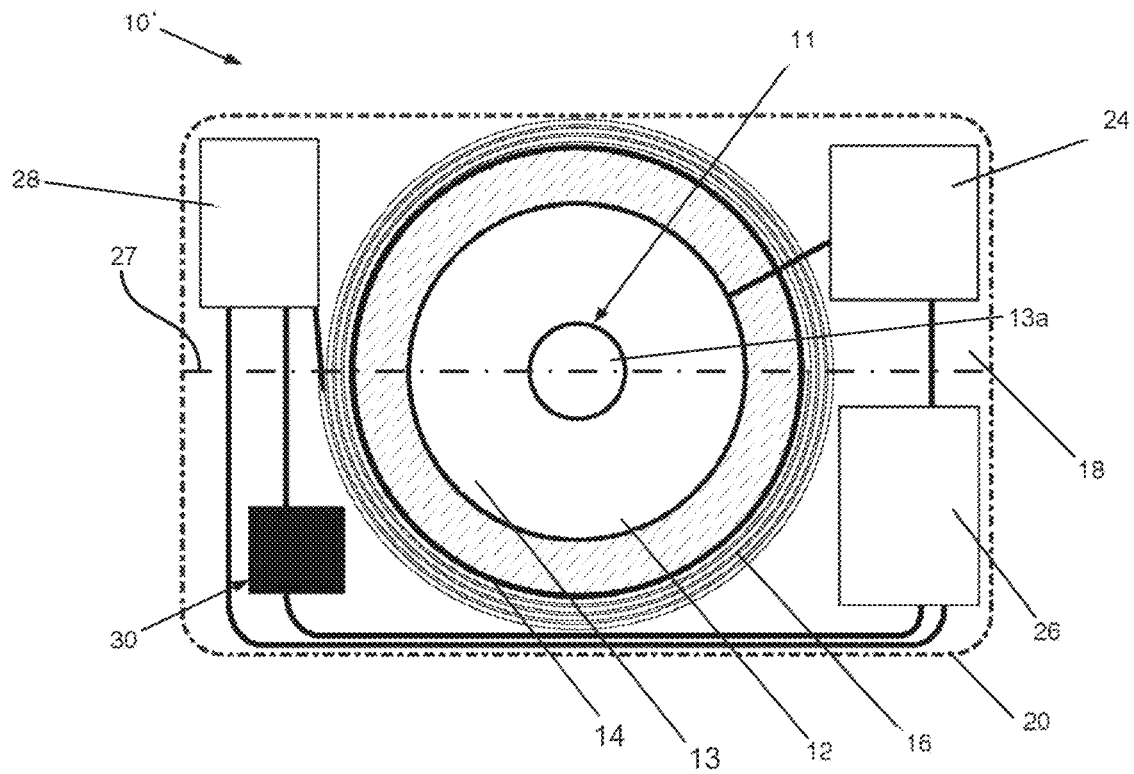
FIG. 1C is a front view of another example embodiment of an intraocular prosthesis system.

The shape of the device 10 may be different in different embodiments. For example, the device 10 can have an overall rounded shape (as shown in FIG. 1A). Alternatively, the device 10 can have a rounded rectangular shape as shown in FIG. 1C for the bionic iris device 10'. Alternatively, the device 10 can have a rounded square, a polyhedral, an elliptical, or any other shape to maximize the structural and/or functional advantages of the device 10 in terms of the components that are used in the device 10 or the way the device 10 needs to be manipulated in order to be implanted into the eye. Referring to FIG. 1C, in the example illustrated, the outer corners of the device 10 are rounded. This can facilitate delivery of the device into the eye and/or removal of the device from the eye, and/or help reduce the potential for injury or trauma during surgical manipulation or from repetitive movements from the overlying iris or underlying ciliary body. Furthermore, all exterior surfaces (and edges) of the device can be smooth to help reduce chafing or injury of portions of the eye either during surgical implantation or after (e.g. due to repetitive movements), and internal components can have a generally low profile (e.g. a thickness/height of generally less than 900-500 µm) so as to not produce any notable protrusions on the device that may interfere with implantation or use of the device.

It should be noted that the electrode 12 overlies the optically adjustable element 13 in the embodiments of FIGS. 1A-1C, which is why elements 12 and 13 are directed to the same general area. However, in other embodiments, such as the nanoplating embodiments, at least this electrode 12 is part of (integrated with) the optically adjustable element 13.

The device 10 is generally referred to rather than both the device 10 and 10' for ease of illustration but it should be understood that the following description of the structure and use of device 10 also applies for device 10' as well as any other variants in shape and proportion.

The various components of the device 10 are generally arranged to define a central optical region 11 at the center of the device 10. In some embodiments, the central optical region 11 is an aperture, which allows for fluid to circulate between the front and middle of the eye through the central region 11 of the device 10, which reduces the potential for the development of pupillary block glaucoma. In other embodiments, the central optical region 11 comprises optically transparent (i.e. clear) materials such as, but not limited to, silicone and/or acrylic, for example. In yet other embodiments of the device 10, this optically transparent material contains at least 1 small circular physical aperture that allows for ingress and egress of fluid and is in the range of about 50 um to 350 um diameter in size, which is smaller than the optical region 11, which may range in size from 1.6 to 2.2 mm in some embodiments. In some embodiments, the small circular physical aperture is placed centrally. In others, it need not be placed centrally and is optimized to the visual stimulus and the fovea. In other embodiments, the small physical aperture does not need to be circular and can be larger in average diameter, though smaller than the optically transparent area.

Figure 6A:
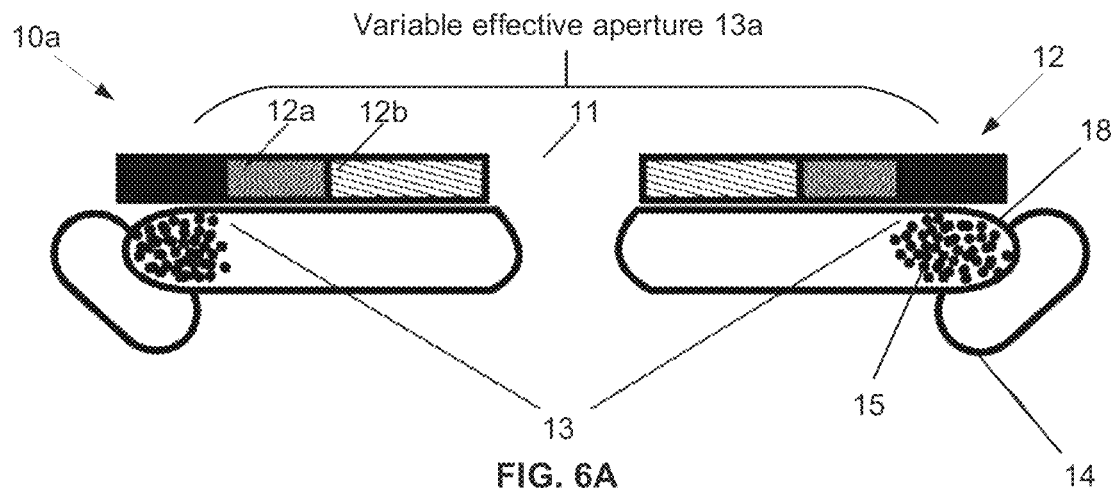
FIGS. 6A-6C are side views of a portion of the intraocular prosthesis system of FIGS. 1A-1C in different states.
Figure 6B:
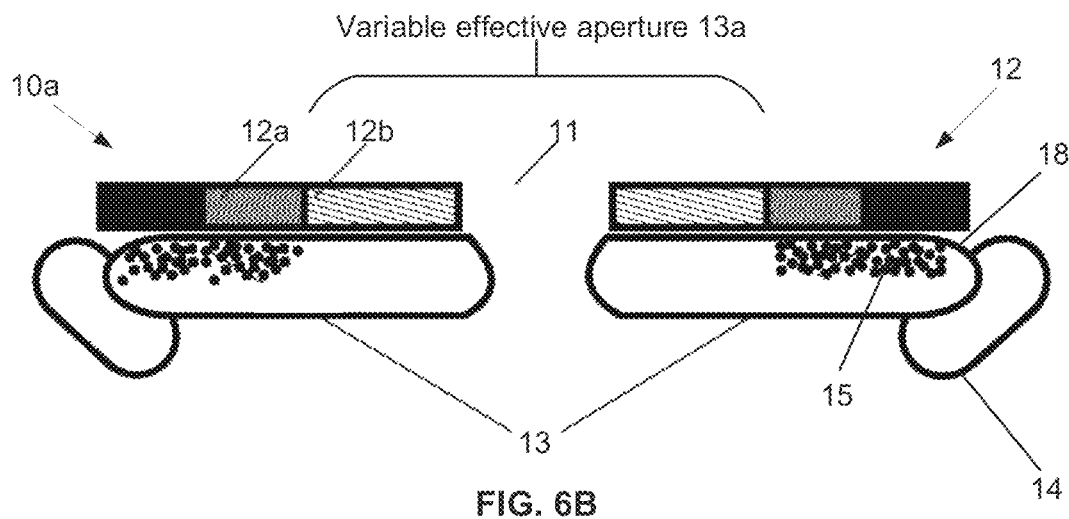
Figure 6C:
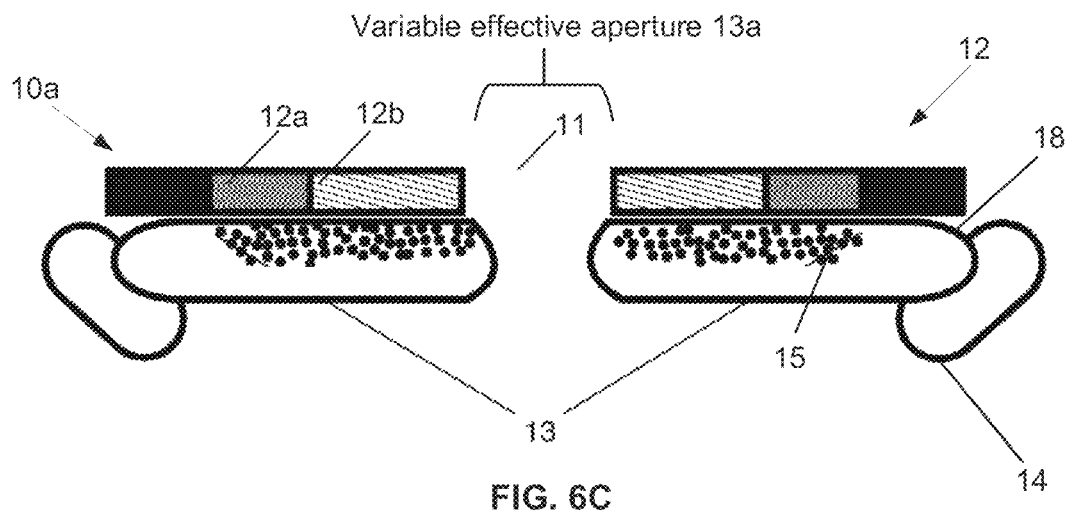

The device 10 is dynamic since it can vary the optically adjustable element 13 to effectively provide a variable optical aperture (i.e. an adjustable aperture stop) to control the size of the pupil similar to when a normal iris changes in size as shown in FIGS. 6A-6C which show how the optically adjustable element 13 can be adjusted to provide three different pupil sizes. This is done by dynamically varying the light transmission through the optically adjustable element 13, which has a light property, such as light transmission, for example, that can be varied over a certain spectral range. The light transmission can be varied by changing the reflectance or absorption of certain portions of the optically adjustable element 13 by using, for example, electrical or chemical activation. This can be implemented using several different mechanisms as described in further detail below.

For example, the optically adjustable element 13 may comprise at least one smart film, having an adjustable modulating light transmission property for at least one spectral range of light by being altered chemically or electrically or electrochemically, depending on its implementation. The smart film modulates light transmission by changing the amount of light in a given spectral range, that is reflected, absorbed, and transmitted. For example, the smart film can be made with transparent reversibly nanoplatable (nanoscale metal electro-deposition) electrodes, using electrochromic material, suspended particles, or nanocrystals. Alternatively, the smart film may be made using MEMS sheets of metal at a micrometer scale that can bend and stretch with applied power.

In some embodiments, the smart film can be coupled to a capacitor so that when the capacitor is charged, the smart film is activated which causes the optically adjustable element 13 to experience a change in optical transmission which can change the effective aperture 13a. This capacitor may be charged if it is coupled to a device for receiving power, including for example an inductor which receives a wireless charging signal or harnesses energy from a complement of radiowaves of different pre-determined frequencies. For example, an external induction coil that is external to the device 10 can be used to induce a current in the inductor within the device 10 at a specific resonance frequency which will charge the capacitor with magnetic flux. This may be done when the external induction coil is brought in close proximity to the device 10 such as in proximity to the surface of the eye of the user that has the device 10. The necessary magnetic flux may also be generated from a distance using a specific combination of radiowave frequencies at a greater distance. In some embodiments, the use of constructive interference from these different frequencies at a certain distance and tissue depth, allows for the appropriate energy necessary to power the device. This may also be done using frequency-hopping spread spectrum radio technology such as with Bluetooth LE, for example, which potentially makes operating the device 10 more secure.

In some embodiments, such as with nanoplating to create the smart film, the nanoplating of a transparent working electrode is nanoscale electroplating that can be reversed, and therefore the optical modulating properties of the optically adjustable element 13 can be reversed by applying a predetermined charge voltage to the same circuit with an opposite charge, with or without the presence of a capacitor in some embodiments. In such an embodiment, after an electrode of the optically adjustable element has been nanoplated from its original transparent electrode state, when magnetic flux is created by the methods including, but not limited to induction as described above, to create magnetic flux such that the correct charge voltage is applied, the nanoplating can be reversed and the optical modulating element is reversed to its original transparent electrode state.

It should be noted that the term "charge voltage" is used in the context of the nanoplating embodiments to imply a voltage with a specific polarity and a specific magnitude, time and pattern, to enable nanoplating to occur when the voltage is applied between a transparent electrode (i.e. a working electrode) with deposition sites and a counter electrode (i.e. reference electrode). The deposition sites are on a nanoscale in terms of size and thus when ions are attracted to and accumulate at the deposition sites of the transparent electrode, nanoplating is occurring and the transparent electrode is being nanoplated.

It should also be noted that the term "pattern" when used in as a property or attribute of a charge voltage is meant to be understood as a waveform (i.e. signal waveform) that may vary over time to obtain different amounts of charge through the electrolyte. For example, one pattern of the charge voltage may be to have a first high amplitude charge voltage for 100 ms followed by lower amplitude charge voltage for a longer time period followed by a second high amplitude charge voltage for a specific time thereafter where the magnitude of the first and second high amplitude charge voltages can be different or the same.

In one embodiment, the light transmission of the optically adjustable element 13 can be adjusted to decrease the effective aperture to a pinhole size, which may nominally be between about 1.6 mm to about 2.2 mm, such as 1.8 mm, for example, from a wide-open (maximum) size, which may be about 6 mm, for example. Examples of a reduction in the effective aperture are shown in the transition from the aperture of 102 to 112 in FIG. 4A, or the transition from the apertures of 102 to 128 to 130 to 132 in FIG. 4B and the transition for 13a in FIGS. 6A to 6C). The lateral area beyond the effective aperture to the side edges of the device 10 (for example out to a diameter of about 8-9 mm) may be opaque. In some embodiments, this opaque area may contain a reservoir of ions (when nanoplating as in FIGS. 4A-4E) or nanoparticles (as in FIGS. 6A-7C) in a donut (i.e. toroidal) shape surrounding the optical element. In embodiments with nanoplating, where there is this toroid shaped reservoir of ions, there is additional electrolyte to provide more ions which can increase the speed and uniformity of the nanoplating. The reservoir is located outside of the visual axis of the optically adjustable element 13. The effective aperture 13a, shown in various figures herein, is an optically clear (i.e. transparent) region at the center of the device 10.

The active optical zone is a transformable portion of the optically adjustable element 13 that can be controlled, using various techniques as described herein, to physically transform and provide for variable light transmission. The active optical zone may vary in size between the smallest effective aperture size and the outer diameter of the optically adjustable element 13 so that the optically adjustable element 13 can have different regions that are optically transparent, optically opaque or optically translucent. The term "optically opaque", for the purposes of this description, means an area that is relatively opaque to its surroundings in some embodiments and is not meant to be limited only to the state of complete blockage of light transmission. In other words, in some embodiments, a small amount of light transmission is possible when the active optical zone beyond optical region 11 is opaque. This may be used for example when one only requires the minimal amount of time and charge to create just enough opacity to allow the area to be functionally not detectable by the retina of the eye, for example, such as when the dark-adapted or light-adapted detectable threshold of the retina is reached. In some uses of the device 10, selective transmission of light, in addition to the variable transmission of light, may be desirable and can be implemented by modulating the light with the optical element to essentially act as a light filter, such as for specific polarities of light or colours/wavelengths/frequencies of light, which are described in more detail below.

Figure 5A:
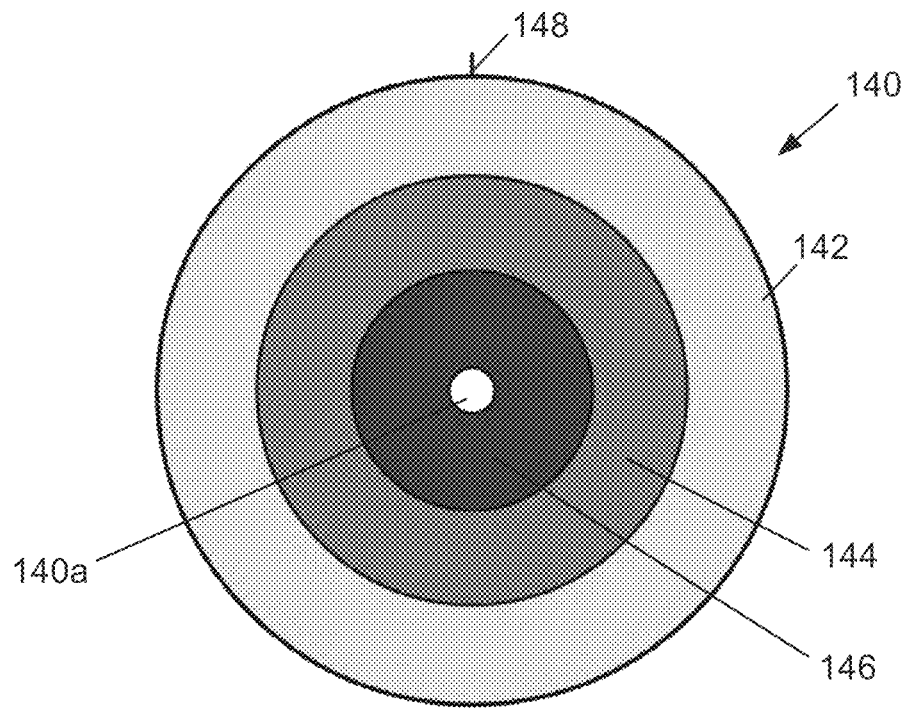
FIG. 5A is an example of an optical state for the optical stack of FIG. 4B.

As best illustrated in FIGS. 5A and 6A-6C, and also applicable to the various other embodiments, during the native resting state, the effective aperture 13a in FIG. 6A and 142, 144, 146 and 140a in FIG. 5A is at a native (i.e. nominal) size where the active optical zone is controlled so that the portion of the optically adjustable element 13 that is within the effective aperture is optically transparent (i.e. clear) while the portion of the optically adjustable element 13 that is outside of the effective aperture is controlled to be optically opaque. The active optical zone can be controlled electrically or chemically or electrochemically in accordance with the teachings herein. The size of the relatively transparent active optical zone defines the size of the iris and therefore the pupil for the user's eye, with smaller active relatively transparent optical zones defining a larger (e.g. wider) iris with a smaller size pupil and larger relatively transparent active optical zones defining a smaller relative (e.g. thinner or narrower) iris with a larger sized pupil. In some embodiments, the exact diameter of the pupil can be controlled either in a step-wise digital or analog fashion from a minimum size to a maximum size therefore allowing for variable aperture sizes optimized for specific visual function.

In some embodiments, the optically active zone of the optically adjustable element 13 can be controlled to provide at least two binary stable states for the device 10 of either: a maximally transparent state (see e.g. FIG. 2A) or a functionally opaque state (see e.g. FIG. 2B). In one embodiment, such as with nanoplating, the device 10 can hold the maximally transparent state, the maximally opaque state as well as any transitional state that lies in the continuum between the most transparent and the most opaque state, without receiving any additional charge voltage, e.g. in a resting state, for long periods of time (for example hours, days, weeks or months), and electric charge or power is used only when switching from one state to another depending on how the optically adjustable element 13 is implemented. As discussed, this is advantageous because it can reduce the amount of energy necessary to operate the device. This can be achieved using a nanoplating embodiment as described below. In other embodiments, one state, for example the transparent state can be designed as the lower equilibrium "resting state" and therefore, when no charge or power is supplied, the device will eventually return to the transparent state. In another embodiment, the reverse can be achieved where the "resting state" is the opaque state or any intermediate state between transparency or opacity. For another example, if the optically adjustable element 13 is made using nanoplating with a custom electrolyte or liquid crystal technology as described below, then the default low equilibrium energy "resting state" (i.e. without receiving any power) can be designed to be the maximal transparent state.

The nonconductive substrate 18 is disposed within the protective membrane 20 (coating) and provides a platform upon which the electrical circuitry is disposed and other components of the device 10 may be disposed. The nonconductive substrate 18 can be made from flexible material such as, but not limited to, silicone, acrylic or a nonconductive wire mesh.

Figure 4A:
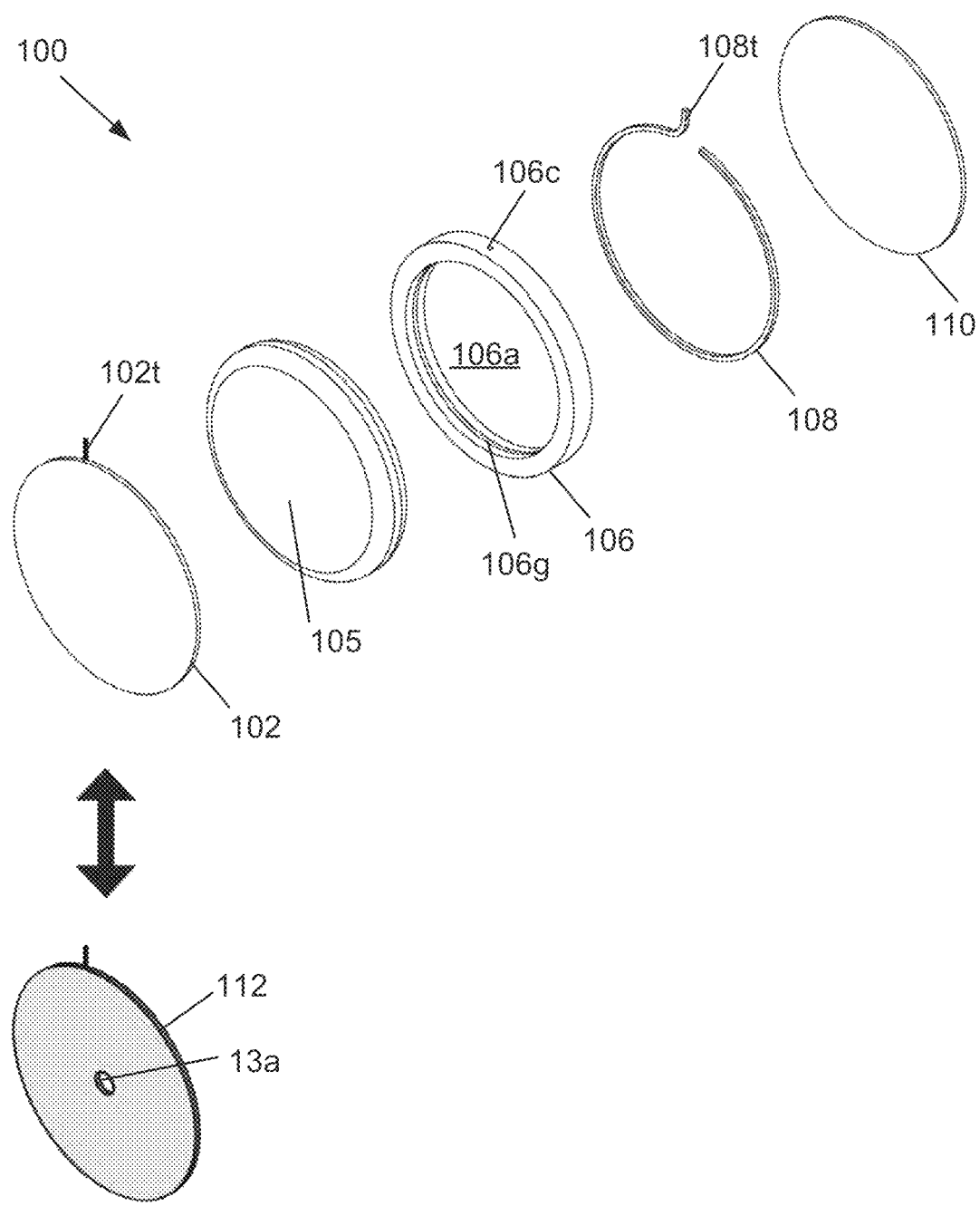
FIG. 4A is an exploded view of an example embodiment of an optical stack that may be used with the systems of FIGS. 1A-1D.

Referring now to FIG. 4A, shown therein is an embodiment of an optical stack 100 that can be used with device 10, which uses nanoplating in accordance with the teachings herein. A first transparent working electrode 102, with electrical lead 102t, and a counter electrode 108, with electrical lead 108t, can be used to apply a charge voltage to the optically adjustable element, to change and modulate the light transmission (i.e. control the amount of variable light transmission) into the eye. In this embodiment, the stack 100 further includes a first non-conductive spacer 106 having an electrolyte medium 105 (also referred to as electrolyte 105), which can be a solution or gel. In this embodiment, the spacer 106 has a groove 106g for receiving the electrode 108 within to isolate it from other electrodes. In the example illustrated, the stack 100 further includes a transparent backplate 110. The spacer 106 has sidewalls defining a central space. The sidewalls have first and second opposed surfaces with the first surface being adjacent to at least the electrode 102. In this embodiment, the second surface is adjacent the transparent backplate 110. The spacer 106 functions as an insulating frame element between the at least one transparent electrode 102 and the at least one counter electrode 108. It may also function to contain the electrolyte medium 105 when the electrolyte medium 105 is liquid. In cases where the electrolyte medium 105 is in a gel or solid form, the spacer 106 can function as a frame element with respect to the electrolyte medium 105.

Figure 4B:
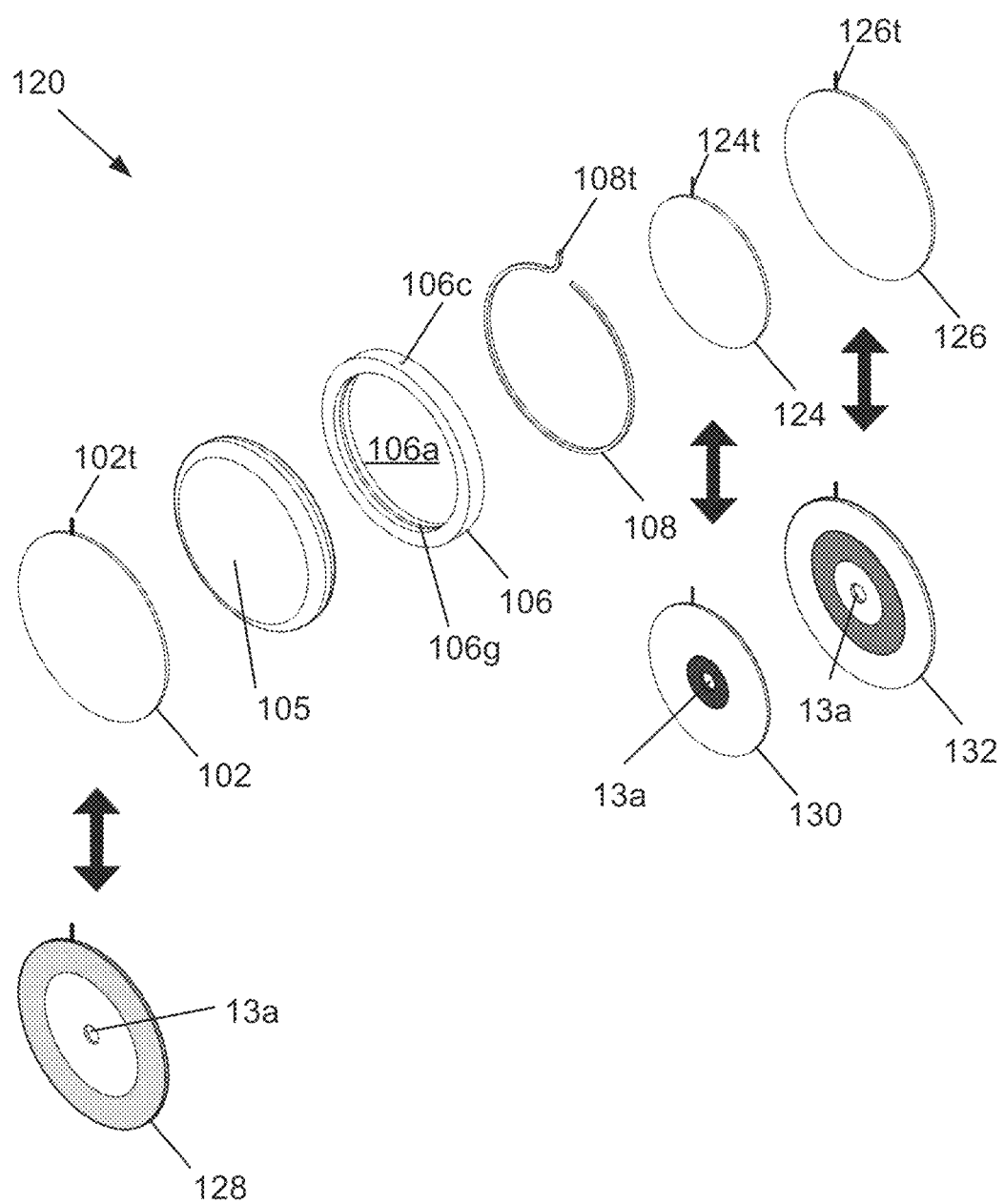
FIG. 4B is an exploded view of an example embodiment of an optical stack that may be used with the systems of FIGS. 1A-1D.

Referring now to FIG. 4B, shown therein is an alternative optical stack 120, which also uses nanoplating in accordance with the teachings herein. The optical stack 120 includes similar elements as the optical stack 100 as well as an additional element and a modified element. The optical stack 120 includes additional electrodes 124, 126, with the electrode 126 acting as a transparent backplate. The electrode 124 is transparent and porous and located within the electrolyte. It should be noted that in alternative embodiments there can be multiple electrodes 124 or no electrodes 124, and only an additional electrode 126 (acting as a backplate), and only one electrode 124 is shown in FIG. 4B for simplicity.

In the embodiments of FIGS. 4A and 4B, the optically adjustable element includes the electrode 102 (FIG. 4A) or the electrodes 102, 124 and 126 (FIG. 4B) as nano-plating occurs on these electrodes, depending on the charge, pattern, magnitude and duration of one or more applied charge voltages, to vary an optical property of the device 10.

Also, in the embodiments shown in FIGS. 4A and 4B, the counter electrode 108 is an encircling element, and can have any encircling shape including but not limited to circular, polygon, elliptical, or any freeform encircling shape that might not be symmetric in any dimension. The encircling counter electrode 108 has a central space that the electrolyte may pass through. In some examples, a plurality of counter electrode portions can be provided, each extending over a respective circumferential segment, rather than having one generally continuously encircling element for the counter electrode.

Figure 4C:
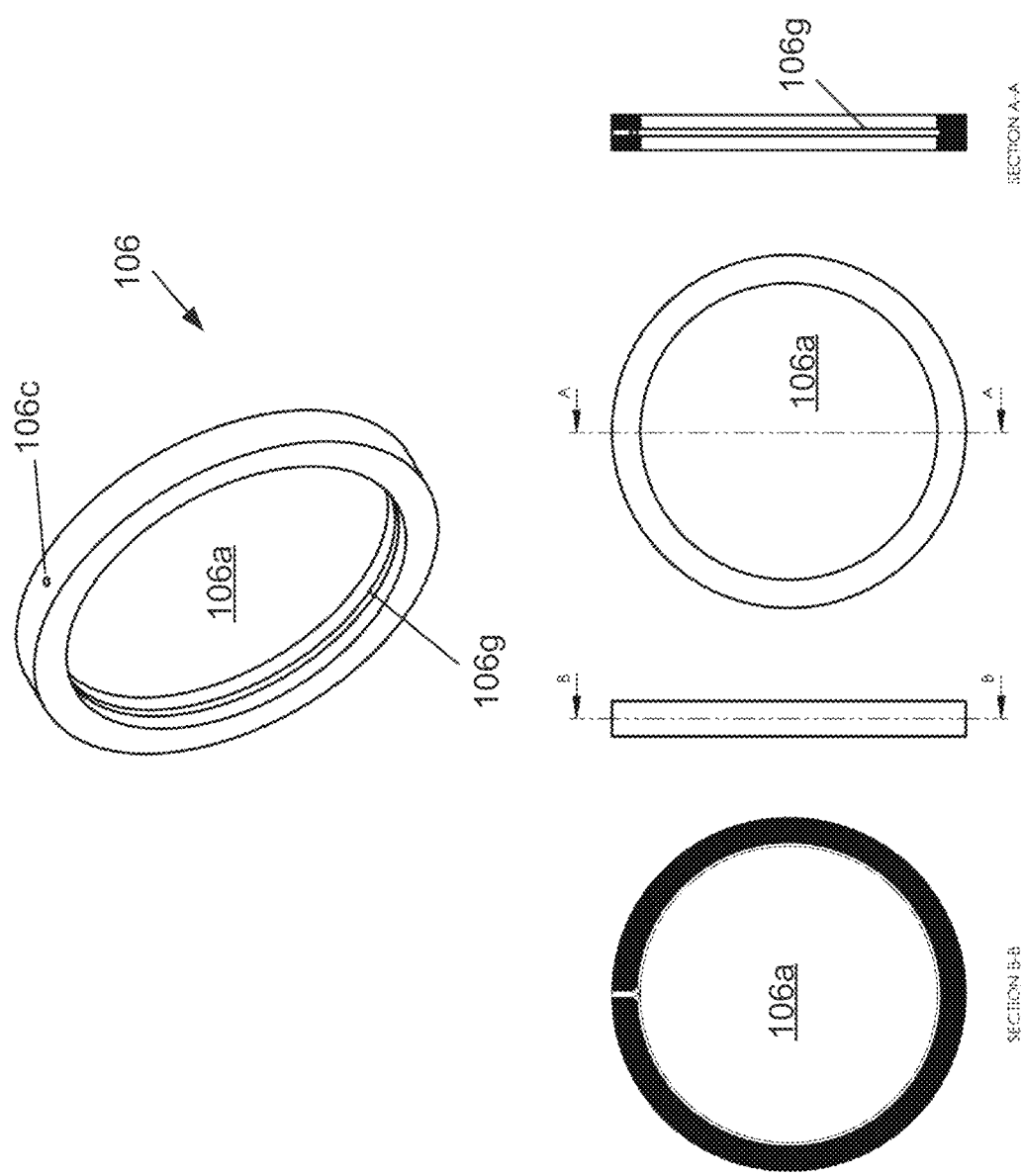
FIG. 4C is a collection of views of an example embodiment of a non-conductive spacer that can be used in the optical stacks of FIG. 4A or FIG. 4B.

Various views of the non-conductive spacer 106 are shown in FIG. 4C. In the embodiment of FIG. 4C, the non-conductive spacer 106 is a frame that defines a reservoir 106a that can include the electrolyte.

The first electrode 102, and the additional electrodes 124 and 126, are optically transparent in the visible light range when not plated. The electrodes 102, 124 and 126 have deposition sites that can be used to control the level of optical transparency of the device 10. Nanoplating will occur at the deposition sites when certain potential differences are applied to the electrodes 102, 124 and 126. Accordingly, the distribution of the deposition sites in terms of patterns, spacing, and density as well as the pattern, charge, magnitude, and time duration of the applied potential difference dictate the amount of nanoplating that will occur will. Having a specific distribution of current, due to applied charge voltage and resistivity of the pattern of deposition sites, components in the constituents of the electrolyte and deposition sites will allow the nano-plating to be more uniform/smooth, hence creating a more reflective surface. In contrast, having a more irregular distribution of deposition sites, the current and resistance of the deposition sites, and lacking spacer elements or other constituents in the electrolyte which otherwise improve uniformity and smoothness of the nanoplating, can make the nanoplating surface more rough and more likely to absorb light when nanoplated.

The various transparent electrodes described herein can include a conducting substrate that may include deposition sites on a surface of the conducting substrate that faces the electrolyte medium if the conducting substrate is not chemically inert in a given electrolyte medium and electrochemistry is chosen to implement the optically adjustable element. Alternatively, in embodiments in which the substrate of a transparent electrode is inert and not chemically reactive then portions of the substrate have a structure that can also provide deposition sites in a predefined pattern as described herein. For example, in such embodiments, the substrate may include platinum nanowires that also provide deposition sites.

The conducting substrate can include but is not limited to conductive nanowire networks (including platinum nanowires, silver nanowires, gold nanowires, or copper nanowires), Halide Tin Oxides (including Ethylene Oxide (ETO) or Fluorine Doped Tin Oxide (FTO)) and graphene and carbon nanotubes. Some conducting substrates as listed above may need to be coated in an inert substance using techniques such as, but not limited to, electroplating and atomic layer deposition in order to not chemically react with a given electrolyte or a given component in the given electrolyte that is used in the nanoplating embodiments. Deposition sites can be located on the conducting substrate and include covalently linked relatively chemically inert nanoparticles (including but not limited to noble metal nanoparticles such as platinum, rhodium, iridium, palladium) and electroplating with relatively chemically inert noble metals (including but not limited to platinum, rhodium, iridium and palladium, for example).

Under normal daylight conditions, the average user, who is using a device with the optical stacks 100 or 120, will be able to see past the transparent electrode 102, 124 or 126. The user does not see the counter electrode 108, since it is positioned outside the visual axis.

The transparent electrode 102 is generally implemented as a conductive transparent optically adjustable disk disposed in front of the electrolyte medium 105 which exists inside the space encircled by the counter electrode 108 and spacer 106. In other embodiments, which use the electrode 126, the electrode 126 sits behind the electrolyte medium 105 and is isolated electrically from the counter electrode 108 with various possible embodiments including, but not limited to, insulating spacers. In yet other embodiments where the electrode 124 is used, such transparent and porous electrodes, which can be implemented in various ways such as but not limited to nanowire conductive networks, are located within the electrolyte medium 105. The electrolyte medium 105 can be a solution or gel like substance that is viscous such that the position of the electrode 124 is spaced apart and electrically isolated from the counter electrode 108 as well as other transparent electrodes that may be present. In some embodiments, additional insulating spacers may facilitate electrical isolation. In some embodiments there may be multiple electrodes 124 that are located within the electrolyte 105, and that are spaced apart from one another and the counter electrode 108 and are insulated from each other and the counter electrode 108. The one or more electrodes 124 can be electrically insulated from the first transparent electrode 102 and the transparent electrode 126 by various methods including, but not limited to, the use of spacer 106.

Figure 4D:
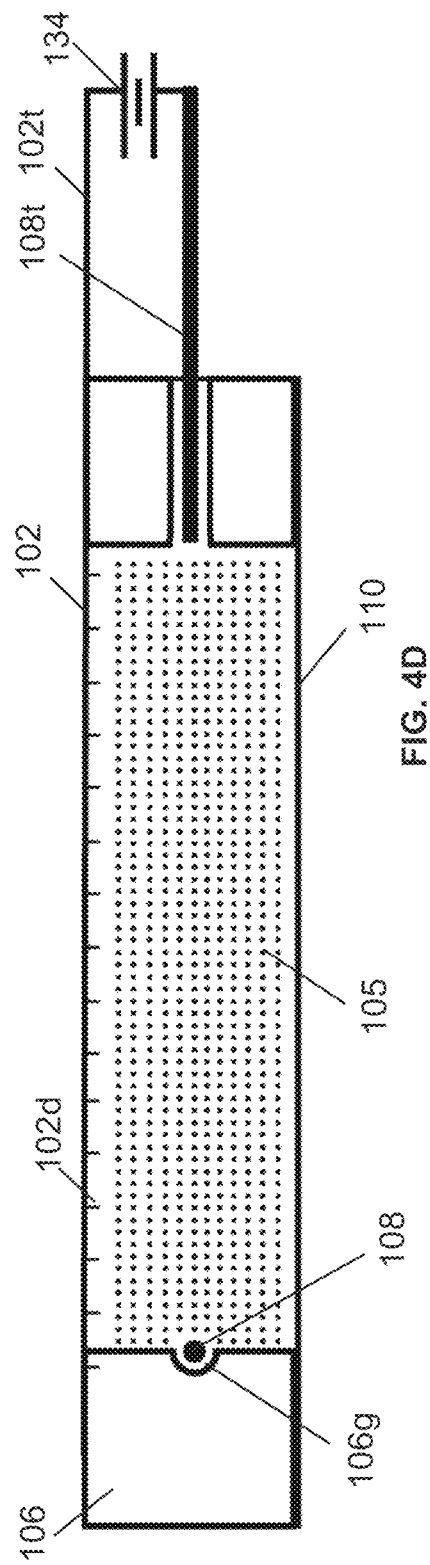
FIG. 4D is a cross-sectional view of the optical stack of FIG. 4A when connected to a voltage source.
Figure 4E:
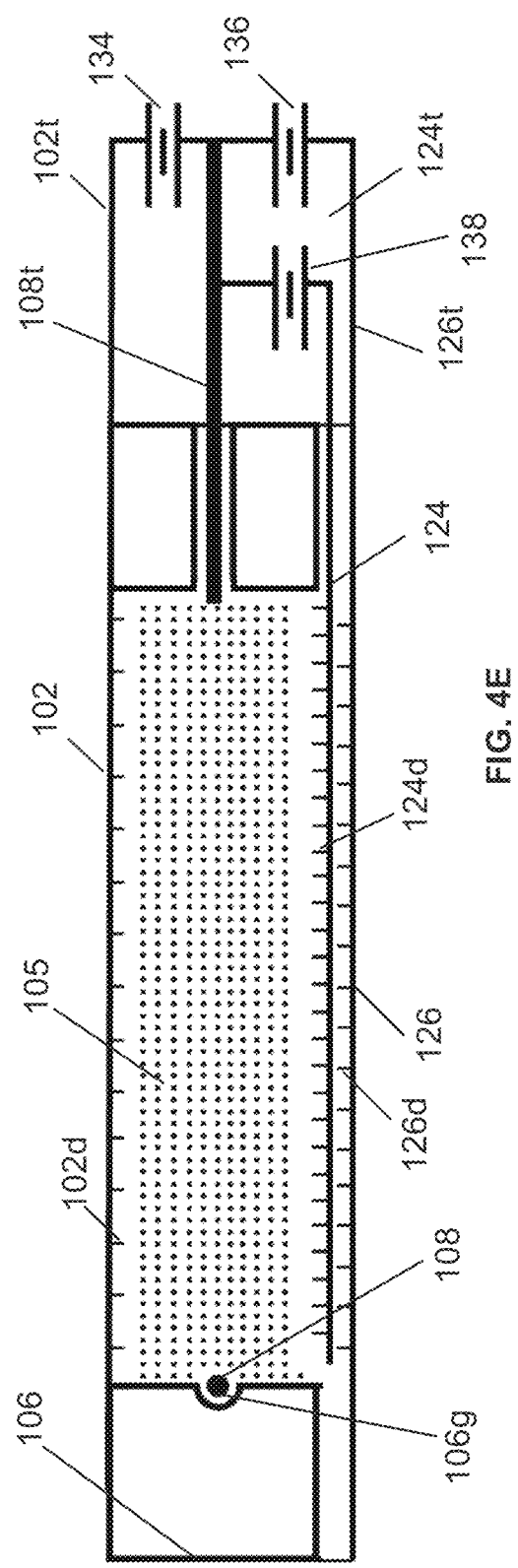
FIG. 4E is a cross-sectional view of the optical stack of FIG. 4B when connected to two voltage sources.

In embodiments including the electrodes 124 and 126, the counter electrode 108 completes the electrical circuit after running through the electrolyte medium 105. For example, when a charge voltage from a voltage source 134, as shown in FIG. 4D for the optical stack 100 and FIG. 4E for the optical stack 120, is applied to electrode 102, electrode 124, or electrode 126 for ion deposition, each circuit runs independently from the transparent electrode 102, 124 or 126 through the electrolyte medium 105 to the at least one counter electrode 108 and nanoscale metal ions are deposited onto at least one of the transparent electrodes 102, 124 or 126 as applicable due to the particular deposition patterns on those transparent electrodes, charge voltage magnitude, polarity, wave pattern and time duration as well as composition of the electrolyte 105. For example, in FIG. 4D, there is a circuit formed by a voltage source 134 electrically coupled to the transparent electrode 102, which in turn is electrically coupled through the electrolyte medium 105 to the counter electrode 108, which in turn is electrically coupled to the voltage source 134. In FIG. 4E, there are additional separate circuits where a first additional circuit is formed by a voltage source 136 that is electrically coupled to the transparent electrode 126, which in turn is electrically coupled through the electrolyte medium 105 to the counter electrode 108, which is electrically coupled to the voltage source 136. A third additional circuit is formed by a voltage source 138 that is electrically coupled to the transparent electrode 124, which in turn is electrically coupled through the electrolyte 105 to the counter electrode 108, which is electrically coupled to the voltage source 138.

In FIG. 4D, one of the deposition sites 102d is labelled on the electrode 102 for ease of illustration, and is not to scale (since they are on the order of nanometers) and the deposition sites 102d can be arranged in patterns other than what is shown in the cross sectional schematic view of FIG. 4D. Likewise, in FIG. 4E, one of the deposition sites 102d (not to scale) is labelled on the electrode 102, one of the deposition sites 124d (not to scale) is labelled on the electrode 124, and one of the deposition sites 126d (not to scale) is labelled on the electrode 126 for ease of illustration. The deposition sites 102d, 124d, and 126d can be arranged in patterns other than what is shown in the cross-sectional schematic view of FIG. 4E, and are not drawn to scale as they are on the order of nanometers.

It should be understood herein that when it is described that a charge voltage is being applied to a particular electrode, this means that the charge voltage is applied to that element such that there is a potential difference between that element and the counter electrode, or another electrode as the case may be at a specific polarity, magnitude, duration, and pattern.

In some embodiments, there can exist an additional reservoir of electrolyte located outside of the visual axis (e.g. within a cavity of the spacer 106), in fluid communication with the electrolyte medium 105 already inside the central space of the spacer 106 and counter electrode 108, that allows for the storage of a larger volume of electrolyte to increase the number of ions available for nanoplating, which can allow for faster nanoplating action if desired or necessary.

The deposition of nanoscale metal ions, when achieved uniformly throughout the transparent electrodes 102 for the optical stack 100 and electrodes 102, 124, and 126 for the optical stack 120, progressively decreases the transparency of the portion of these electrodes being nanoplated, by having nanoplated metal reflect and absorb incoming electromagnetic energy (which includes light). It should be noted that the term "light" is being used for simplicity of illustration in the following discussion, however the term "light" in this context is meant to include other forms of electromagnetic energy beyond visible light, including but not limited to UV radiation and infrared radiation. The nanoplated metal can include metal ions which are attracted to the deposition sites on the electrodes 102, 124 and 126. The deposition sites can have certain predefined patterns to achieve certain changes in optical properties for the optical stacks 100 and 120. For example, the transparent electrodes 102, 124 and 126 can be either constructed or seeded to have specific deposition patterns, such that the incoming light can be more finely modulated.

In some embodiments, by increasing branching in the deposition sites, there is less reflection and more of the incoming light is absorbed, and thus the nanoplated electrode can appear more black.

Alternatively, in some embodiments, when the deposition sites are more uniform on a microscopic level and more uniform plating is encouraged, the more uniformly deposited nanoplated metal can reflect more light and the appearance of the nanoplated electrode more closely reflects the incident light source. More uniform plating can be encouraged by, for example, the constituents of the electrolyte 105 (such as using spacers and levelers in the electrolyte, which can encourage a more uniform nanoplated surface), the substrate (a smoother substrate encourages a more uniform transparent electrode and therefore a smoother and more uniform nanoplated surface) and/or the pattern, magnitude, duration, and polarity of the applied charge voltage.

Alternatively, in some embodiments, the deposition sites can be seeded and arranged to form micro-gates that limit the transmission of electromagnetic radiation therethrough, and have a certain spacing to specifically filter targeted wavelengths of light, so that the targeted wavelengths of light are filtered when the correct amount of nanoplating occurs on the nanoplated electrodes, which is determined by the pattern, magnitude, duration, and polarity of the charge voltage, the substrate, and the composition of the electrolyte 105. Alternatively, in some embodiments, other patterns of deposition sites can be used to create polarized filters and specific wavelength filters to modulate light when the sites are nanoplated at the specified amount.

In yet another embodiment of the device, the first transparent electrode, for example electrode 102, may be configured to induce vertical polarization when nanoplated in a specific electrolyte in a specific pattern (depending on the type and orientation of the polarization desired), charge magnitude and duration, the second electrode, for example electrode 124, may be configured to induce horizontal polarization when nanoplated, and therefore when both of the electrodes 102 and 124 are nanoplated together, the device is opaque. In such an embodiment, it is possible to switch at least a portion of the device reversibly between at least 4 states, including (a) transparent state (in which both electrodes 102 and 124 are not nanoplated), (b) a first polarization state (linear, circular or elliptical), (c) a second polarization state which may be orthogonal to the first polarization state, and (d) an opaque state if both electrodes 102 and 124 are nanoplated to provide the first and second polarization states simultaneously.

In other embodiments, the factors mentioned above including, but not limited to substrate, charge voltage application, electrolyte and seeding pattern (i.e. predetermined pattern of deposition sites), can be specifically designed to reflect targeted wavelengths of light, thereby resulting in a specific perceived colour when the bionic iris device is observed externally. In some of these embodiments, the perceived colour is created by the nanostructure of the nanoplated electrode, similar to what is commonly referred to as structural colour, which occurs commonly in nature, such as in the color of butterfly wings.

In some embodiments, when an opposite charge voltage (e.g. a positive charge voltage when the initial nanoplating was triggered with a negative charge voltage) is applied to the transparent electrode, the nanoplating is reversed, and therefore the modulating effect of the previously nanoplated transparent electrode is reversed to the maximally transparent state (e.g. via stripping of the electrodes).

Nanoplating can have the advantage of creating a darker opaque state relative to other technologies as described below. It can also do so with faster switching speeds when optimized for speed in comparison to other methods. Nanoplating is inherently faster than most technologies since theoretically it may only require a 20-30 nm plating thickness (e.g. of metal) to create a relatively opaque surface, which compares favorably relative to other technologies which require at least a 100-200 nm thickness to create a relatively opaque surface. It can be optimized further by increasing the ions available for nanoplating in the electrolyte, adding electrodeposition accelerants appropriate for the electrochemistry used (examples for a Cu based system include, but are not limited to 3-mercapto-2-propanesulphonic acid (MPSA) and chloride ions in combination) to the electrolyte, adding leveling agents appropriate for the electrochemistry used (examples for a Cu based system include, but are not limited to bis(3-sulfopropyl) disulfide (SPS), Janus Green B (JGB), polyethylene glycol (PEG) and chlorine ions) to the electrolyte, increasing the reservoir of ions available for nanoplating, increasing the speed of diffusion of ions in the electrolyte (by changing the electrolyte to provide more ions and/or increased ion mobility), and by increasing the availability of counter electrodes and thus decreasing the proximity of the effective counter electrode which supplies and replenishes ions to the electrolyte during nanoplating.

In addition, embodiments may exist where stacks of the elements illustrated in either FIG. 4A and/or FIG. 4B can be combined, in addition to the possibility of multiple floating electrodes 124 within each stack as mentioned above.

In embodiments where nanoplating is used, power can be conserved, since in this embodiment, the electrolyte can be adjusted to allow for nanoplating stability, and therefore transmission stability at any level desired. For example, in a basic embodiment, when a negative charge voltage is applied to a given transparent electrode, metal ions in the electrolyte 105 are deposited onto the deposition sites of that given transparent electrode. Ions are stripped from the counter electrode 108. The metallic electro-deposited ions modulate incoming electromagnetic radiation including reflecting, absorbing, and transmitting the electromagnetic radiation. In the simplest embodiment, when sufficient ions are deposited, they render that portion of the given transparent electrode relatively opaque. Less than 1% transmission of visible electromagnetic radiation can easily be achieved in the simplest relatively opaque state. For comparison, in the simplest embodiment, the relatively transparent state transmits approximately 80% to 90% or greater of visible electromagnetic radiation depending on the quality of the substrate used for the given transparent electrode and the type of transparent electrode used. In the simplest central aperture application of the nanoplating embodiments where the pattern of deposition sites has a central zone without deposition sites, a resulting small aperture is achieved, as described above. In this application, when a larger aperture is required, a predetermined charge voltage is applied for a predetermined time to the given transparent electrode such that the nanoplating process is reversed. This results in the electro-deposited ions being stripped from the given transparent electrode and returning back into the electrolyte. Ions are then electrodeposited on the counter electrode 108. The magnitude, pattern, polarity and duration of the charge voltage applied for any given electrolyte, electrode and counter electrode can be used to control the degree of nanoplating/electro-deposition, which impacts the transparency of the device, the speed of transition, as well as the cycling durability.

In many nanoplating embodiments of the device, the electrolyte 105 is tuned such that the equilibrium of the chemical reaction that leads to nanoplating or reverse nanoplating is such that the various states and degrees of nanoplating between maximal relative transparency and maximum relative opacity as described above, are stable and therefore do not require any ongoing charge voltage to maintain a specific state or degree of nanoplating. As mentioned, this is important for conserving the energy that is used. In these embodiments, the charge voltage is only applied for changes in state from one level of opaqueness/transparency to another. No charge voltages are applied for the maintenance of any given state, which advantageously improves energy conservation. For example, when 50% light transmission or transparency is desired in a given transparent electrode, charge voltage can be applied to achieve the 50% transparency. After this, no voltage needs to be applied, and the given transparent electrode will remain nanoplated and at the 50% light transmission level until further charge voltage is applied. The same can be achieved for any light transmission level including, but not limited to 10%, 25%, 40%, 60% and 70%. Similarly, when 1% light transmission is desired, charge voltage can be applied to the given transparent electrode to reach the 1% light transmission and then the device remains at 1% for a significant period of time.

For example, in some embodiments, if the voltage source were to be disconnected, the given transparent electrode and the stack will remain at the 1% light transmission level for hours, days, weeks, months, years and sometimes longer since the electrolyte is tuned such that the chemical reaction leading to nanoplating neither favors deposition nor favors stripping when no potential charge voltage is applied across the given transparent electrode and the counter electrode. This property again can apply to any level of transparency from maximum relative transparency to maximum relative opacity.

Figure 5B:
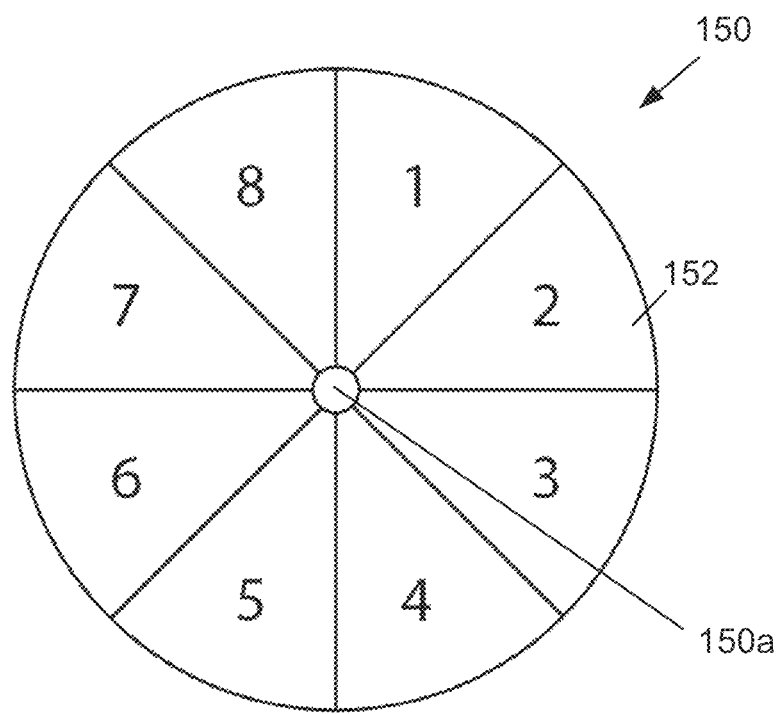
FIG. 5B is an example embodiment of an electrode that can be used with the optical stack of FIG. 4A or FIG. 4B.
Figure 5C:
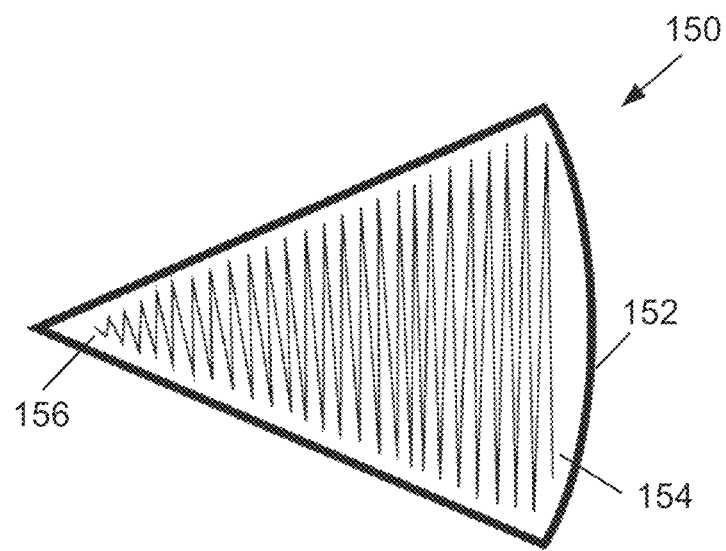
FIG. 5C is an example embodiment of an electrode portion for the electrode of FIG. 5B.
Figure 5D:
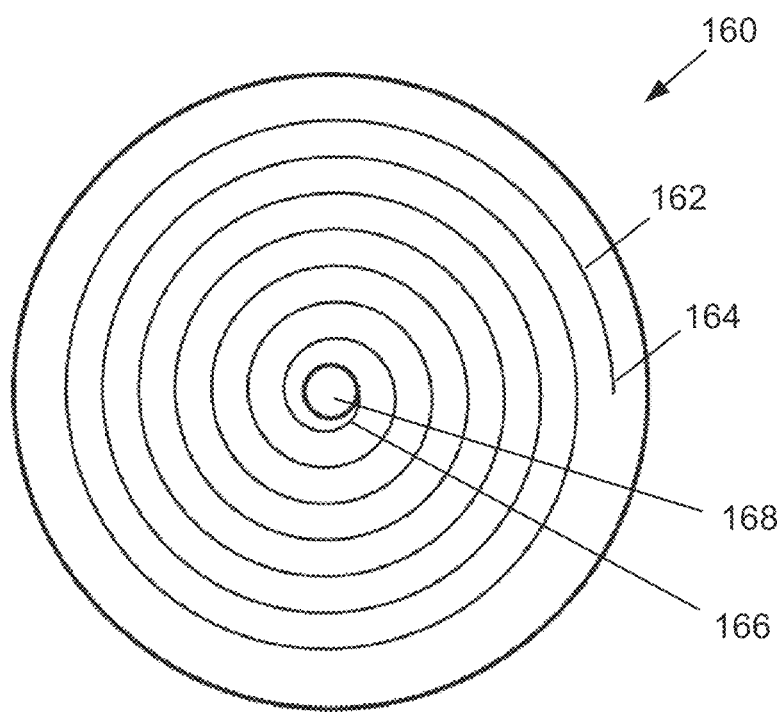
FIG. 5D is another example embodiment of an electrode that can be used with the optical stack of FIG. 4A or FIG. 4B.

Even with a simple embodiment of nanoplating such as with a transparent electrode modeled after FIG. 5D, a variable sized aperture may be achieved by having deposition sites on the given transparent electrode that have increased resistivity closer to the center in a spiral pattern. In this manifestation, the greater the pattern of the magnitude and duration of the charge voltage, the more central that the deposition will occur on the spiral and thus the smaller the resulting aperture. In a further alternative embodiment, a different specially designed electrolyte can be used that slowly strips the metal from the given transparent electrode, instead of a balanced equilibrium chemical reaction based on an electrolyte as described above, such that the aperture gets larger with time when no charge voltage is applied to the given transparent electrode. Furthermore, in embodiments where a power source that is responsive to light such as a photovoltaic cell is used to supply power for the applied charge voltage requirements, the aperture may be tuned to decrease in size since the electro-deposition becomes more central when the charge voltage is applied with a larger magnitude and/or for a longer time to the given transparent electrode. In this embodiment, with more light, there is an increase in size of the nanoplated area. When there is less light, the specially tuned electrolyte will strip the deposited metal resulting in a smaller nanoplated area centrally and a larger sized aperture. When there is no light and thus no charge applied via the photovoltaic cell, then even the peripheral ring area of the nanoplating does not occur actively, and in this specially tuned electrolyte, all the nanoplating is stripped away from the given transparent electrode and the aperture is at the maximally opened size. This relationship can be modulated by various algorithms controlling the various components, power sources, light sensors, task sensors, controllers, timers, and electrolyte compositions to achieve the desired relationship of light to aperture size. Similarly, if a rangefinder is attached to trigger the supply of voltage, the aperture size in such a setup may be controlled by the distance of an object to the aperture.

Similar to the above embodiment with one relatively stable state, in some embodiments, the stable state equilibrium can instead be adjusted to be a relatively opaque state and the active state can be a relatively transparent state. In other embodiments, the stable state can be a relatively transparent state and the activated state is a relatively opaque state. In yet another embodiment, the stable state can be a state anywhere between relative opacity and relative transparency, with the activated state being either more opaque or more transparent or anything in between by setting the equilibrium of the chemical reaction that leads to nanoplating or reverse nanoplating accordingly.

Referring again to FIG. 1, the membrane 20 forms a hermetic seal around the components of the device 10 in order to protect these components as well as to protect the eye in which the device 10 is implanted. The membrane 20 is thin and transparent and is made of inert, clear, and flexible material such as, but not limited to, silicone, acrylic, polymer, barrier, or a collamer material, all of which are generally optically transparent. For instance, the optically transparent silicone that is used for intraocular lenses may be used to implement the membrane 20. Alternatively, when acrylic material is used to implement the membrane 20, the acrylic material may be hydrophobic or alternatively the acrylic material may be transparent, hydrophilic, and may or may not have a hermetically sealed hydrophobic surface coating. In another alternative, when a collamer material is used to make the membrane 20, the collamer material may be hermetically sealed with a hydrophobic coating. In another embodiment, the elements of the device 10 may be grouped into two or more portions, each of which is completely hermetically encapsulated. The membrane 20 is formed of a biocompatible material, and in some examples, all of the internal components within the membrane 20, including, for example, the electrolyte, can also be biocompatible (e.g. the electrolyte can have a neutral pH, and all components can be non-toxic). This may help improve safety of the device, for example, in case of an unexpected failure of the membrane 20. In some examples, the device is free of ferromagnetic materials, which may allow for individuals with the implanted device to proceed with magnetic resonance imaging (MRI) scans.

The haptics 22a and 22b are coupled to the peripheral edges of the device 10. The haptics 22a and 22b are flexible, have an arc or a curved shape and function structurally to center the device 10 within the user's eye. The elastic properties of materials used to implement the haptics 22a and 22b cause the haptics 22a and 22b to act as opposing springs to center the device 10 when implanted in the user's eye. The haptics 22a and 22b can be attached to either the substrate 18 or another suitable component of the device 10. The haptics 22a and 22b may also be made using materials that are conductive or non-conductive.

In some embodiments where the haptics 22a and 22b are constructed of a biocompatible material, they can be disposed outside of the membrane 20. In some embodiments, haptics 22*a* and 22*b* will extend from the main body (i.e. optic portion) of the device 10 to a total diameter of 13-15 mm depending on the size of the eye and the planned position of the device 10. In some embodiments, the device 10 may be physically large enough relative to the eye so that the haptics 22*a* and 22*b* can have a much smaller size.

Figure 3A:
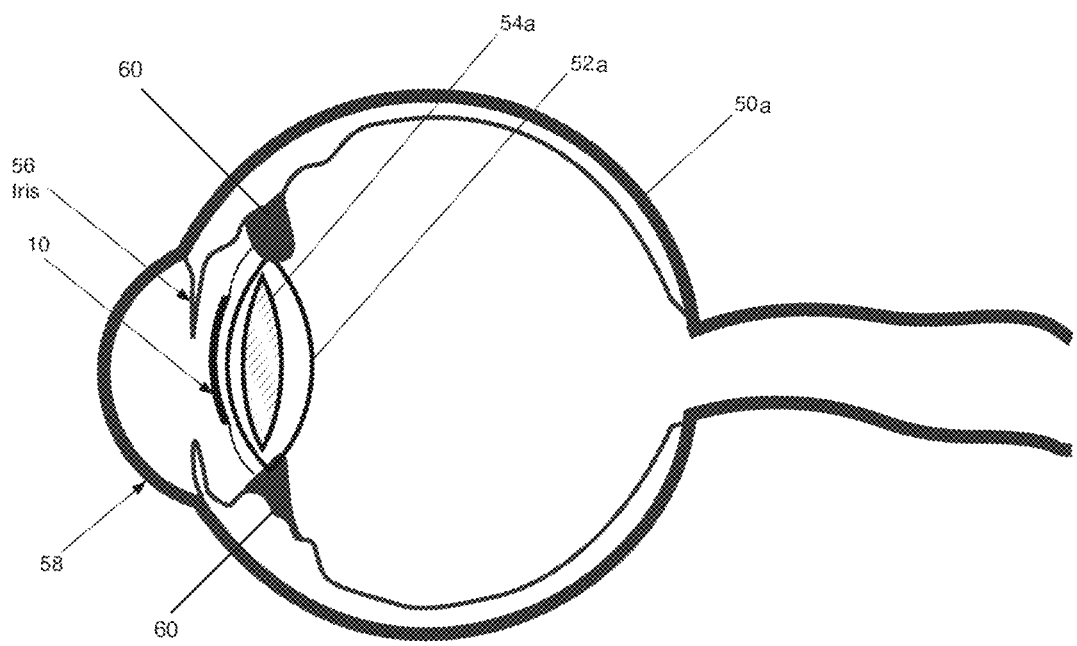
FIGS. 3A-3D show various implantation locations in different eyes for the intraocular prosthesis systems of FIGS. 1A-1C.
Figure 3B:
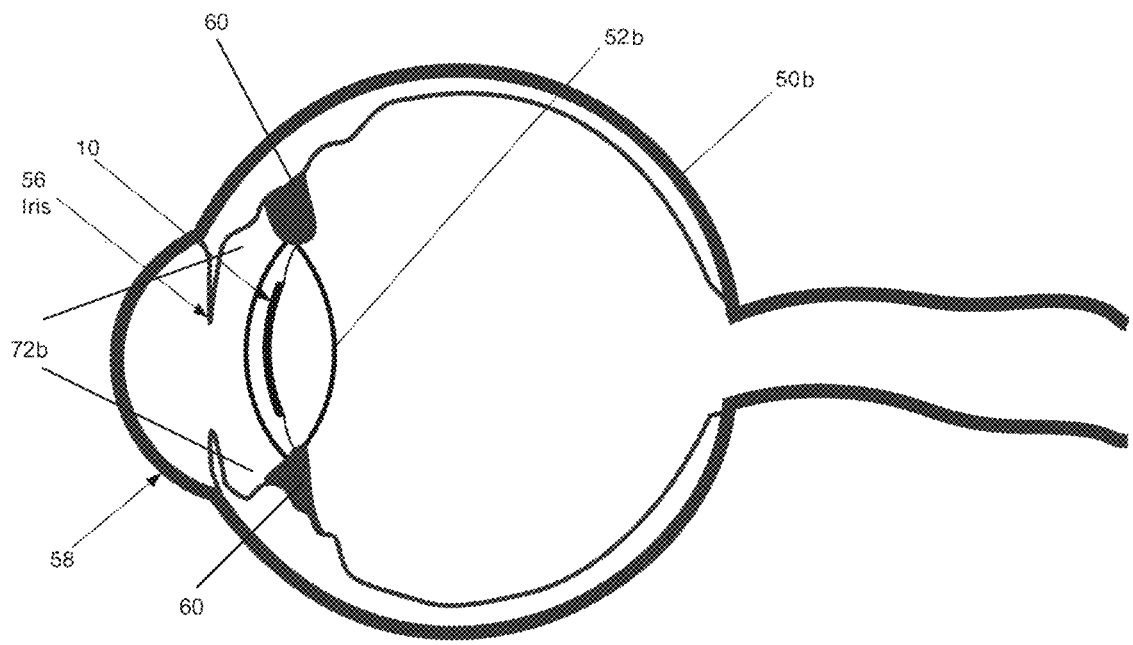
Figure 3C:
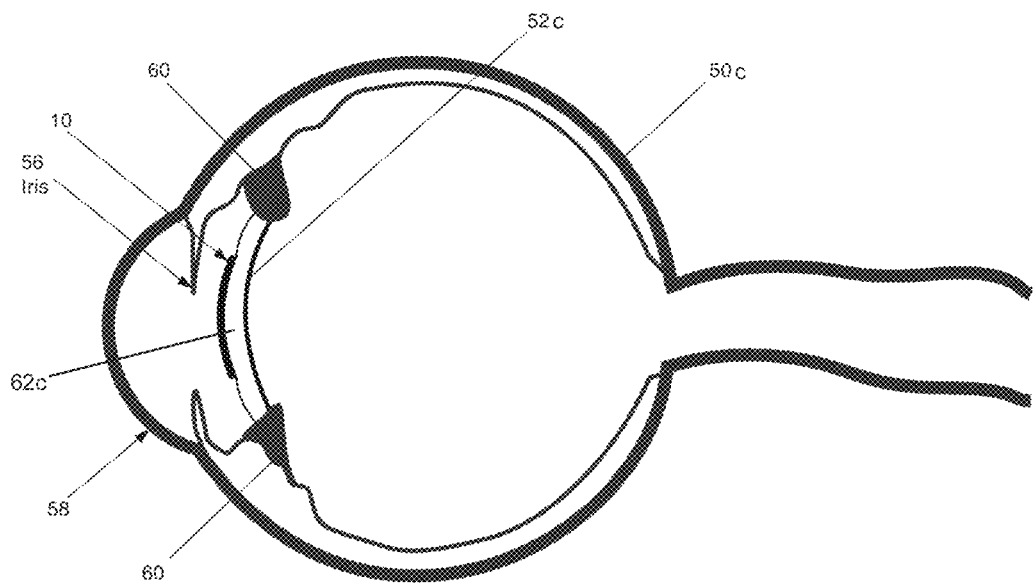
Figure 3D:
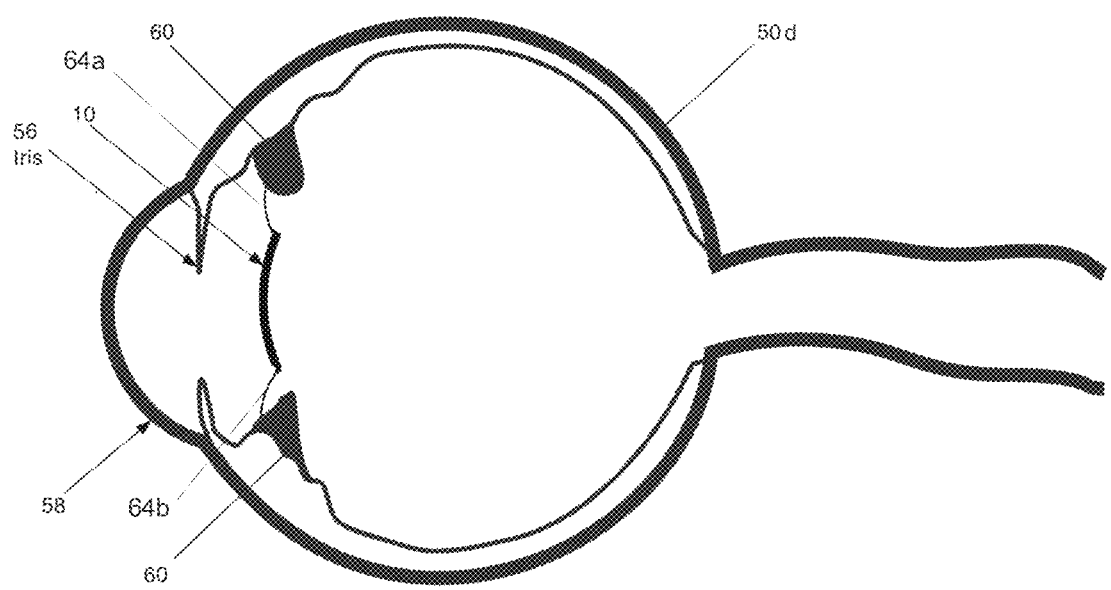

Alternatively, some devices may not use haptics 22*a* and 22*b*, such as device 10' shown in FIG. 1C, although even devices shaped such as device 10' may benefit from smaller versions of the haptics 22*a* and 22*b* in some embodiments. In other embodiments, devices such as those shown in FIGS. 1C and 1D can also include haptics similar to the haptics 22*a* and 22*b* shown in FIGS. 1A and 1B, to facilitate centering of the device in the eye, such as when the devices are to be implanted as shown in FIGS. 3A, 3C, or 3D. In some embodiments, such haptics may not be required when the device is to be implanted as shown in FIG. 3B.

In some embodiments, the haptics 22*a* and 22*b* can contain sensors to detect electrical activity, including, but not limited to muscle contraction of the ciliary body, the electrical activity of the retina, brain, nerves and surrounding musculature. In some embodiments, these signals, either isolated or analyzed in combination, help to detect accommodation convergence and/or help to predict the intent of the user for specific visual tasks and otherwise (and in some examples can be used to help control device components as described herein).

In some embodiments, the haptics 22*a* and 22*b* contain piezoelectric actuators that can either or both sense motion, directly or indirectly from the ciliary body and the movement of the eye or components within the eye and/or generate or help to generate a portion of the power for the device 10. In these embodiments, the motion sensed by the piezoelectric actuators, of which there may be more than 1 in at least 1 direction, can be used to help detect and predict accommodation convergence and the intent of the user for visual tasks and otherwise.

The controller 28 is used to control the operation of the device 10. The controller 28 may include one or more microprocessors. The controller 28 may include an integrated circuit such as an Application Specific Integrated Circuit (ASIC). In some embodiments the controller 28 is not used and is not necessary. For example, if the wireless (for example induced resonance or radio-wave based) power source is directly linked to the optical element, then no on-board controller is necessary, since the device can be controlled simply by controlling the external source of wireless power. In embodiments which include the controller 28, the controller 28 can control the timing, duration, polarity and magnitude of the charge voltage applied to one or more electrodes. In some embodiments the controller 28 contains a transmitter chip that is responsible for communications. In other embodiments, this transmitter chip is separate (not shown). In other embodiments, a different controller can be used to control sensors as described below on the device. In other embodiments, a different controller can be used to control drug release from the device 10 as described below. In yet other embodiments, the controller controls the transmission of data collected from the sensors located on the device as described below. In other embodiments, when sensors, such as the haptics comprising transducers, detect ciliary body contraction either directly or with the use of a specific algorithm, the controller will adjust the optically adjustable element accordingly. In other embodiments, a controller compiles data from at least one of including but not limited to sensors, actuators, and photodiodes and computes a likelihood and intent of the user and activates the optical element when effort for accommodation or convergence is detected as being the likely intent or is predicted by the transducer haptics independently or in combination with other methods. In yet other embodiments, the controller 28 can learn and refine algorithms for likelihood of detecting effort for accommodation or visual task specificity. In some of these embodiments, the algorithm is a combination or result of neural network training. In yet other embodiments, the controller 28 activates the optically adjustable element based on sensor input such as, but not limited to, a range finder, a light sensor, a luminance, light intensity sensor and external communications detected by the effective antenna. In yet other embodiments, the controller 28 is able to control the optically adjustable element in such a way that it is able to communicate information to the user utilizing the optical element of the device.

The energy storage element 26 can include, but is not limited to, one or more capacitors that are used to collect energy that can be used to power the device 10. In some embodiments, the capacitor discharges to power the certain elements of the device 10 when sufficient charge is accumulated. In other embodiments, the capacitor can also power the controller 28. In yet other embodiments, the capacitor may also power the sensors. In yet another embodiment, the capacitor may power the mechanism allowing for drug release. In some embodiments, energy can be collected for storage such as with a rechargeable battery located with or without a capacitor in the storage element 26. In some embodiments, a fuel cell is located in storage element 26. In other embodiments, the storage element 26 contains a device for collecting and storing kinetic energy. In yet another embodiment, the storage element 26 stores charge from a solar cell. In yet another embodiment, the storage element 26 stores charge from piezo-electric devices. In yet another embodiment, the storage element 26 stores energy from a device that harnesses caloric energy. In another embodiment, the storage element stores charge from the metabolism of organic molecules including but not limited to glucose, which is present in the anterior chamber environment. In another embodiment, the storage element may contain a device for storing energy from an induction device or other wireless power charging mechanism.

In some embodiments, the antenna 16 can be one or more inductive coils that are disposed on or within the protective membrane 20 for transmitting and/or receiving wireless signals and energy that are used for at least one of receiving power (e.g. electromagnetic induction), receiving control signals and sending and/or receiving data. For example, in some embodiments, the antenna 16 may be used to provide power to charge the energy storage element 26. In some embodiments, the antenna 16 may cover a larger area and overlap, but be insulated from the haptics 22*a* and 22*b* if they are made of a conductive material.

In some embodiments, the device 10 may further comprise a communication chip 24 that is coupled to the controller 28 and configured to send information from the controller 28 to an external system. For example, the information that is sent may be data that is measured by one or more sensors included in the device 10. The communication chip 24 may be a Bluetooth low energy chip, for example. In some embodiments, the device 10 does not include the communication chip 24 and the controller 28 can implement the functionality of the communication chip 24.

In some embodiments, the device 10 may further comprise a memory chip (not shown) that is coupled to the controller 28 and configured to store the measured data from the sensor with a time stamp in order to reduce the frequency of communication between the bionic iris device 10 and the external system, therefore reducing power consumption. For example, rather than send the sensed data every time it is measured, e.g. every 100 ms, the sensed data can be measured and stored for 10 seconds and then transmitted when communication is established with an external device, which reduces the number of transmissions. In some embodiments, the memory chip is included inside the controller 28 or communication module 24 for example. In some embodiments, the memory element may be part of an ASIC chip.

The upgrade interface module 30 may be used to allow for future hardware upgrades for the device 10. Accordingly, the upgrade interface module 30 comprises connectors that can receive a component for an upgrade of the device 10. In some embodiments, the upgrade process may comprise opening (e.g. removing) a region of sealed material of the membrane 20 above the upgrade interface module 30 (by using a laser or by mechanical methods), connecting a new component to the upgrade interface module 30 and attaching the new component on the substrate 18, and then re-sealing the region of the membrane 20 with new sealing material at the time of the surgery. In other embodiments, a close proximity of the upgrade module to 30 is all that is necessary without the need to open the sealed membrane 20.

The upgrade can be for the addition of one or more of the following, including, but not limited to: at least one alternate power source, at least one supercapacitor, at least one integrated circuit, at least one sensor, at least one actuator, at least one photodiode, at least one battery, at least one piezo-electric element, at least one RF energy harvester, at least one metamaterial RF energy harvester for charging by long range wireless signals, at least one lens, at least one autofocusing rangefinder, at least one projection device, at least one spectrometer, and at least one signal generator or for repurposing of a redundant induction coil to function as an antenna for a different signal for example.

For example, the upgrade interface module 30 may also be used for adding an upgrade antenna in cases where the induction coil used for the antenna 16 is not sufficient to provide for new antenna functions as technology progresses in the future. In another embodiment, the upgrade interface module 30 can be used to add a sensor that can use the antenna 16 as an outgoing antenna as well as an incoming antenna under the control of the controller 28 or with an additional IC chip (not shown).

In some embodiments where a new upgrade to the device makes one or more previous components unnecessary, the wiring of the device can be designed such that the coupling of certain components can be accessed through the upgrade interface module 30 so that these components can be severed or isolated, for example with a focused laser. For instance, the upgrade interface module 30 can be used to decouple the antenna 16 from the energy storage element 26 (i.e. a capacitor), and a method to perform this can involve directing the energy of a focused external laser source for example, to a specifically designed for laser energy connection in the circuitry between the antenna 16 and the capacitor to sever the connection physically.

In some embodiments, such as in FIGS. 1A-1C, the electric circuitry components are generally arranged so that they are disposed outside the optically adjustable element 13 when the effective aperture is at its largest diameter. For example, this may be in an annular zone that begins at the smallest dimension at a diameter of approximately 6 millimeters, for example, to the close to the outside dimensions of the device 10 which might vary from a diameter of about 6.0 mm to 8.0 mm or even larger to 10 mm in some embodiments. However, in other embodiments, this central area may be up to a diameter of 15 mm centered on the center of the device 10. In some embodiments, such as in the optical stacks 100 and 120 of FIGS. 4A-4D, some of the electrical circuitry components form part of the optically adjustable element 13.

In one embodiment, charge is passed to the device 10 by induction via the induction coil of the antenna 16 which can either be directly passed on to one of the electrodes in some embodiments, and/or connected to the energy storage element 26 in other embodiments, which may include a capacitor with or without a battery, for example. In some embodiments with a capacitor, when a given threshold is reached, the charge from the capacitor is then released to the electrodes including, but not limited to electrode 12, for the device 10 in FIG. 1, or to at least one of electrodes 102, 124, 126 and 108 for devices 100 and 120 in FIGS. 4A-4D depending on the optical effect that is desired. In some embodiments, the charge can be reversed with the correct pattern, magnitude and duration, to reverse the function of the optic film, for example when nanoplating is used in an embodiment, by creating the necessary changes in the magnetic flux used to induce charge in concert with the specific circuitry that can be used to reverse the charge voltage, and adjust its magnitude, pattern and duration. In other embodiments, the charge released can be reversed by changes initiated from the control module 28 with the specific threshold or communication from an external device.

In yet other embodiments, more than one antenna and/or induction coils may be used. This may include, but is not limited to, using more than one induction coil, each optimized for different frequencies, and or patterns of magnetic flux, and each either directly connected to the optical element or a portion thereof, or connected and controlled through the controller 28 to execute, based on an algorithm, a specific signal pattern, magnitude, duration and charge voltage to achieve the desired state in the optical element. For example, in an embodiment with a nanoplating dependent optical element, a specific pattern of deposition sites, and a magnitude, duration and amount of charge may be used to achieve a specific pupil size in a continuous variable pupil sized device based on using a pattern of deposition sites that have increased resistivity centrally an example of which is shown in FIG. 5D. A specific set of the above parameters can be used to achieve a 3 mm pupil for example or a 4 mm pupil. The various parameters of a specific pattern of deposition sites, and a magnitude, duration and amount of charge can be determined through testing and that can be encoded in a control algorithm to control the variable sized pupil.

In an alternative embodiment, the center 11 of the optically adjustable element 13 can be shifted. This may be done to change the user's visual perspective or optimize incoming light from a specific direction, for example. There are multiple ways to achieve this. For example, in a nanoplating embodiment, overlapping portions of the transparent electrodes 124, and/or 126 can be arranged so that their centers are offset from one another in the same optical stack. This may be implemented by positioning or using deposition patterns on the electrodes 124 and 126 so they provide differently positioned eccentric optical apertures. These electrodes 124 and 126 can then be used to create a combined pattern that allows for the effective shift of the center 11 of the optically adjustable element 13 when these electrodes 124 and 126 are selectively nanoplated by selectively applying charge voltages to these electrodes. In another embodiment, at least two optical stacks can be used where each optical stack provides a different optically active zone and pupil 11, such as at least one eccentric optical zone to achieve a similar optical effect.

By changing the size of the optically transparent portion of the optically adjustable element 13, and therefore the effective pupil size, the device 10, and the alternative embodiments thereof described herein, can replace the functionality of a real in vivo iris diaphragm. Therefore, the device 10 can be used to replace an iris in a patient with an eye that either has a defective, damaged or absent iris, either from a congenital defect, trauma or some other cause.

During use, in some embodiments, such as with a nanoplating embodiment, different charge voltages can be applied to the transparent electrode 102 in a circuit that runs through the electrolyte 105 to the counter electrode 108, and vice versa, to alter the amount of nanoplating on the transparent electrode 102 and therefore effect the optical behavior of the optical stack 100. An example of this is optical state 112 shown FIG. 4A.

In a more complex embodiment, such as device 120, with more transparent electrodes 124 and 216 in the same optical stack, each electrode 102, 124 and 126 can be provided with separate charge voltages so that they are controlled separately and independently and set up a potential difference separately between each of the electrodes 102, 124 and 126 and the counter electrode 108 to achieve different optical states, such as optical states 128, 130 and 132 shown in FIG. 4B.

When the electrodes 102, 124 and 126 that have been previously activated and nanoplated to achieve a desired optical state, a different charge voltage of specific polarity, pattern (i.e. signal waveform), magnitude and duration, for example, can be provided to at least one or more of the transparent electrodes 102, 124 or 126 through the electrolyte with respect to the counter electrode 108, so that the degree of nanoplating can be reversed in each transparent electrode 102, 124 or 126 that receives the positive charge voltage, to cause the reflectance and absorbance of the optically adjustable element 13 to be at a maximal level of transparency to provide an optically adjustable element 13 that appears as transparent as possible (see FIG. 2A). This allows a maximal amount of incoming light to pass to the interior of the user's eye. This is beneficial in low light conditions such as at night or in a dark room.

When the effective optical zone aperture is desired to be smaller in this nanoplating embodiment of device 120, a specific negative charge voltage for example, can be provided to at least one or more of the transparent electrodes 102, 124 or 126 (they can be applied independently to allow for the greatest degrees of freedom) through the electrolyte 105 to the counter electrode 108, so that they cause the affected transparent electrodes to nanoplate to the desired degree and therefore affect the reflectance or absorbance of the optically adjustable element to be near maximal levels to provide an optically adjustable element 13 that appears maximally opaque (see FIG. 2B) with a small functional optical aperture. This allows a minimal amount of incoming light to pass into the interior of the user's eye. This is beneficial in very high lighting conditions such as during a bright sunny day or in a very brightly lit room. In an embodiment where nanoplating is used, the desired transparent electrode is nanoplated to the desired degree to achieve this.

In a slightly more complex embodiment, as in device 120 shown in FIG. 4B, different charge voltages can be provided to transparent electrodes 12, 102, 124 and 126 independently, so that they can result in selective changes in the reflectance or the absorbance of the optically adjustable element 13 to, for example, result in only a portion of the optical zone becoming opaque or remaining transparent or any level between transparency and opacity. For example, the transparent electrode 126 can be either only partially sectioned for coverage of a nasal segment 13*n* (FIG. 2C) of the optically adjustable element 13' and/or have full coverage but only be partially active and available for nanoplating in the nasal segment 13*n* in one embodiment. In such an embodiment, when a specific charge voltage is applied to electrode 126, causing nanoplating, only segment 13*n* will become more opaque, resulting in only the nasal portion of the optically adjustable element being opaque, with the central aperture 13*a* and temporal segment 13*t* remaining maximally transparent. This allows for the device to, for example provide directional information to the user to perhaps either turn into the direction of the opacified segment or turn away from the direction of the opacified segment, which ever code was previously determined and understood to be the case by the user. In such an embodiment, another transparent electrode, for example either electrode 102, an additional floating electrode similar to 124 (not shown) or the electrode 126 might provide switchable coverage for the temporal segment 13*t* (FIG. 2C), so that if a smaller optical zone aperture was desired to create an optical effect such as that shown in FIG. 2B, both electrode 124 covering the segment 13*n* and the additional transparent electrode covering the temporal segment 13*t* has a specific charge voltage that is applied simultaneously to generate the optical effect shown in FIG. 2B.

Likewise, in this embodiment of optical stack 120, if a larger optical zone aperture is desired, a predetermined specific pattern, magnitude and duration of charge voltage is applied to reverse the nanoplating to each electrode and cause both segments 13*n* and 13*t* to become transparent to result in a clear optical zone similar to that shown in FIG. 2A. In an alternative embodiment, the two sections may be an upper semi-circular portion and a lower semi-circular portion (both not shown).

In another embodiment, more electrode sections can be independently controlled such as the 8 electrode segments illustrated in FIG. 5B, where the lines between the electrode segments indicate insulated regions (not drawn to scale). In each of the electrode segments, such as electrode segment 152, there can be a resistive pattern with a changing resistivity so that the current density along the resistive pattern changes more centrally towards the tip of the pie pattern, which affects the amount of nanoplating that occurs on the electrode 152. One example of a resistive pattern for the electrode segment 152 is a triangular pattern in which the resistance progressively increases from a radially peripheral region 154 to a radially central region 156 as is shown in FIG. 5C.

In yet another embodiment, the electrodes 102, 124 and 126 can have deposition patterns that are arranged to provide concentric rings 142, 144 or 146 with each transparent electrode 102, 124 or 126 being selectively nanoplated, when provided with a specific parameter (including, but not limited to magnitude, duration and pattern) and charge voltage alone or in combination, to result in a variable pupil size as shown in FIG. 5A. In this diagram, the portion indicated with 148 represents 4 leads from electrodes 102, 124, 126 and 108 that have the same vertical and only the front lead can be seen. This embodiment allows for discrete variable pupil/optical zone aperture sizes.

In yet another embodiment, the resistance through one transparent electrode, such as electrode 102, 124 or 126 is gradually increased in a spiral pattern an example of which is shown for electrode 160 having resistive spiral pattern 162 (it should be noted that the coils are on the micro and/or nano-scale and are not shown to scale) in FIG. 5D. The resistivity of the spiral pattern 162 is selected such that the portions 166 of the pattern 162 closer to the center of the aperture 168, have a higher electrical resistance than portions 164 of the spiral pattern near the periphery of the electrode 160. In such an embodiment that employs a nanoplating embodiment, a more analog adjustment of pupil or optical zone aperture size based on the deposition pattern, and the magnitude, duration and polarity of a charge voltage that is applied to the electrode 160 can be selected, such that in general, a higher specific charge voltage with other parameters that follow a previously defined algorithm described above, for example, which may be determined through experimentation, results in a smaller pupil and in general a lower charge voltage, for example, results in a larger pupil aperture. Subsequently, a different specific charge voltage at a specific pattern, magnitude and duration for example, then reverses the nano-plating and results in a larger pupil aperture in such an embodiment. Alternatively, in such a spiral increasing resistance embodiment, if the equilibrium of the electrolyte were adjusted to allow for transparency at rest, then simply removing the applied specific charge voltage to the electrode 160, for example, eventually leads to gradual transparency and a larger effective pupil/optical zone aperture size.

In some embodiments, the different sections of the optically adjustable element 13 can be controlled to have a different amount of transmission, absorption, and/or reflectance in order to provide a message or information to the user of the device 10 via an optical signal as will be described in further detail below. The appearance of this visual pattern or a fluctuating visual pattern (such as when rapid nanoplating is applied and reversed), may also be codified to signal special messages such as an urgent call or the occurrence of a specific event. In yet other embodiments, the switching between two given levels of transmission (for example between states of a relative transparency and opacity and/or any degree or level of transparency and opacity between maximal transparency and maximum opacity), absorption and/or reflectance of either a section, more than one section and/or the entire optical element 13 can be codified to communicate more complex information with the user.

In yet another embodiment, the device may include at least two induction coils that are used to provide power to at least one aspect of the optical element, where the at least two induction coils operate at different resonant frequencies. In such embodiments, the induction coils may be located including, but not limited to, concentrically with respect to one another, above or below the optically adjustable element 13 of the device. In one such embodiment, the at least two induction coils need to be activated simultaneously before the optically adjustable element 13 can be provided with a voltage (i.e. a charge voltage in the nanoplating embodiments), therefore decreasing the possibility that the optically adjustable element 13 is powered unintentionally by magnetic flux that might happen to be present at any given time, at one of the resonant frequencies. This provides increased safety since both resonant frequencies need to be transmitted before the optically adjustable element 13 can be activated. In addition, having more than one frequency necessary to activate the aspect of the optical element allows for a proprietary customized charging and signaling system in order to securely, optimally and reliably charge and/or activate the entire device 10. Therefore, generic frequencies cannot be used which provides a barrier to hacking.

In another embodiment of the device 10, non-standard coils may be used so that non-standard charging equipment (i.e. not standard NFC technology) is necessary to power the optical element to improve security for the device. Alternatively, in another embodiment, two different standard coils may be used; however, they are implemented such that they must be induced in a specific order, by a specific pattern of magnetic flux, and at a specific rate according to an activation method that is kept secret, for security purposes, before the optically adjustable element can be powered to be activated.

In other embodiments, standard coils may be used so that, for example, standard NFC enabled devices, such as mobile phones, may be used to activate the device 10 when directed by a specific software application. In such embodiments of the device, a capacitor charges by induction that requires proximity, so that the optically adjustable element 13 can only be activated when the charging induction device coil (of a certain resonance frequency/coil size/material, that is able to be used or re-purposed as an antenna that allows for longer range transmission, such as Bluetooth LE for example) is in very close proximity (5-10 cm) to the surface of the eye. This is another method that improves the security of the device because of the proximity necessary to activate the optically adjustable element 13.

In other embodiments, at least one electrode of the optically adjustable element 13 of the device 10 may be separated to provide 2, 3, 4, 5 or more subsystems that operate in the same general manner examples of which are shown in FIG. 2C, FIG. 5A and FIG. 5B. Separating at least one electrode of the optically adjustable element 13 into more separate elements can be useful in some embodiments since more sophisticated messages can be potentially communicated to the person that uses the device 10 by activating the separated elements separately and in specific pre-determined coded patterns of use and degrees of light energy modulation. For example, the coded pattern may be a Morse code pattern that is applied to specific transparent electrodes in a timed fashion or a physical pattern or an interspersed pattern. For example, with respect to FIG. 5B, the pattern may be to activate the electrodes 1 and 2 to momentarily change their opacity, then activate electrodes 4 and 5 to momentarily change their opacity and so on. Any pattern can be generated with a degree of freedom that depends on how many separately controllable electrodes there are. In addition, if two devices are implanted bilaterally (i.e. one for each of the user's eyes), even more sophisticated messages can be relayed to the user via both devices (in a bilateral fashion) by further increasing the degrees of freedom of expression. For example, this may be done by varying the portions of these devices that are opacified, the coordination between different opacified portions of each device and between both devices (in a bilateral fashion) as well as the dynamic pattern of opacification. In addition, in a bilateral situation, one eye can be optimized primarily for communication, while the other eye can be optimized for performing a specific task.

Referring now to FIGS. 3A-3D, shown therein are various eyes 50a, 50b, 50c, and 50d that generally include an iris 56 or a remnant of portions of a traumatized or congenitally abnormal iris, in different conditions, a cornea 58 and a ciliary body 60. Eyes 50a and 50b also include a lens capsule 52a and 52b, respectively. Eye 50a also has a lens 54. The bionic iris device 10 is implemented so that it can be implanted safely in certain locations in the different eyes

50a, 50b, 50c and 50d. However, the optimal implantation location depends on the pre-operative state of the eye such that the implantation is minimally invasive given the state of the eye. The device 10 is also implemented such that it can be implanted in almost any eye, whether phakic, pseudophakic or aphakic, and with either an intact or a damaged lenticular capsular bag (i.e. lens capsule).

For example, the bionic iris device 10 can be implanted behind the iris 56 and in front of the natural crystalline lens 54 for eye 50a shown in FIG. 3A. The configuration shown in FIG. 3A is for an individual with a normal functioning eye with no evidence of visually significant cataracts. The eye 50a is also representative of an individual with isolated iris defects from trauma or congenital etiologies or one with a non-functional iris such as might occur with traumatic mydriasis or injury or infarct to the pupillary sphincter muscle and/or dilator muscle, or injury to the nerves innervating the described muscles.

In another example, as shown in FIG. 3B, the bionic iris device 10 can be implanted either inside the lens capsule 52b of eye 50b or in the ciliary sulcus 72b at the time of cataract surgery. A slightly larger sizing of the device 10 may be necessary for stable long-term implantation when the device 10 is placed in the ciliary sulcus 72b. For individuals having eye 50b with a cataract that is either senile or perhaps traumatic at the time of iris injury, the device 10 can be implanted in the lens capsule 52b which is typically preserved in modern cataract surgery when it is healthy and intact.

In another example, if the lens capsule 52c is either damaged at the time of injury or it is not intact due to a previous surgery, the device 10 can be implanted in the ciliary sulcus 62c and anterior to any lens capsule remnants as shown in FIG. 3C. The ciliary sulcus 62c is a location that lies behind the iris 56 and in front of the ciliary body 60. If there is enough capsular support, implantation into the ciliary sulcus 62c can be additionally stabilized by optic capture of the central portion of the device 10 within the remaining capsule (i.e. capsular remnants) 64a and 64b as shown in FIG. 3D. In this optic capture positioning of the device 10, the optic is captured within an opening in the capsular bag such as within the capsulotomy either from a capsulorhexis or created by other methods.

In another embodiment, the device 10 can be fashioned such that it can be placed anterior to the eye or with the correct curvature and size such that it could float on the tear film of the eye.

In one example embodiment, to implant the device 10 within one of the eyes 50a, 50b, 50c or 50d, the device 10 can be flexible and rolled into a scroll and inserted through a small corneal incision, such as about 1.1 mm, or 2.2 mm or 2.8 mm, to be unrolled inside the eye 50a, 50b, 50c or 50d. In some examples, the device 10 can be folded about one fold axis (e.g. for a "taco" style fold) or about two or more fold axes (e.g. for a trifold) to facilitate insertion through a corneal incision. Referring to FIG. 1C, the device 10' is shown schematically with one fold axis 27 extending horizontally along a length of the device from a first side to a second side, and about which the device 10' can be folded. In this embodiment, the device 10' is free of any non-flexible components (e.g. chips or other non-flexible circuitry components) positioned on the fold axis 27 to facilitate folding of the device 10' thereabout. The fold axis 27 can facilitate folding the device 10' with a small radius bend at the fold axis of about, for example, 1.5-2.2 mm. The device 10' can have an overall thickness measured between a front face and a rear face of the device 10', and can have a reduced thickness along the fold axis 27 to facilitate folding thereabout. In some examples, when unfolded, the device 10' can have a length of between about 12 mm and 13 mm (and in some examples 12.1 mm), and a width of between 6 mm and 6.5 mm (and in some examples, 6.2 mm). In some examples in which the device includes two fold axes extending along the length and spaced apart along the width (e.g. as shown for the system in FIG. 1D), the device, when folded, can have a folded width of between 2 mm and 2.2 mm, and can fit through an incision having an incision length of, for example, about 2.4 mm.

In some examples, the device 10 can be designed for reduced caloric changes, including but not limited to, heat generation and dissipation. For example, the device can provide increased heat dissipation by the surrounding aqueous circulation through the use of, for example, channels that promote convection flow of the aqueous surrounding the implanted device and help provide increased exterior surface area adjacent heat generating components of the device. In some examples, the channels can be provided by fold axes (e.g. the fold axis shown in FIG. 1C or 1D).

In another example embodiment, the device 10 can be inserted into the eye 50a, 50b, 50c or 50d and a part of the device 10 can be assembled inside the eye 50a, 50b, 50c or 50d. For example, the induction coil of the antenna 16 may be inserted separately into the eye after the main device 10 has been inserted in some embodiments of the device 10 (although both are each hermetically encapsulated in these embodiments), and then attached by a simple mechanism inside the eye 50a, 50b, 50c or 50d. This may be useful to allow for implantation through a smaller incision and to minimize disturbance to the rest of the eye as well as minimize stress to certain components on the device 10 during the manipulation required for implantation.

In another example embodiment, the device 10 can be upgraded (e.g. the addition of improved batteries, improved computing power, improved power induction, or other sensing features can be added) by either exchanging a component of a multi-piece device when the device is implanted in multiple pieces as described above, or simply implanting an additional component that interfaces with the existing implanted device at the upgrade interface module 30. In one embodiment, the upgrade interface module 30 allows the interface of two components through the hermetically sealed encapsulation without the exposure of either component. In another embodiment, this is done by alignment of induction coils in close proximity to one another, and in another embodiment, alignment of pin structures or other positioning structures may be done.

Figure 1D:
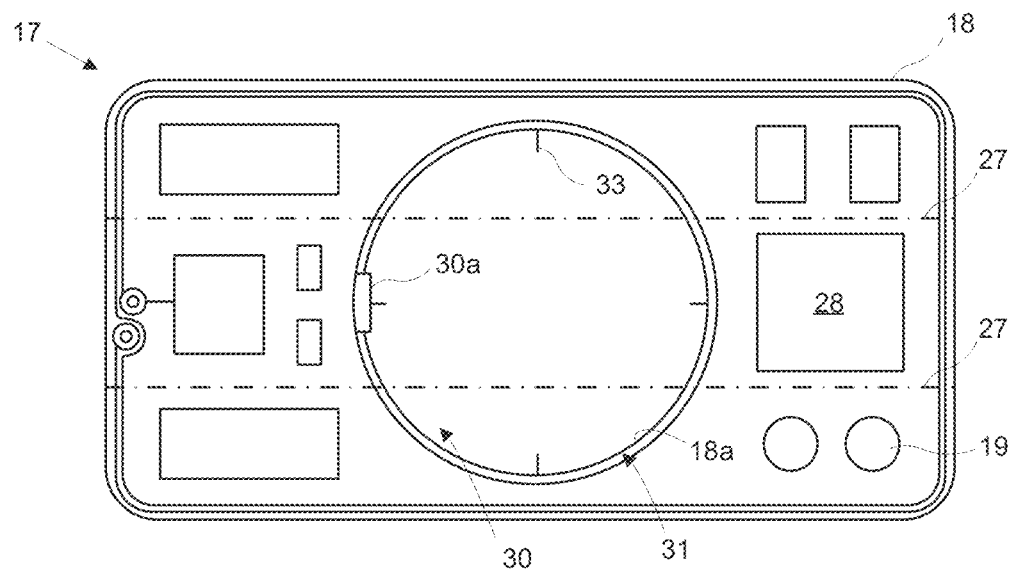
FIG. 1D is a front view of an example intraocular platform system.

Referring to FIG. 1D, an intraocular platform system 17 for the device 10 is illustrated schematically. The platform system 17 includes a substrate 18 implantable in the eye and having an aperture stop 18a defining an aperture for the eye. In the example illustrated, the aperture stop 18a provides a static (fixed) aperture for the eye, and the platform system 17 can be upgraded to incorporate an adjustable optical element (e.g. like those disclosed herein) for varying the aperture size and/or one or more other optical properties for the eye. In the example illustrated, the substrate 18 is flexible to facilitate implantation. In the example illustrated, the platform system 17 can be folded about two laterally spaced apart fold axes 27 (for a trifold) to facilitate insertion through a corneal incision. In this embodiment, the platform system 17 is free of any non-flexible components (e.g. chips or other non-flexible circuitry components) positioned on the fold axes 27 to facilitate folding of the platform 17 thereabout.

The platform 9 further includes at least one coil (e.g. an antenna coil 16) coupled to the substrate and configured to receive wireless signals (e.g. for controlling and/or powering device components). At least one sensor 19 (e.g. like those described in the present disclosure) is coupled to the substrate 18 for monitoring one or more properties of the eye. The platform system 9 further includes an upgrade interface 30 on the substrate 18 for installation of an optical element (e.g. like those disclosed herein) over the aperture stop 18*a*. The optical element can be installed prior to or post implantation of the platform system 17 in the eye. The platform system 9 further includes a controller 28 for communication with the coil to control operation of the platform system 17 (e.g. for sending control and/or power signals to device components). The controller 28 is shown supported by the platform 9 in the example illustrated, but can be external the platform 9 in other examples and configured for wireless communication with platform components.

In the example illustrated, the upgrade interface 30 comprises a recessed area 31 in the substrate 18. In the example illustrated, the recessed area is shaped and positioned to receive the optical element in the aperture defined by the aperture stop 18*a* (e.g. to provide an adjustable aperture stop or vary one or more other optical properties for the eye via the optical element). In the example illustrated the upgrade interface 30 comprises at least one connector 30*a* (e.g. electrical leads or non-electrical connector) for connecting the optical element when received in the recess to, in some embodiments, permit the optical element to receive control and/or power signals from platform components when installed. In other embodiments, the optical element is passive (e.g. the optical element can comprise a static lens). In the example illustrated, the upgrade interface 30 further includes one or more actuators 33 for moving the optical element (when installed) into alignment with a specific visual axis. In the example illustrated, the platform can further include a biocompatible coating (e.g. a coating of silicone) to seal the platform components.

As previously mentioned, there is more than one way to achieve variable opacity for the optically adjustable element 13, other than the use of nanoplating, including the use of charged nanoparticles, liquid crystal display technology or electrochromic reactions. For example, referring now to FIGS. 6A-6C and 7A-7C, shown therein are side and front views, respectively, of a portion of another embodiment of the bionic iris device 10*a* in different states of opacity. In this embodiment the device 10 uses opaque charged nanoparticles. In particular, FIGS. 6A-6C and 7A-7C, show only the electrodes 12 and 14, the optically adjustable element 13 and an optically opaque zone 18 for ease of illustration. The optically opaque zone 18 need not be completely opaque, it is just relatively opaque enough to perform the desired optical function and is usually outside of the visual axis of the wearer of the device 10*a*. The device 10*a* uses opaque charged nanoparticles 15.

Figure 7A:
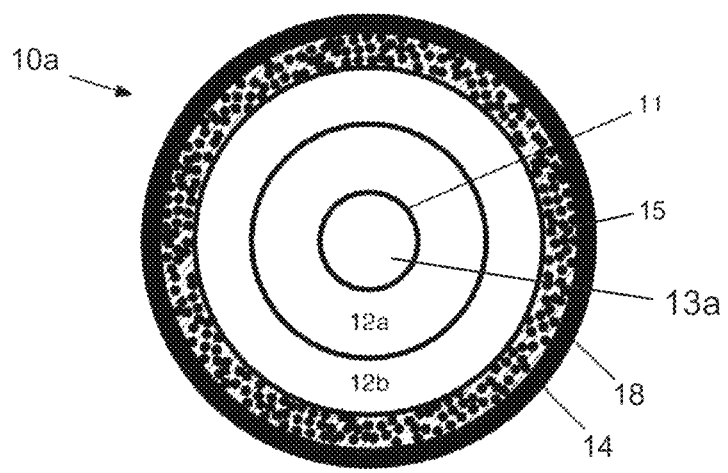
FIGS. 7A-7C are schematic front views of a portion of the intraocular prosthesis systems of FIGS. 1A-1C in different states.

As shown in FIGS. 6A and 7A, the opaque charged nanoparticles 15 are cordoned within the periphery of the mid-peripheral optically adjustable element 13, and are arranged to form an opaque annular ring. The nanoparticles 15 define the extent of the optically opaque zone 18 and are located outside of the effective aperture 13*a* which is transparent and becomes smaller as the optically opaque zone 18, which represents the iris, becomes larger. The state shown in FIGS. 6A and 7A can be referred to as the transparent state.

Figure 7B:
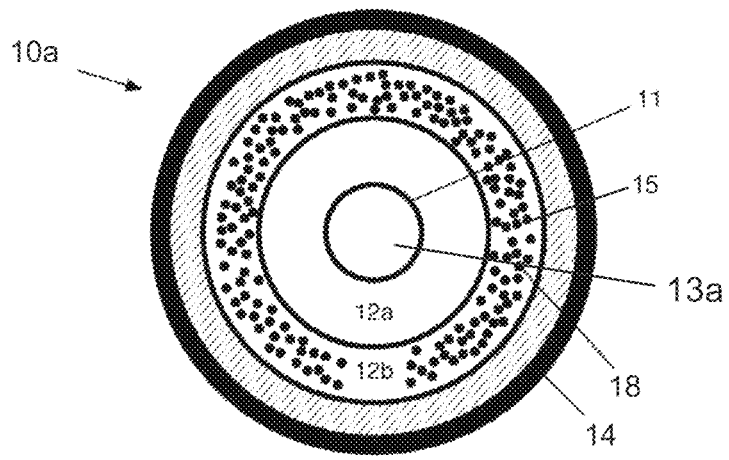
Figure 7C:
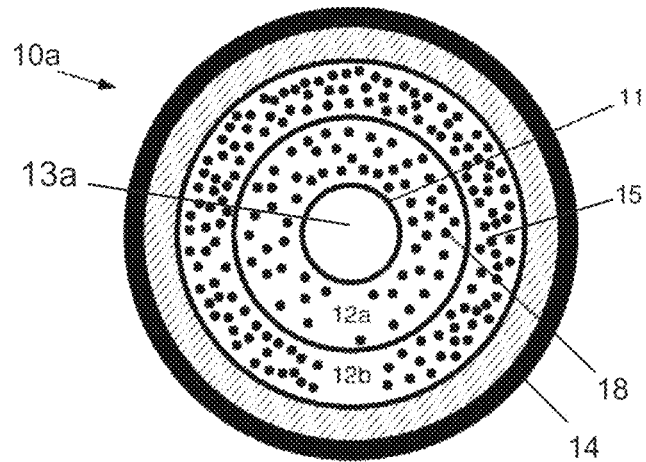

Referring now to FIGS. 6B and 7B, as the section of device 10*a* transitions from the relatively transparent state to the relatively opaque state, as it is difficult to achieve a 100% transparent state or a 100% opaque state, electric charge is applied to the electrode 12 which moves these nanoparticles 15, which are relatively opaque, concentrically inwards to decrease the size of the variable effective aperture 13*a*. For example, a dynamic electric field gradient can be applied between the electrodes 12 and 14 and varied over time to progressively migrate the opaque nanoparticles 15 closer to the center of the device 10.

Alternatively, in another embodiment, the electrode 12 may be separated into two separate electrode discs 12*a* and 12*b* and electric charge can be progressively applied to the inner electrode disc 12*a* to cause the opaque nanoparticles 15 to move closer to the center of the device 10.

In another alternative embodiment, the electrode 12 may collectively comprise several progressively smaller electrodes and the charge can be introduced into the progressively smaller concentric transparent electrodes, starting with the largest diameter electrode first and then providing charge to next smallest diameter electrode and the largest diameter electrode and so on for the electrodes that are closer to the center of the device 10. An opposite charge can be applied to the electrode 14 so that the opaque nanoparticles are progressively concentrically attracted to the smaller electrode rings and move away from the periphery where they were stored, thereby further decreasing the effective aperture size 13*a* until the opaque state is achieved for a desired effective aperture size as shown by the progression in reduced aperture size from FIG. 6A/7A to FIG. 6C/7C. Conversely, increasing the size of the effective aperture 13*a* can be done by applying a reversal of charge or a reversal of electric field gradient to the electrodes 12 and 14 in order to bring the opaque nanoparticles 15 back to the periphery of the optically adjustable element 13. In alternative embodiments, a larger number of such electrode rings for electrode 12 can be used to allow for a greater variation in effective aperture size.

When the bionic iris device, with a smart film of any embodiment, including, but not limited to nanoplating, is configured to have the smallest effective aperture, such as about 1.8 mm to 2.2 mm for example, then the optics of the device 10 allow the user's eye to function like the optics of any small aperture optical system. Specifically, the small aperture optics allow for an increase in the depth of field of the optical system of the user's eye. This can allow objects at various distances to remain in focus without the need for changing the lenticular power of the user's eye. More specifically, if the lenticular power of the optical system of the user's eye is set to plano or flat, then the device 10 allows the user to see well both objects in the distance and relatively up close. If the bionic iris device is used in a phakic eye or an eye with presbyopia, this minimizes the user's need for reading glasses for near distance vision. Furthermore, by setting the refraction of the user's optical system to mild myopia (−0.50D to −0.75D) in at least one eye, the device's small aperture setting further minimizes the user's need for reading glasses for even closer objects by allowing objects that are even closer to the user's eye to be more clear, while preserving practical distance vision, since the defocus curve of a small aperture device increases depth of field for both far as well as for near objects in this setting.

For users with a healthy cornea and a normal functioning lens or users with an aphakic or pseudophakic eye, they can have their refraction prescription optimized for this small aperture system by performing laser vision correction such as LASIK, PRK or SMILE in association prior, at the time of or after implantation of bionic iris device. For a user with a lens that has become a cataract, choosing the correct lenticular power accurately for implantation after cataract surgery allows for the correct adjustment of that user's optical system. In addition, for the user who has a cataract or who needs a pseudophakic lens, the bionic iris device can be placed either anterior or posterior to the pseudophakic lens in the lens capsule, or in the sulcus, or posterior to the pseudophakic lens with the correct optical alignment. In addition, another embodiment of any of the bionic devices described herein includes integrating one or more lenses (either a static lens or a lens with an adjustable power) with the bionic iris device 10, either by assembly within the eye or in manufacture with precise lens power incorporated into the hermetically sealed clear enclosure either posterior or anterior to the lens. In another embodiment, the powered lens can be a silicone lens or an acrylic lens that is part of membrane 20, which provides a hermetically sealed enclosure.

In another embodiment of the bionic iris device, an additional lens is attached to the device. The additional lens may be a lens of the same material or a different material and it can be positioned at an anterior portion or a posterior portion of the device. The additional lenses can be individually hermetically sealed or hermetically sealed along with the device in a larger package. The additional lens can be used for changing optical properties such as providing a static lens, a diffractive multifocal lens or an adjustable lens with an adjustable power in the eye. For example, the diffractive multifocal lens includes, but is not limited to, chromatic aberration correcting lenses. For example, the one or more additional lenses may be configured to allow for the manipulation of the focus of incoming light. For example, the bionic iris device may comprise one or more micro electromechanical actuators coupled to the one or more additional lenses to adjust the angle and location of the one or more additional lenses. In other embodiments, the one or more additional lenses can be configured to act as a telescope or telefocal lens.

In another application of any of the bionic iris devices described, by switching the device on and off, it is possible to impart an augmented reality to the user in which the device is implanted. For example, the bionic iris device can be used as part of a system that includes an external device, such as a mobile phone, that can be used to send a wireless signal to the bionic iris device thereby activating the bionic iris device by providing a charge to the antenna 16, which is then provided to certain elements of the bionic iris device. For example, the external device can communicate with the bionic iris device using Near-Field Communication (NFC) techniques. This activation can be done to signal an important event to the user, such as when an important message is received at the external device. When the bionic iris device switches on and off there may be a change in the effective aperture 13a (i.e. a section or zone of the adjustable element 13 is opacified partially, for example, and then cleared) which provides the augmented reality to the user. Accordingly, the external device can be considered to be a control device that can be used to wirelessly control the functionality of the bionic iris device.

In an alternative embodiment, any of the bionic iris devices can be set to be switched on and off in a specific pattern at a specific rate such as, but not limited to, 10 Hertz for example, or with a specific pattern of on-off such as but not limited to "on, off, pause, pause, on, off", for example, where each cycle of the pattern has the same time period or a different time period. Furthermore, information can be communicated with such patterns, such as with the use of a Morse code pattern using the on and off switching property of the bionic iris device. When the active optical zone is divided into two halves as shown in FIG. 2C, partial opacification and alternating one half such as the nasal portion 13n of a bionic iris device implanted in a right eye, for example, may be used to indicate to an individual that they need to look or turn in the direction to the left (nasal side of right eye for example). In some embodiments, the closer proximity to the location where a person needs to turn left, the faster the cycling (i.e. faster modulation of opacity or turning on and off), for example 5 Hertz when 100 feet away, 10 Hertz when 50 feet away and 18 Hertz when less than 5 feet away.

With bilateral implantation of the bionic iris device in both of the user's eyes, more sophisticated information can be communicated to the user with the bilateral implants by increasing the degrees of freedom of expression. Directions, for example, may be communicated by one or more of: (1) switching on and off the device implanted in the user's right eye for an instruction to turn right, (2) switching on and off the device in the user's left eye for an instruction to turn left or (3) switching both of the devices on together may instruct the user to slow down or to stop.

In another example embodiment of any of the bionic iris devices described herein, the sections of the optically adjustable element 13 can be separated in half, as is shown in FIG. 2C, with the nasal half and temporal half capable of being opacified or partially opacified independently of each other. This may be implemented in various ways such as by using separate circuits for each of electrode 102, 124 and 126, for device 120 for example in a nanoplating embodiment. In these embodiments, the user of the device can experience a directional augmented reality. For example, when this device is implanted in a user's eye and the user needs directions to go to a specific location, an external communicating device that is coupled wirelessly to the implanted device can be controlled to send messages to the implanted device to activate at different degrees either the nasal and/or temporal mid-peripheral zone, either separately or together with temporal synchrony or temporal asynchrony to create a visual effect that may be directional. For example, if the implanted device is in the user's left eye, both halves can be switched on/off at an increasing frequency to indicate that the user should slow down as they are approaching a turn, and as the user comes closer to the turn, the temporal half may be switched on and off with increasing frequency to instruct the user to make a left turn, while the nasal half may be switched on and off with increasing frequency to instruct the user to make a right turn.

Figure 8A:
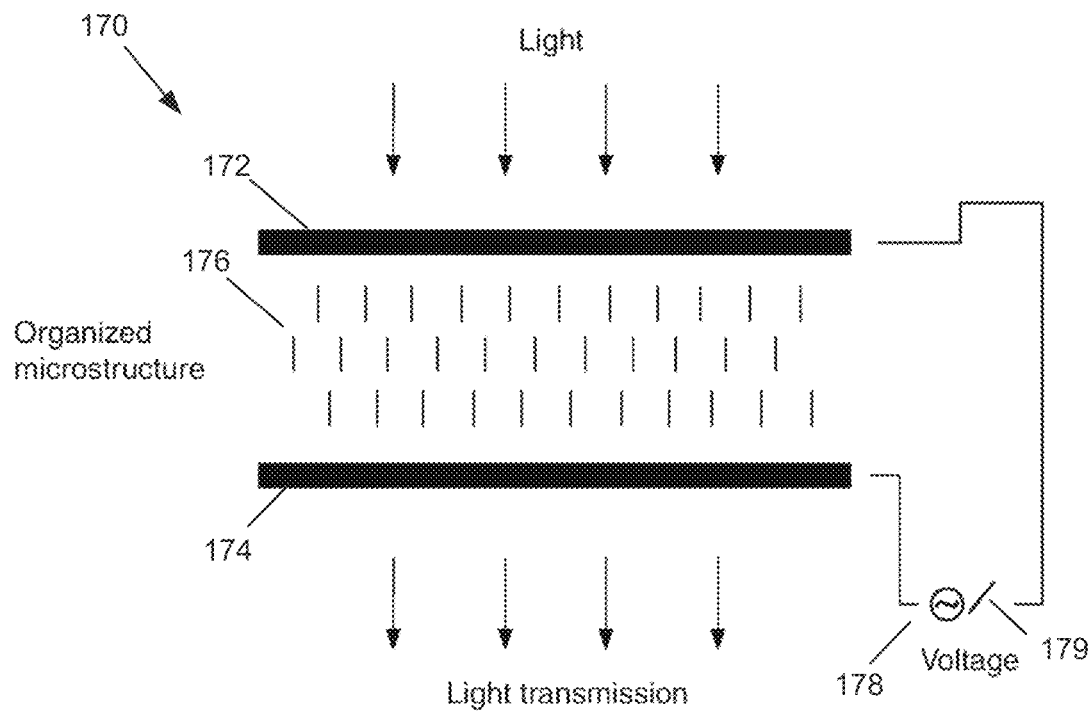
FIGS. 8A-8B are cross-sectional views, respectively, of another example embodiment of an intraocular prosthesis system in accordance with the teachings herein.
Figure 8B:
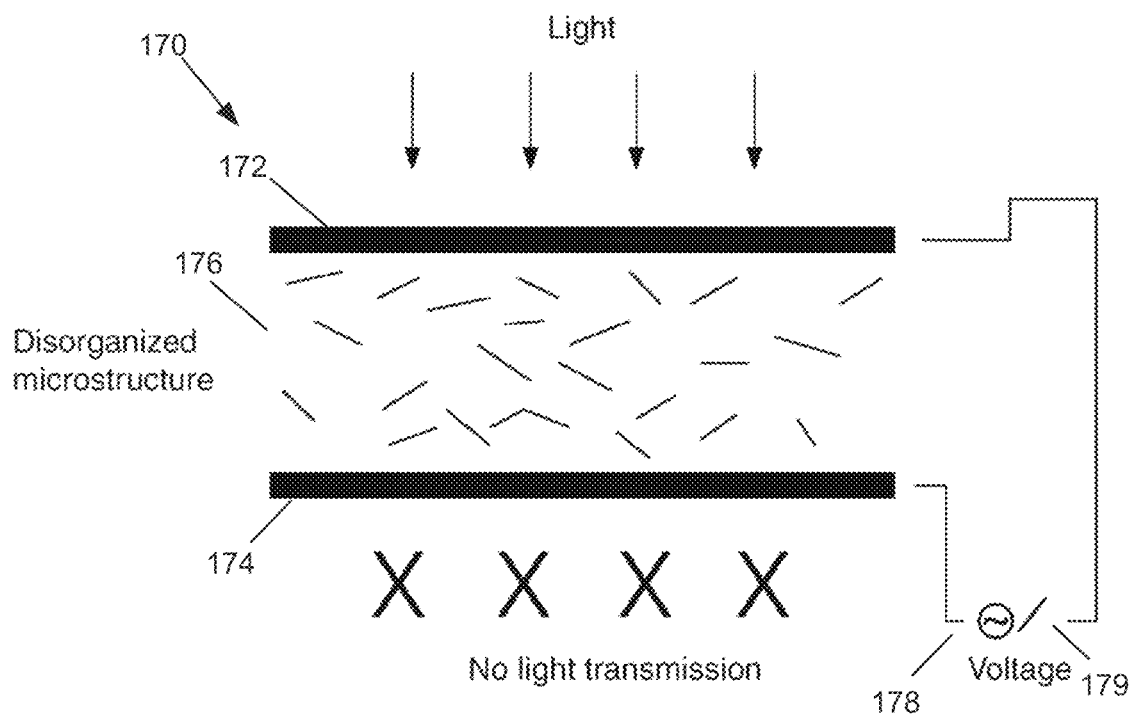

Referring now to FIGS. 8A-8B, shown therein are cross-sectional views of another example embodiment of a bionic iris device 170 in accordance with the teachings herein. In this embodiment, the device 170 uses an electrochromic-based optically adjustable element 176 that is between electrodes 172 and 174, and the resting state of the device 170 is maximally transparent when the microstructure of the electrochromic material is organized as shown in FIG. 8A. The electrochromic material may be a polymer with a structure that can be organized when subject to a charge voltage. When a specific charge voltage from voltage source 178 is selectively applied, which is schematically represented by switch 179, across the electrochromic material the microstructure of the electrochromic material becomes disorganized and transmission is progressively decreased until the maximally attenuated light transmission level is reached as is shown in FIG. 8B. In some embodiments this relatively attenuated level is reversed by applying a reverse charge voltage of a certain magnitude and time pattern, in another embodiment, the maximally transparent microstructure is reached when the charge voltage is simply stopped.

Figure 8C:
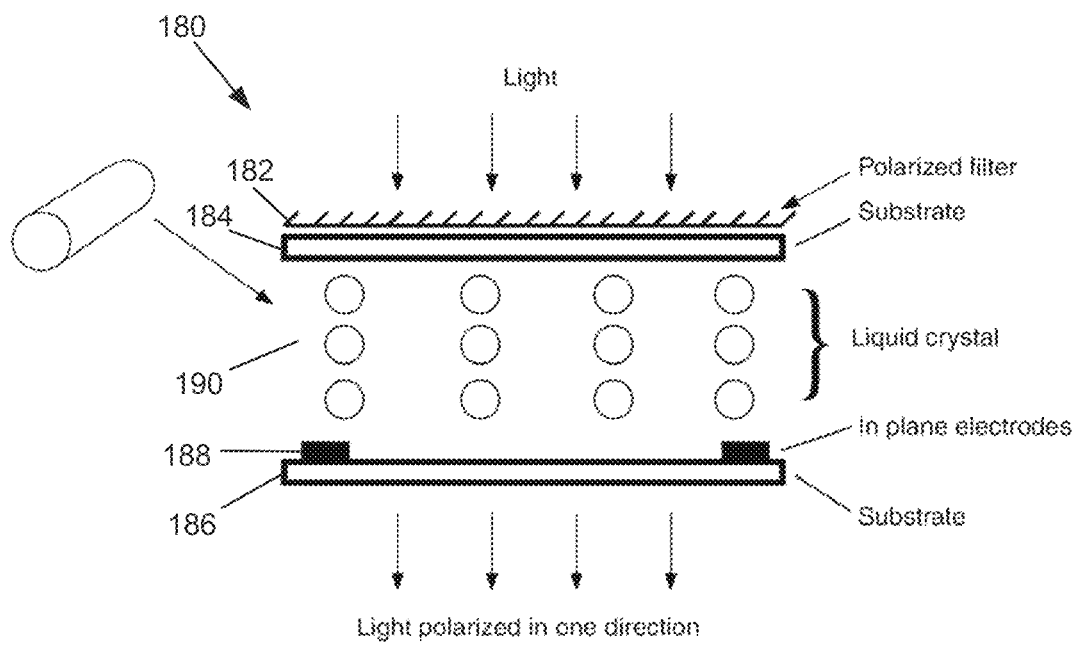
FIGS. 8C-8D are cross-sectional views, respectively, of another example embodiment of an intraocular prosthesis system in accordance with the teachings herein.
Figure 8D:
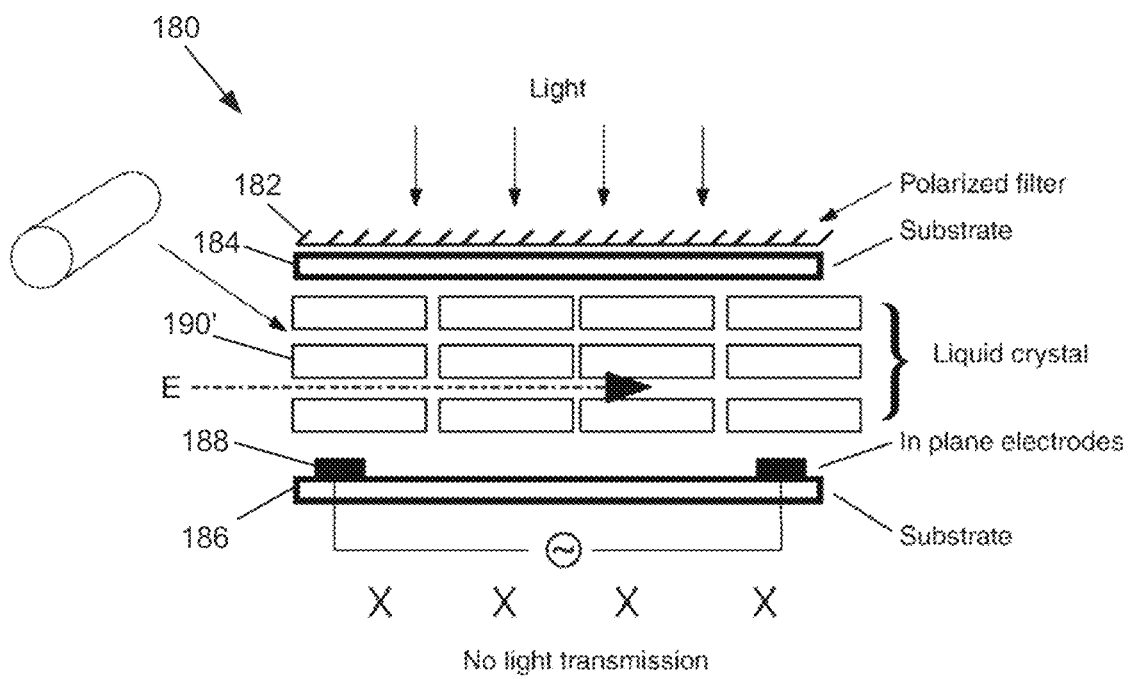

Referring now to FIGS. 8C-8D, shown therein are cross-sectional views of another example embodiment of a bionic iris device 180 in accordance with the teachings herein. The device 180 has a polarized filter 182, a first substrate 184, a liquid crystal based optically adjustable element 190 and a second substrate 186 with in plane electrodes disposed on the second substrate 186. Accordingly, the liquid crystal based optically adjustable element 190 is between the first and second substrates 184 and 186, respectively. The device 180 can be configured so that polarized light is initially transmitted in a maximally transparent setting. When a charge voltage is applied to (i.e. applied across) the liquid crystal 190, the orientation of the internal structure of the liquid crystal 190 is changed such that the polarized light is blocked and maximal opacity is achieved. In some embodiments, when this charge is stopped, the liquid crystal 190 assumes its original orientation allowing polarized light to again pass through the device 180. In other embodiments, a different charge voltage is applied at a specific magnitude and time pattern to reverse the polarized liquid crystal 190 and allow for reversal to the maximally transparent state.

In another example embodiment, the effective aperture 13a, as shown in the various figures, can have different shapes other than a circularly shaped effective aperture. For example, for bionic iris devices that use liquid crystal, the liquid crystal structure is contained in a specific shape that responds to changes in electric charge. Alternatively, for bionic iris devices that use electrochemical or electrochromic reactions to provide the variable optical properties, the active material can be contained in different shaped container. In yet another alternative, for bionic iris devices that use nanoplating, this can be achieved by either, but not exclusively, the predefined shape of the transparent electrode or the seeding (i.e. pattern of deposition sites) of the transparent electrode, and when nanoplating occurs by applying the correct charge voltage magnitude and duration to the transparent electrode, the shape of the effective aperture 13a becomes apparent. As with previously described nanoplated embodiments, a different charge voltage with certain parameters for magnitude, polarity, pattern, and duration, which may be determined through experimentation or simulation, may be applied to the transparent electrode to reverse the nanoplating and result in a maximally transparent optical element.

While the bionic iris device is in the opacified state, the optically active portion will reflect and absorb light, since it is no longer transparent. The specific reflection and absorption of light will result in specific colours and hues of the optically active portion of the bionic iris device when perceived externally, for example, by other people looking at the eye of the user who has the implanted device. The colour that is perceived is determined by which wavelengths of light are preferentially reflected, transmitted, or absorbed. This effectively allows the user with the implanted device to change the appearance of their bionic iris device. For example, if when switched on, the optically adjustable element of the bionic iris device reflects blue light and absorbs or reflects all other colours, then observers will perceive the user's eye as having a blue iris. The user may choose to change the colour and appearance of their eye in this manner. In the case of a user with a naturally smaller pupil, they may choose to dilate their pupil to allow the color of the bionic iris device to become more visible to show off their device.

In a more sophisticated embodiment of the bionic iris device, patterns of colour can be made to be absorbed and reflected by the device allowing the user with the device to change the perceived colour of their iris to the appearance that they desire. For example, in a bionic iris device that uses nanoplating, one of the electrodes, such as electrode 124, may be seeded or have a certain shape such that when it is nanoplated with a specific electrolyte, with the necessary spacers and levelers, it preferentially reflects blue light. Another electrode in the optical stack of this device, for example electrode 126 may have deposition sites that are arranged to create complex nanoplating patterns resulting in absorption and internal reflection of most wavelengths of light, resulting in a black colour for the optically adjustable portion of the bionic iris device. In this case activating the electrode 124 results in a blue iris appearance in this example embodiment and not activating the electrode 124 and activating the electrode 126 results in a black appearance for the optically adjustable portion of the device.

In yet another embodiment of the bionic iris devices that use nanoplating, it is also possible to change the amount of transmitted light, either in combination with selected reflected color or independent of selected reflected colour, the ability of which increases the degrees of freedom of expression of the bionic iris device for augmented reality communication. For example, in the above example, if the electrode 124 is designed to reflect blue and transmit other wavelengths, then the user potentially also sees these other wavelengths of light when the electrode 124 is activated while observers see blue.

In yet another embodiment of the bionic iris devices that use nanoplating, different shapes of the effective aperture and the optically active zone of the optically adjustable element 13, can be achieved by, for example, changing the pattern of deposition sites of at least one electrode that is nanoplated during use. This can be done, for example, in such a way that the user's iris will have a different external appearance. This structural colour change can be done with a method similar to the structural color effects of changing the electrode nanoplating pattern as described above. The natural blue colour of the iris stroma is secondary to the structure of the stroma of the iris for example. In other naturally occurring examples in biology, the radiant blue colour of the wings of blue morpho butterflies and other insects is also due to structural colour. The external appearance and/or colour change can also be used by the user to communicate with others. For instance, a specific pattern, colour or dynamic change of the user's bionic iris device may be used to indicate a certain mood or communicate a codified message.

In one embodiment of the bionic iris device that alters the outward appearance of the eye which utilizes nanoplating technology, this colour change is created by varying the nano-structure of the optically adjustable element by applying a charge voltage to at least one of the electrodes 102, 124 or 126. In this case, the nano-structure (i.e. deposition sites) of at least one of the electrodes 102, 124 or 126 are arranged in a shape or seeded with a pattern that results in a structural colour when nanoplated in that pattern, by reflecting the desired colour wavelengths of light and absorbing or transmitting the undesirable colour wavelengths. In this embodiment, the colour can be removed by applying a different predetermined charge voltage to the transparent electrode for example, to reverse the nanoplating of the electrode in question (i.e. electrode 102, 124 or 126).

More sophisticated control and working properties of the bionic iris device may, in some embodiments, use the implantation of an upgrade device to interface with any part of the original device using the upgrade interface module 30. In one such an embodiment, it may be possible to have light projection by adding, for example, an OLED or a solid-state laser to the bionic iris device using the upgrade interface module 30. In another embodiment, a spectrometer, may be implanted, allowing for the sensing of the concentration of relevant molecules (e.g. target molecules) such as glucose for example, or a protein such as VEGF (Vascular Endothelial Growth Factor). In either of these cases, the sensed amount of the target molecule can be communicated to the user directly through the bionic iris device, and/or through an external device.

The programming of such sensing and projection, may in some embodiments be controlled by software that is executed by the controller 28 or an external device, to select a certain sensing threshold, appearance, and/or result in certain communication functions including operating the bionic iris device to provide certain visual patterns to the user.

Figure 9:
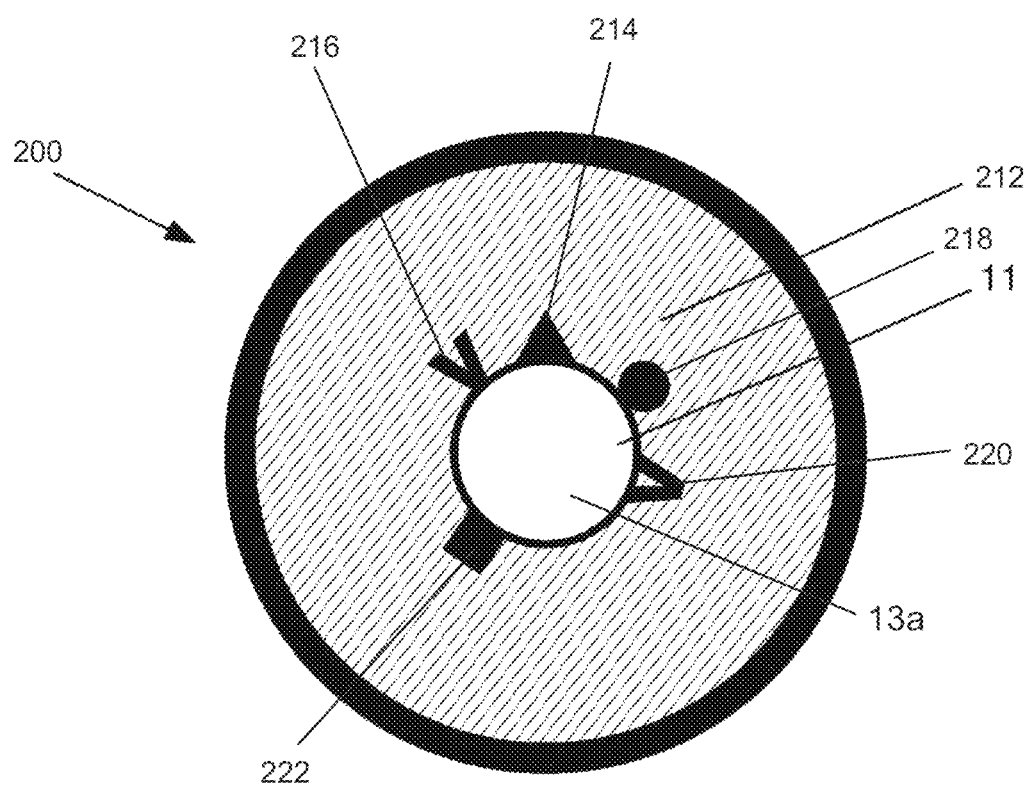
FIG. 9 is a schematic view of an example of another embodiment of an intraocular prosthesis system that includes several different optical tracking markers for tracking purposes in accordance with the teachings herein.

Referring now to FIG. 9, shown therein is a schematic view of an example embodiment of a bionic iris device 200 that includes at least one of several different optical tracking markers 212, 214, 216, 218, 220 and 222 that may be used for tracking purposes in accordance with the teachings herein. The optical markers 214 to 222 may also be referred to as electromagnetic markers. This may be useful for users who have a normal iris and users who have an abnormal or missing iris. The optical markers 212 to 222 are generally small markers that are placed in close proximity to the central region 11 of the device 200 (e.g. they can be placed at about 1.8 mm from the center of the device 200). The markers 212 to 222 are not necessarily visible to the user or to an external observer except when illuminated or observed with the correct wavelength camera. For example, in one embodiment, the markers 212 to 222 can be created with material and/or ink, e.g. Infrared dye, that is only visible when illuminated and imaged with a camera in the infrared range, thus rendering the markers 212 to 222 invisible both to the user and externally without an infrared imaging device. In another embodiment, the markers 212 to 222 are made of materials that are always visible to an external observer and/or camera under normal operating conditions and can be optimized at some wavelengths, though not easily visible to the user because of the focal length of the user's eye and the position of the markers 212 to 222 under normal operating conditions. The other components of the bionic iris device 200 are the same as any of the embodiments of the bionic iris device described herein and are not shown for ease of illustration. Although several markers 212 to 222 are shown, it should be understood that embodiments of the device 200 may use one or more of the markers 212 to 222 and possibly additional optical markers that are not shown.

Furthermore, the markers 212 to 222 can be either retro-reflective or active. An example of an active marker includes, but is not limited to, an OLED or LED. An example of a retro-reflective marker includes, but is not limited to, a highly reflective dye or material. In yet another embodiment, the markers 212 to 222 are located more peripheral to the optically adjustable element 13, not easily visible externally in the periphery of the device, and are trackable using methods including, but not limited to radio-waves, and/or emissions and/or electromagnetic fields.

In some embodiments, the optical markers 212 to 222 are tracked in 3-dimensional space as well as cyclotorsional rotation in time to determine the most likely visual axis of the eye as well as to contribute to an algorithm to determine the likelihood of accommodation convergence and direction of gaze. For example, the markers 212 to 222 will be moving closer to each other when accommodation convergence is occurring and moving away from each other when it is not. This can be done by implanting devices with markers in both eyes and comparing the movement of the markers of one eye to the markers of another eye. Alternatively, this may also be done when the device with the markers is implanted in only one eye and the movement of the markers are tracked relative to some nominal point chosen to act as a reference point. Furthermore, the cyclotorsional component of the movement of the eyes is typically different for each individual and so the markers may move in ways that are specifically defined for each individual.

The algorithm can be determined through experimentation. In some embodiments, the algorithm used may be a learning algorithm that records the tracking of the markers and validates assumptions made by the algorithm in comparison to data input by the user as to when the user is accommodating and as to what task the user is involved in. Neural networks and deep learning may be employed in the initial training to establish the baseline algorithm, whose accuracy may be improved with increased usage with correct validation inputs by the individual user.

When there is an embodiment with only a central placement of the markers 212 to 222, this allows them to be visible even in a person with a completely intact iris under photopic conditions (i.e. under well-lit conditions). In some embodiments, at least one of the invisible markers 212 to 222 are used together with an appropriate external imaging device for eye tracking. For example, using at least one of the markers 212 to 222, an external device, whether by direct visualization or indirectly with the use of radio-waves, and electromagnetic fields, can improve its ability to track the user's eye movement and specifically the visual axis of the user's eye in real time. Such precise eye tracking allows for improved foveal projection of external devices to create augmented reality for the user, either externally, or in a wearable form, for example from augmented reality eyewear.

Using at least one of the markers 212 to 222 may also allow for superior pupil tracking even in a person with a normal iris, since the actual center of the pupil is often superior and nasal to the center of the eye and varies with the constriction and dilation of the iris. Therefore, for even a perfectly tracked pupil, a pupil tracker will be tracking a relationship that changes with the visual axis at different pupil sizes and illumination intensities (i.e. the pupil size may change even with a constant illumination due to involuntary parasympathetic and sympathetic innervations as well as from accommodation). The iris markers 212 to 222 and the pupil can also cyclotorsionally shift in a pattern that is not easily predicted by tracking the pupil or the iris alone, since the dilation and constriction of the iris is not perfectly symmetrical. Therefore, following at least one of the markers 212 to 222 on the bionic iris device 200 for cyclotorsional rotation may also provide very accurate cyclotorsional tracking relative to the fovea.

Precise eye tracking is also useful to optimize the visual experience of virtual reality, mixed reality and augmented reality worn displays even when images are not directly projected on the retina. For embodiments where the bionic iris device is implanted bilaterally (in both eyes), tracking the markers 212 to 222 will allow for a more accurate prediction of accommodation convergence, especially in embodiments with limited input from either mechanical evidence of ciliary body movement (via piezoelectric actuators or sensors for example) or electrical sensing of muscle activation, nerve depolarization or combined electrical activity. Even when these inputs are available, the tracking markers 212 to 222 add value to training algorithms to maximize ergonomic activation of the bionic iris device 200. This has benefits both for the aforementioned worn virtual, mixed and augmented displays as well as improving the functional utility of the device itself. For example, in one embodiment of the bionic iris device 200, such tracking can aid in deciding when to activate the device 200, for example for signaling or contributing to the controller 28 to signal when to activate the optically adjustable element 13 to decrease the size of the effective pupil aperture of the optically adjustable element and improve mid to near distance reading by increasing depth of field when the user is converging and accommodating to read a menu for example. This same function of sensing accommodation-convergence to increase the depth of field to improve near vision is useful not only in the real world, but also for externally projected mixed reality, virtual reality, and augmented reality.

In some embodiments, the placement of the markers 212 to 222 described in the two eyes is such that tracking the pattern of movement for the markers in each eye in 3-dimensional space and cyclotorsion over time that indicates the likelihood of accommodation convergence is different for any given individual, and therefore requires an individual training period with a learning algorithm (e.g. via neural networks and/or deep learning) to optimize performance. In some embodiments, this algorithm is further optimized from sensory input including sensors on or attached to device 200 including mechanical movement within the eye and electrical activity in the location of the sensor. In some embodiments and for some users, the sensory input from the device 200 alone is enough to allow an algorithm to determine with acceptable accuracy accommodation convergence. In other embodiments, external tracking may be needed to accomplish an acceptable accuracy level.

In some embodiments, control of the device 200 may involve data such as from marker tracking as well as, when available, the internal sensory data (in embodiments with sensors) and external ambient lighting data, being relayed to an external device for a learning algorithm to compute when to trigger the device 10 to activate the optical device. This may be developed through experimentation and/or simulation and may employ the use of neural networks and/or deep learning. For example, In the setting of adjusting for accommodation convergence for example to achieve pupil effective aperture constriction to increase the depth of field for near visual tasks including, but not limited to the setting of real-time reality, mixed, augmented, or virtual reality, after a decision is made by the algorithm in the external device to activate, a control signal, including but not limited to an electrical, radiofrequency, or electromagnetic signal is sent from the external device to a sensor, antenna, and/or receiver connected to the optically adjustable element, which then undergoes an electrical, chemical, or electro-chemical process, as described in various embodiments of the bionic iris device described herein including nanoplating, to activate under the influence of the control signal from the external device. Likewise, the constriction is reversed when accommodation convergence is no longer detected to be likely by the algorithm in the external device.

In an alternative embodiment, the method of bionic iris device control can involve the external device analyzing the tracking and/or sensor data in combination with ambient lighting data, to reverse pupillary constriction and activate effective pupil dilation for improved dark adaptation, for example, by activating the optically adjustable element, such as in a device with already nanoplated electrodes to rapidly reverse the nanoplating, to maximize the area of maximal transparency for example when this is necessary to accomplish visual tasks or it is advantageous to do so otherwise. In another embodiment of the above control methods, the sensor data is sent either to a component on the bionic iris device itself such as the controller 28, or an associated external device in close proximity to the bionic iris device to control the optically adjustable element of one bionic iris device, or two bionic iris devices if implanted bilaterally, to react accordingly.

In another embodiment of a control method for the use of the bionic iris device, the dark adaptation of an individual can be optimized in one of the user's eyes with an implanted device by minimizing the effective pupil size to the smallest size that minimally affects that individual's binocular overall visual function, and maximizing the opacity of the optically active zone of the optically adjustable element 13 of the bionic iris device under baseline relatively bright operating conditions in order to maximize dark adaptation in the baseline state in that non-dominant eye. The eye that is selected for implanting the bionic iris device can be a previously determined non-dominant eye, although this control method works similarly if the device was implanted in a dominant eye. The eye that is selected depends on a number of factors including task specificity and individual preference of the user.

When the user suddenly enters an environment with low illumination, this can be sensed by a sensor of the device that senses the amount of ambient light, and the aperture of the bionic iris device in the user's non-dominant eye, which is in a state to mimic a constricted pupil, can be immediately activated by the control method (either by the controller 28, externally, or manually) to dilate (e.g. maximally dilate to maximal transparency), allowing this already dark adapted non-dominant eye to better function under scotopic (dark) conditions, allowing the user to be aware of their surroundings and continue to function while the other contralateral eye still requires more time to dark adapt. Alternatively, the bionic iris device in the constricted pupil state in the user's non-dominant eye described above can be activated manually by using an external device, by automated activation from the input of one or more ambient light sensors and/or by activation from a learning algorithm (developed as described previously for other learning algorithms) that is triggered by such sensors including, but not limited to sensors within the device, sensors in close proximity or sensors located external to the device to improve dark adaptation. In order to preserve the dark adaptation in the chosen eye, the optically adjustable element of the bionic iris device is controlled to transition into a small pupil, maximal opacity state again when the user returns to a bright light environment, by activating the device as described above and using various means such as nanoplating the optical element in the nanoplating embodiments. This method of control may be most useful for individuals who transition often between extreme changes of illumination between environments, such as soldiers or the military in the desert examining dwellings, in a snowy environment moving in and out of buildings, or on the sea going in and outside of ship cabins.

In accordance with another aspect of the teachings herein, a control method can be used to optimize an individual's dynamic range when a variable aperture size embodiment of the bionic iris device is used where the aperture acts as the individual's pupil. In such a control method, the variable pupil size can be optimized for maximum functional dynamic range for a given task under ambient lighting conditions. The maximum functional dynamic range for an individual is the most sensitive luminance range for the individual's cones and rods in their eyes which is similar to the dynamic range for a camera taking a picture. For example, the device may be controlled to have a smaller pupil size with increased nanoplating (for nanoplating embodiments) when the user is in a bright environment and the device can then be controlled to have a larger pupil with more transparent area of the optical element with reversed nanoplating when the user (who may also be referred to as a person herein) is in an environment that has a more comfortable illumination or is darker. In such embodiments, at least one illumination sensor or trigger may be used whether on the device or on an external device, that causes an applied charge voltage of a predetermined polarity, pattern, magnitude, and duration when a change in illumination is detected to maintain the illumination level predetermined to result in the optimal dynamic range for a task for a specific individual. For example, if the user moves to a brighter environment, the optically adjustable element is controlled to nanoplate more surface area so that the pupil becomes smaller and less incoming light is transmitted to the user's retina. When the user then moves to a darker environment, a different charge voltage causes the nanoplating to reverse and more surface area of the optically adjustable element becomes more transparent resulting in a larger pupil size. Accordingly, the device can be automatically controlled to optimize function dynamically, and may be configured to do so at all times and in all environments. Such embodiments may be useful for any user to maximize their visual function by optimizing their dynamic range. This functions similarly to how a normal iris functions to block out bright light. Nanoplating over the central aperture can also affect the central transparency of light or to any given wavelength of light. Such embodiments may also be used to protect an individual from excessive exposure to harmful electromagnetic radiation such as excessive UV or blue light exposure since the implant will likely be able to produce a much smaller effective aperture pupil than most natural irises. For example, a natural iris does not typically go smaller than 3-4 mm, while at least one embodiment of the bionic iris device described herein can have an aperture that can go down to about 1.6-1.8 mm.

Accordingly, in one embodiment, there is provided a method of optimizing a visual dynamic range of a person by controlling an amount of light that enters into an eye of the person when the eye includes a device for modulating incoming light, the device being defined according to any one of the appropriate teachings herein and being configured to provide variable aperture sizes. The method comprises determining optimal aperture sizes (and/or transparency levels) for a maximum functional dynamic range for the person performing a given task under different ambient lighting conditions; detecting a change in illumination in an environment of the person; and providing an applied voltage of a predetermined charge, pattern, magnitude, and duration when the change in illumination is detected to change the aperture size (and/or transparency level of a portion) of the device to one of the optimal aperture sizes (and/or optimal transparency levels) for the illumination of the environment of the person to result in the optimal dynamic range for a task for a specific person. For example, if the individual moves to a brighter environment, the device may undergo nanoplating to mimic a smaller pupil to allow less incoming light to be transmitted to the person's retina. When the person moves to a darker environment, a different charge voltage causes the nanoplating to reverse and the device provides a larger size aperture to mimic a pupil that has enlarged. Alternatively or in addition, the device may undergo, for example, nanoplating or stripping of one or more portions of the device (e.g. the iris portions and/or the portions overlying/defining the central aperture) to adjust a transparency level of the one or more portions, and in some examples, the transparency level of one or more portions may be increased while the transparency level of one or more other portions may be reduced to help optimize the visual dynamic range. In some examples, the transparency level can be adjusted with respect to a specific wavelength range of electromagnetic radiation, for filtration of the specific wavelength range of electromagnetic radiation. For example, the transparency level may be adjusted for filtration (e.g. blocking transmission) of blue light.

In another aspect, in accordance with the teachings herein, in embodiments of the device that can provide variable pupil sizes, these devices can be used to improve the user's circadian rhythm. In such embodiments, at least one illumination sensor either located on the device or externally communicates with the controller 28 to cause an applied charge voltage of a predetermined polarity, pattern, magnitude, and duration to change dynamically throughout the day to ensure that the aperture sizes (where the aperture acts as a pupil), overall transparency, and/or blue light filtration of the device are optimized for maximum functional vision and adjusted for the individual's preferred circadian rhythm throughout the day. For example, the adjustment may be done based on the user's circadian rhythm so that more incoming light (and in some examples, specifically more blue light) may be allowed into the user's eye for the time period that corresponds to the morning for the user's defined circadian rhythm and less light (and in some examples, specifically less blue light) may be allowed to come into the user's eye for the time period that corresponds to the evening for the user's defined circadian rhythm when the user should be winding down to prepare for sleep even in bright internal or external environments. For example, the circadian rhythm may be defined by the user depending on their location, such as Hong Kong or London, but may also be optimized based on the user's own needs since not everyone functions optimally with exactly 8 hours of sleep. Alternatively, the user's circadian rhythm may be defined for a location that the user will travel to which has a different time zone. For example, the user may be in London but they have defined their circadian rhythm according to the time zone in Hong Kong since they will be travelling there soon.

For example, in the embodiments which use nanoplating, at least one of the transparent electrodes of the device are nanoplated to result in a smaller effective pupil aperture to allow less light transmission when the user's ideal circadian rhythm dictates that the user should be winding down to prepare for sleep, even in bright internal or external environments. Additionally, when at least one of the transparent electrodes of the device undergo reverse nanoplating of a certain amount of surface area the result is a larger pupil and this can be done when more light is necessary for fulfilling a task or the user should be in the early morning component of their optimal circadian rhythm and should be exposed to more light. This embodiment may be especially useful for user's engaged in shift work or who are changing time zones.

In addition, it should be noted that mapping a fixed specific relationship to the fovea based on at least one of the markers 212 to 222 on the device 200 can ensure foveation (e.g. when projected light is exactly projected onto the fovea) of the user's eye at the optimum angle of incidence to the line of sight. There is evidence that the retina has directional sensitivity, which has been demonstrated in the past as the Stiles-Crawford effect. Therefore, controlling directional projection correctly allows for the best possible foveal projection of augmented reality onto the user's retina. Using at least one of the markers 212 to 222 therefore allows for the tracking and identification of the visual line of sight, which is a construct that does not have any consistent geometry relative to stable landmarks in the normal eye. In addition, as mentioned earlier, in some embodiments of the bionic iris device, the location of the center clear optical zone can be adjusted to optimize the visual pathway to take advantage of directional retinal sensitivity. For example, the aperture location and size of the device 200 can shift based on information provided to the device 200 by applying a charge voltage to electrode 102, 124 and/or 126 as necessary depending on the computed light of sight is, which may be determined by a tracker, for example in one embodiment. Since the relationship of the optical markers 212 to 222 do not vary with this new adjusted center clear optical zone, tracking of the visual axis can still be accurately performed.

In another embodiment of the bionic iris devices described herein, a light source is located on the device. The light source includes, but not limited to a LED, an OLED, a laser projector or any other suitable laser or light emitting device. In some embodiments, the light source is projected towards the user's retina, in other embodiments, the light source is projected away from the retina. In some embodiments, the light source, such as a laser projector, is projected towards the user's fovea. In other embodiments, the light source is projected away from the user's fovea. In other embodiments, the light source is projected towards the individual's peripheral retina. In yet another embodiment of the device 10, the light source is located in close proximity (for instance on the device or near the upgrade module of the device) and is powered and/or is controlled by the bionic iris device. The light source can be located on the device or in other embodiments is located on an upgrade element to the device.

In these embodiments, the purpose of the light source includes, but is not limited to, communicating with the user, facilitating eye tracking, and communicating with an external device. In some embodiments, the light source has a separate circuit that allows for control from an external device without necessarily first communicating to the optically adjustable element of the bionic iris device or the circuitry involved with the optically adjustable element and thus can be operated independently from it.

In at least one embodiment of the bionic iris device, at least one sensor is included and used for measuring at least one parameter related to the user's eye where the device is implanted. For example, in some embodiments, a motion sensor can be located on the bionic iris device 10 in order to sense the contraction of the ciliary muscle. In another embodiment, a different sensor can measure electrical activity at the site of the sensor. Alternatively, in some embodiments, a mechanical pressure sensor can be adapted to measure mechanical force at the sensor.

In another embodiment of the bionic iris devices described herein, a photosensor is embedded to detect and activate the optically adjustable element to decrease the size of the effective pupil aperture under bright conditions and increase the pupil aperture under dark conditions. A similar effect can also be created in another embodiment where a solar cell or an array of solar cells are included in the bionic iris device. For example, in embodiments which use nanoplating where the equilibrium of the nanoplating device is such that when no power is applied, the device fails to a transparent state, and when there is sufficient light to power the solar cell and/or array of cells, the optically adjustable element becomes active and nanoplating is achieved such that the greater the charge, due to a larger amount of ambient light, the larger the surface area of the at least one of the electrodes 102, 124 and 126 that is nanoplated directionally from the periphery to centrally. In effect when there is enough electrode nanoplating, the pupil becomes smaller under bright light. As the external environment becomes darker and the solar cells are not charged sufficiently, no charge is applied to the optical element, and in this particular embodiment, as stated, since in equilibrium with no applied charge voltage failure is to transparency, and the optically adjustable element then becomes more transparent and the pupil aperture is effectively enlarged.

In at least one embodiment, one of the bionic iris devices described herein includes at least one biomarker sensor in order to measure or sense at least one biomarker in the intraocular fluid space of the user's eye in which the device is implanted. For example, the concentration of specific molecules in the fluid (i.e. aqueous humor) of the eye can be measured such as, but not limited to, glucose and/or VEGF. Alternatively, in yet another embodiment, the biomarker sensor can be adapted to measure the concentration of multiple molecules in the aqueous humor. In yet another embodiment, the sensor is a spectrometer located either with the device or available as an upgrade module. In embodiments with a spectrometer, its purpose includes, but is not limited to, detecting specific biomarkers in the location of the spectrometer. Accordingly, the biomarker sensor includes, but is not limited to, one or more of a glucose sensor, a protein sensor, an enzyme sensor and a cytokinin sensor. The biomarker sensor may be disposed on a protective membrane of the bionic iris device. In some embodiments, there can be two or more biomarker sensors in the device.

In some embodiments of the bionic iris devices that include biosensors, the biosensors activate the optically adjustable element and/or sections of the optically adjustable element to communicate measurement thresholds to the user, which may be done using coded messages as described above. In another embodiment, the sensing data and thresholds are communicated to an external device. In yet another embodiment, the measurement values and thresholds are stored in a memory on the bionic iris device and are communicated in bulk to an external device. In yet another embodiment of the bionic iris device, either the device or an upgrade module also contains a voltage released drug reservoir that is voltage controlled to release the drug in the reservoir such that when a measurement threshold is reached, such as a certain level of VEGF, then a signal is sent to the drug reservoir to release medication for example. In some embodiments the trigger is a voltage and the release mechanism is the application of the voltage to a membrane that triggers the dissolution of the membrane and the release of the drug/medication. In some embodiments, there may be a plurality of micro-reservoirs of micro-dosed medication that are released to provide the medication to the eye when a wireless signal is sent to the controller or a condition requiring the medication is sensed.

In at least one embodiment of the bionic iris device with at least one sensor, the sensor is designed to sense intraocular pressure using a pressure transducer or a series of pressure transducers to compensate for drift. In one embodiment, the pressure is measured at set intervals and recorded on a memory chip, as described above, and this information is then communicated to an external device when triggered by an external device, to allow for a diurnal log of intraocular pressure through different times of the day and to minimize power consumption for transmitting the data. In another embodiment of bionic iris devices that include at least one intraocular pressure sensor and a drug reservoir, medication can be released for the treatment of increased intraocular pressure when this is necessary.

In some embodiments, the device 10 can include both the motion sensor and one or more biomarker sensors just described.

In some embodiments, the bionic iris device may be used to facilitate measurement of an analyte in the eye. For example, the implanted device can be used as part of a non-invasive method to measure constituents in the blood such as blood glucose when implanted in the eye. The aqueous humour, which is the fluid in the anterior portion of the eye, is derived from blood plasma, and the concentration of glucose in the aqueous (GA) is directly proportional and correlated to the concentration of glucose in the blood (GB). In the absence of injury or inflammation in the eye, the GA is also correlated to the optical properties of the aqueous, including light scatter. Measuring these optical properties allows one to estimate blood glucose concentration. One method of measuring these optical properties is with external imaging methods illuminated or stimulated by external light or laser of specified wavelengths and/or spectrum of wavelengths. Such imaging methods can benefit from a background standard with which to compare and calibrate the measurement device. In such a system, the implanted device can serve as a controllable standard in the optical path of such a measuring system. In the absence of an implant, only the iris or an optically inert clear lens serves as a background in a normal eye. However, the iris differs for every individual eye, is unpredictably dynamic, and is unpredictably affected by sympathetic and parasympathetic innervation in addition to ambient lighting, and therefore is not easily controlled even in the same eye of an individual. In contrast, the appearance of the implanted device can be constant and visible in the visual axis. For example, the non-nanoplated portions of the implant can provide a known, consistent background with known consistent background optical features for different patients and different eyes. In addition, the nanoplated portions of the implant can precisely and consistently control the surface appearance, transparency, and reflection of the implanted device. This consistency between different eyes and the precise dynamic control of the implanted device within any given eye, can help improve the accuracy and consistency of GA estimates and therefore GB levels. When specifically controlled for a known reflectivity, the implant can also direct the known reflected optical pathway of incoming illumination which may help to further improve the accuracy of GA measurements. In some embodiments, constituents other than glucose can be assessed in a similar manner. In some embodiments, the method of imaging and analyzing the anterior chamber fluid can utilize spectroscopy methods such as Raman spectroscopy. In other embodiments, the anterior chamber fluid can be stimulated by a laser such as a Nd:YAG laser, into plasma, and the aqueous contents can be analyzed using a method such as laser induced breakdown spectroscopy (LIBS).

Figure 10:
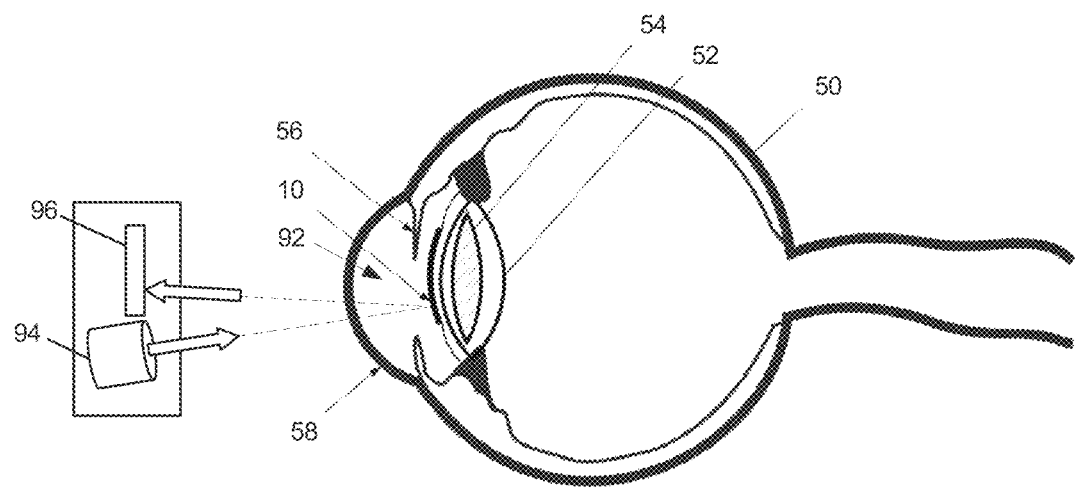
FIG. 10 is a schematic of a system for measuring analyte in aqueous humour of an eye having an implanted prosthetic iris device.
Figure 11:
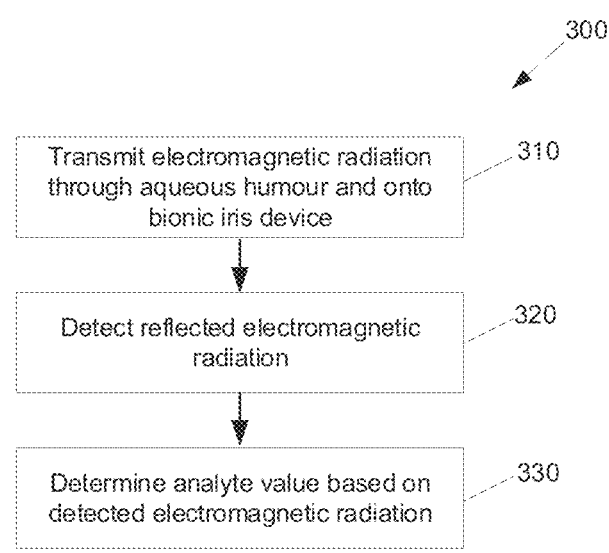
FIG. 11 is a flow chart showing an example process for measuring analyte in aqueous humour of an eye having an implanted prosthetic iris device.

Referring to FIGS. 10 and 11, an example method 300 of measuring an analyte (e.g. glucose) in aqueous humour 92 of an eye 50 is shown schematically. At step 310 of the method 300, electromagnetic radiation is transmitted (e.g. from an external light source 94) through the aqueous humour 92 and onto a prosthetic iris device 10 implanted in the eye 50 posterior of the aqueous humour 92. In this embodiment, the iris device 10 provides a controllable background standard in the optical path of the transmitted electromagnetic radiation. At step 320 of the method 300, electromagnetic radiation reflected from the aqueous humour 92 and the iris device is detected (e.g. using a sensor 64). At step 330, an analyte value for the analyte is determined based at least in part on the electromagnetic radiation detected in step (b). In some examples, the analyte value corresponds to a glucose level in the aqueous humour 92, and the method 300 can further include the step of determining the glucose level based on the analyte value.

In some examples, step 330 includes determining one or more apparent optical properties of the aqueous humor 92 and iris device 10 based on the electromagnetic radiation detected in step 320, and comparing the apparent optical properties to one or more corresponding baseline optical properties for the aqueous humour 92 and iris device 10. In some examples, the optical properties comprise reflectance. The one or more baseline optical properties can correspond to the optical properties of the aqueous humour 92 and the iris device 10 under known analyte values, and may be determined during an initial calibration.

In some examples, step 330 includes generating at least one image of the aqueous humour 92 and iris device 10 based on the electromagnetic radiation detected in step 320, and identifying a deviation in one or more image properties (e.g. image quality, hazing, etc.) between the at least one image and one or more baseline images for the aqueous humour and iris device. In some examples, the deviation corresponds to the analyte value, and the analyte value is determined based on the deviation. The one or more baseline images can correspond to images of the aqueous humour 92 and iris device 10 under known analyte values, and may be generated during an initial calibration.

In some examples, the electromagnetic radiation comprises laser light, and the analyte level is determined at least in part through laser spectroscopy. In some examples, a laser beam can be transmitted into the aqueous humour, and the analyte level can be determined at least in part through spectroscopy, including, for example, Raman spectroscopy. In some examples, an Nd:YAG laser pulse can be transmitted into the aqueous humour, and the analyte level can be determined at least in part through, for example, laser induced breakdown spectroscopy. In some examples, the electromagnetic radiation comprises polarized light, and the analyte value is determined based at least in part through polarimetry.

In some examples, during step 320, the iris device is in a first state. In some examples, the method 300 further includes the step of transitioning the bionic iris device to a second state different from the first state, detecting electromagnetic radiation reflected from the aqueous humour 92 and the iris device 10 in the second state, and during step 330, determining the analyte value based further on the electromagnetic radiation reflected from the aqueous humour and the iris device 10 in the second state. In some examples, the first state corresponds to a first value of an optical property of the iris device and the second state corresponds to a second value of the optical property, with the second value being different from the first value. In some examples, the optical property comprises reflectance. Transitioning the iris device between states during the method 300 can help to provide different backgrounds, which may be useful in cases where, for example, a different background contrast may be more suitable in assessing an analyte value under certain conditions (e.g. under low glucose levels or high glucose levels). In some cases, it may be helpful to determine the analyte value based on a relatively low contrast background provided by the iris device 10 as well as a relatively high contrast background provided by the iris device 10 for redundancy and/or to help improve accuracy.

In some examples, the method 300 further includes applying a charge voltage to transition the iris device from the first state to the second state. In the nanoplating examples, the charge voltage can be applied between a working electrode and a counter electrode of the iris device. In some examples, transitioning the iris device 10 from the first state to the second state includes at least one of: nanoplating the working electrode with ions from an electrolyte in the iris device 10, and stripping the working electrode of the ions. In some examples, the charge voltage is applied according to a predetermined polarity, magnitude, and duration.

In another embodiment of the various bionic iris devices described herein, in addition to obtaining energy by receiving a wireless signal at the induction coil 16, a piezoelectric mechanism can also be used to provide energy to the bionic iris device. In one embodiment, this charge is obtained from the kinetic motion of the eye and the user, similar to kinetic mechanisms found in watches. Some of these mechanisms involve a weighted rotor optimized for the eye, that moves as the user moves such that the movement mechanically charges a capacitor, which provides the power necessary to function the bionic iris device. In another embodiment, this charge is obtained from the force of the contractions of the ciliary body which can be done using a method including, but not limited to, either directly or indirectly charging a piezo-electric component, or using a mechanical method similar to the watch example described above.

The various embodiments of the bionic iris device described herein may be controlled through wireless induction using a single resonant frequency or a combination of resonant frequencies as described earlier. In these embodiments, power transferred by wireless induction can be stored in an on-board battery, capacitor, or super-capacitor. Alternatively, the storage devices may receive charge from various devices including, but not limited to, at least one of a piezoelectric element, a photovoltaic element (e.g. a solar cell), a photodiode, a fuel cell, or other charging means that are configured to provide power to certain elements of the bionic iris device.

In some embodiments, these energy generation elements are used directly for specific functions of the bionic iris device, such as solar cells that may be used to both detect and trigger, power or help power a response to ambient illumination intensity as was described above. For example, when illumination is high, there is an advantage to control the optically adjustable element to decrease the aperture size of the pupil to improve vision and comfort, and may indicate an intention to read, and therefore having a decreased pupil size associated with higher illuminations is also advantageous in these scenarios by increasing depth of field to improve visual acuity for near tasks. Other cues may be used to determine an intention to read such as accommodation convergence, ciliary body activity, electrical activity, or any combination thereof. In other embodiments that seek to sense an accommodation convergence response, a piezoelectric or mechanical component may function to both sense mechanical movement either directly or indirectly (for example indirectly via movement of the zonules, vitreous or capsular bag) of the ciliary body and to both help power and trigger a response function of the bionic iris device, such as decreasing pupil aperture size accordingly to improve depth of field when accommodation is desired by the user. In another embodiment, one or more of these components and methods of charging, power transfer, and control can be used in combination.

In some embodiments of the device, the trigger to decrease pupil size can be computed by a learning algorithm (such as a deep convolutional neural network) that takes into account the following which is included but not limited to accommodation-convergence predictions from marker positions, ciliary body mechanical activity, capsule movement, electrical activity at the ciliary body, ambient change in illumination, illumination intensity, and other movements of the head and the eye.

In another embodiment of the device, the optically adjustable element 13 is implemented so that the active optical zone does not become completely opaque during use, but rather can change to allow for the transmission of certain wavelengths of light and/or can allow for a certain percentage of light transmission. For example, in the embodiments utilizing nanoplating, the percentage of light transmission can easily be altered by changing the amount, duration, and wave pattern of the charge voltage that is applied to at least one of the electrodes 102, 124 and 126, which in turn limits the physical amount of nanoplating on the electrodes that receive charge voltage and therefore limit the amount of light that is transmitted, reflected, and absorbed. Further, with the nanoplating embodiments, mathematical functions for a specific property of any given electrolyte can be calculated and graphed for example as a function of transparency versus time for a given charge, and therefore by altering the amount of time that the charge is applied, the desired light transmission can be obtained. Likewise, a function of transparency versus charge for a given time can also be calculated as well as a function for transparency for a given set of charges and times. This allows the adjustment of variables necessary to attain a certain degree of transparency for any given electrolyte and nanoplating chemistry. In addition, it should be noted that the modulation transfer function of different wavelengths of light at each degree of transparency can also be dictated by the electrolyte in a nanoplating embodiment. Therefore, in one embodiment, the transmission, reflection, and absorption of a specific wavelength of light can be altered by the magnitude and time duration of an applied charge voltage, and specific contents of the electrolyte. However, the functions can be more complex and can also vary over usage time or number of repeated cycles, depending on the relative stabilities of the transparent electrode, electrolyte, counter electrode, and ions used.

In some embodiments of the bionic iris device, the bionic iris device can be implanted together with an intraocular lens, either anterior or posterior to the lens, either at the time of intraocular lens implantation or after. The position of the device 10 when implanted in the presence of an intraocular lens will depend on the status of the other elements in the eye such as the lenticular capsular bag and the type of intraocular lens. In some embodiments when the bionic iris device is implanted together with a monocular intraocular lens, the bionic iris device can serve both as an adjustable aperture and be used in a method to extend the depth of field of the eye. In yet another embodiment of the device, when the device is implanted together with an intraocular lens with more than one discrete focal point, such as a diffractive, diffractive achromatic or zonular refractive lens, the bionic iris device may be specifically aligned with the zones and/or diffractive rings of the intraocular lens to help minimize or reduce unwanted dysphotopsias and night vision symptoms that are common with such diffractive based or zonal refractive lenses. In one method embodiment of the use of device 10, a device 10 is specifically implanted and aligned with a multifocal or diffractive lens to specifically decrease night vision symptoms in certain lighting conditions. In some embodiments, alignment is done visually with the diffraction gratings or refractive zones. In other embodiments, alignment is accomplished by physical markings and notches on the device and the lens that can be located at, including but not limited to, the outer edge of the device and lens as well as the inner edges of the aperture of the device and lens as well as the interface surfaces between the device and the lens. In another embodiment, the optically adjustable element 13 of the bionic iris device may have a second element with a lens component incorporated within it, such that the lens may even act as the backplate to the optical stack for bionic iris devices that use nanoplating. In yet another embodiment of the device, this second element with a lens has an optical power that can be adjusted, and this adjustable power element may have a separate activation circuitry depending on the adjustable power lens element used.

For example, in one embodiment, a method is provided for decreasing dysphotopsias and night vision symptoms associated with a multifocal intraocular lens having diffractive elements for a user having an existing intraocular lens and a switchable implanted device that is defined in accordance with any of the appropriate teachings herein. The method comprises: implanting the device with a specific orientation and positioning to align portions of the device that undergo nanoplating during use with corresponding portions of the multifocal intraocular lens where at least one of the diffractive elements is located such that when nanoplating at the portions of the device occurs, the corresponding portions of the multifocal intraocular are masked which allows primarily the central distance portion of the intraocular lens to function when nanoplating occurs, therefore decreasing night vision symptoms by only allowing incoming distance vision without stray light which is the cause of night vision symptoms and dysphotopsias. The device may be controlled to activate nanoplating either manually with an external device when the user wishes to see distance without stray light and dysphotopsias caused by diffractive components and is not interested in reading, or automatically with a learning predictive algorithm that predicts likelihood of not reading as discussed above. The device may then be controlled to undergo reverse nanoplating either manually with the external device when the user wishes to read by making transparent and active the diffractive components of the lens, or automatically with the learning predictive algorithm that predicts likelihood of reading as discussed above.

For example, the above embodiment may be useful in cases where a lens may have 2 or more refractive zones and having all of the refractive zones transparent may cause uncomfortable or distracting visual symptoms for the user. However, when a portion of the device is nanoplated to modulate incoming light to a given refractive zone such that light is not transmitted through the given refractive zone and thus will not contribute to visual function, then the lens will thus function as a regular monofocal lens. A similar effect can be achieved by modulating the transmission of incoming light with the use of nanoplating when necessary, therefore functionally turning on and off specific diffractive optical elements of the lenses. A similar effect can be achieved with the phase shift elements of lenses.

The embodiment of the device described above that is designed to block out portions of the lens not used can be used to treat and/or prevent unwanted visual symptoms associated with diffractive and multifocal lenses. In the simplest embodiment of this method, the device can either be switched manually by the user with an external device, or triggered by an algorithm that predicts reading such as described above, to either nanoplate and block the portions of the device that correspond in location with the elements of the lens that are necessary for near vision when the user wishes to see in the distance and reverse the nanoplating so that any nanoplated portions of the device do not block the near vision components and diffractive elements of the lens and allow them to function when the patient wishes to read or see near objects. The device can also be configured to nanoplate certain portions of the device that correspond in location to the distance components of the lens in addition to clearing the reading components of the lens in other embodiments.

In another example embodiment, there is provided a method of decreasing dysphotopsias and night vision symptoms associated with refractive zonal lenses having refractive elements for a user having an existing intraocular lens and a switchable device that is defined according to any the appropriate teachings herein. The method comprises: implanting the device with a specific orientation and positioning to align portions of the device that undergo nanoplating during use with corresponding portions of the refractive zonal lens where at least one of the refractive elements is located such that when the nanoplating at the portions of the device occurs to create opaque zones, the corresponding portions of the refractive zonal lens are masked by the opaque zones. This allows primarily the central distance portion of the intraocular lens to function when nanoplating occurs, therefore decreasing night vision symptoms by primarily allowing incoming distance vision without stray light which is the cause of night vision symptoms and dysphotopsias. The method further comprises controlling the device to activate nanoplating either manually with an external device when the user wishes to see distance without stray light and dysphotopsias caused by zonal refractive components and is not interested in reading, or automatically with a learning predictive algorithm that predicts likelihood of not reading as discussed above. The method also includes controlling the device to reverse nanoplating either manually with an external device when the user wishes to read by making transparent and active the zonal refractive components of the lens, or automatically with a learning predictive algorithm that predicts likelihood of reading as discussed above.

In some examples, an intraocular prosthesis system including an optical device like those disclosed herein can be utilized for dynamically varying one or more adjustable optical properties for the eye. The one or more adjustable optical properties can include, for example, at least one of transmission, reflection, absorption, polarization, and wavelength filtration of incoming electromagnetic radiation by the optical device. In some examples, the one or more adjustable optical properties can include a depth of field for the eye.

Referring to FIG. 12, an example intraocular prosthesis system 401 for dynamically varying one or more optical properties for the eye is shown schematically. The system 401 includes an optical device 410 implantable in an eye. The optical device 410 has at least one adjustable optical element 413 operable to dynamically vary the one or more optical properties for the eye. In the example illustrated, the system 401 further includes a controller 428 in communication with the optical device 410 and configured to control adjustment of the optical element 413 for varying the one or more optical properties. The controller 428 can be external to and in wireless communication with the optical device 410 for controlling adjustment of the optical element 413 (as shown in the schematic example of FIG. 12), or can be integrated with and in wired communication with the optical device 410.

In some embodiments, the optical element 413 is operable to vary a depth of field for the eye, and the controller 428 is configured to control adjustment of the optical element 413 for varying the depth of field. For example, the depth of field can be varied such that the effective distance between the nearest objects (i.e. the depth-of-field near limit) and furthest objects (i.e. the depth-of-field far limit) that form a focused image on the retina can be increased or decreased. In some embodiments, the depth of field can be varied in this manner by adjusting an optical aperture provided by the optical element 413, as described in more detail below. In such embodiments, when a size of the optical aperture is smaller, the depth of field is increased (i.e. the effective distance between the nearest and further objects that form a focused image is increased), which can also be referred to as the depth of field being extended. When the size of the optical aperture is increased, the depth of field is decreased (i.e. the effective distance between the nearest and further objects that form a focused image is decreased), which can also be referred to as the depth of field being made shallower or narrower.

In such examples, the system 401 can further include one or more sensors for detecting intraocular and/or environmental conditions and generating sensor signals indicative of the intraocular and/or environment conditions, and the controller 428 can be configured to control adjustment of the optical element 413 based at least on the sensor signals to provide a suitable depth of field for the intraocular and/or environmental conditions. The sensors can include, for example, an illumination sensor for measuring environmental illumination (e.g. general ambient illumination and/or illumination of a target area or objects in the visual axis of the eye), a rangefinder, etc.

In examples in which a rangefinder is provided, the rangefinder can be operable to estimate a distance to one or more objects of interest (e.g. an object in a visual axis of the eye) and generate rangefinder signals indicative of the distance, and the controller 428 can control adjustment of the optical element 413 based on at least the rangefinder signals to provide the suitable depth of field. For example, in some embodiments, the controller 428 can operate the optical element 413 to provide an extended depth of field when the distance to an object of interest is less than a first near distance threshold (e.g. to facilitate near and distance focus), and the controller 428 can operate the optical element 413 to provide a narrower depth of field (e.g. by reducing or eliminating near vision focus) when the distance to an object of interest is greater than a second near distance threshold. Narrowing the depth of field in this manner can, for example, facilitate improved distance vision by, for example, increasing the amount of light transmitted through the optical element to the retina when the device incorporates a more conventional lens or aperture system (as compared to, for example, some types of diffractive or meta-lens systems). The first near distance threshold and the second near distance threshold may correspond to a common near distance threshold for adjusting the depth of field, or may correspond to different near distance thresholds.

The information from the rangefinder (e.g. the rangefinder signals) can in some embodiments be combined with the information from one or more other sensors, such as illumination sensors (e.g. illumination sensor signals, as described below), and the controller can be operable to adjust the depth of field based on the information from the rangefinder and the one or more other sensors (e.g. illumination sensors) to provide the suitable depth of field (e.g. based on the rangefinder signals and the illumination sensor signals).

In examples in which an illumination sensor is provided, the illumination sensor can be operable to detect environmental illumination (e.g. general ambient illumination or illumination of one or more target areas or objects in the environment) and generate illumination sensor signals indicative of the environmental illumination, and the controller 428 can control adjustment of the optical element 413 to vary the depth of field based on at least the illumination sensor signals to provide a suitable depth of field for the ambient illumination. For example, the controller 428 can operate the optical element 413 to provide an extended depth of field when the ambient illumination is greater than a first illumination threshold (e.g. to facilitate near and distance focus in day light conditions), and the controller 428 can operate the optical element 413 to provide a narrower the depth of field (e.g. by reducing or eliminating near focus) when the ambient illumination is less than a second illumination threshold.

In some examples, the controller can operate the optical element 413 to help optimize the depth of field based on the rangefinder signals and the illumination sensor signals. For example, the controller may be configured to help optimize and narrow the depth of field (e.g. by reducing or eliminating near focus) in response to, for example, determining that the distance to an object of interest is greater than a near distance threshold, that the environmental illumination is less than an ambient illumination threshold, and that illumination of a target area in the visual axis of the eye is greater than a target illumination threshold, and may otherwise operate the optical element 413 to provide an extended depth of field (e.g. for providing both near and distance focus). In some examples (e.g. when utilizing certain types of diffractive lens systems), this can help to, for example, reduce visual artifacts (e.g. halos) associated with near vision focus in situations where a user is looking into the distance at an illuminated object in a low ambient light environments (e.g. when seeing headlights, traffic lights, street lamps, etc. at night).

The depth of field for the eye may be varied by, for example, occluding optical portions of the optical element 413, adjusting a morphology of optical portions of the optical element 413, and/or adjusting a refractive index of optical portions of the optical element 413.

For example, in the embodiment shown in FIGS. 13A and 13B, the optical element 413 comprises at least one optical portion 415 and an occlusion mechanism 417 operable by the controller 428 to transition the optical portion 415 between a transparent state (shown in FIG. 13A) in which the optical portion is generally transparent for providing a first depth of field for the eye, and an occluded state (shown in FIG. 13B) in which the optical portion 415 is at least partially occluded relative to the transparent state for providing a second depth of field for the eye, with the second depth of field being different from the first depth of field. In the example illustrated, the second depth of field comprises an extended depth of field relative to the first depth of field. In some examples, transparency of the optical portion 415 is reduced when transitioned from the transparent state to the occluded state (e.g. from a 90% transparency to a 60% transparency), and in some examples, the optical portion is generally transparent in the transparent state, and generally opaque when in the occluded state.

In the example illustrated, the optical portion 415 is arranged concentrically with a visual axis 423 of the device 410, and the occlusion mechanism 417 comprises an adjustable aperture stop 423 operable by the controller to adjust an aperture size 421 for the eye for varying the depth of field. In the example illustrated, the aperture size 421 is reduced when the optical portion 415 is transitioned to the occluded state for extending the depth of field, and aperture size is increased when the optical portions 415 is transitioned to the transparent state to narrow the depth of field. In the example illustrated, the at least one optical element 413 comprises a plurality of optical portions 415a, 415b arranged concentrically, and the occlusion mechanism 417 is configured to reversibly occlude each optical portion 415a, 415b independently for adjusting the aperture size 421. In the example shown in FIG. 13A, both the optical portions 415a, 415b are shown in the transparent state to provide a maximum aperture size. In the example shown in FIG. 13B, the radially outer optical portion 415a is shown in the occluded state and the radially inner optical portion 415b is shown in the transparent state to provide an intermediate aperture size. In the example illustrated, the optical element 413 has an open central optical region 411 inward of the occludable optical portions 415, the central optical region 411 defining a minimum aperture size (which is provided when both optical portions 415a, 415b are in the occluded state).

The occlusion mechanism 417 can operate to transition the at least one optical portion 415 through mechanisms like those described above, such as, for example, electrodeposition (e.g. nanoplating), electrochromism, charged nanoparticles, suspended particles, nanocrystals, etc. For example, the occlusion mechanism 417 can comprise an electrochromic device having a transitionable electrochromic element overlying the optical portion 415. The electrochromic element can be concentric with the axis 423 of the device 410. The electrochromic device can comprise, for example, tungsten trioxide, lithium, reflective metal hydride and/or other suitable electrochromic materials (e.g. electrochromic dyes or electrolytes). Alternatively (or in addition), the occlusion mechanism 417 can comprise an electrodeposition device (e.g. similar to that described above with respect to, for example, the nanoplating embodiments). The electrodeposition device can include one or more working electrodes having a plurality of electrodeposition sites overlying the optical portion 415. The electrodeposition sites can be reversibly platable with ions from an electrolyte medium to occlude the at least one optical portion 415 for providing the second depth of field, and strippable of the ions to unocclude the optical portion 415 for providing the first depth of field.

In some examples, the at least one optical portion 415 can comprise at least one of: (i) one or more diffractive zones, (ii) one or more refractive zones, and (iii) an array of meta-lens wave guide structures (described in more detail below). In some examples, the optical portion 415 can include diffractive zones defined by, for example, a plurality of concentric stepped portions on a surface of a diffractive lens. Alternatively (or in addition) the optical portion 415 can include refractive zones on a refractive lens. The diffractive and/or refractive zones can be configured to provide the eye with a first depth of field when unoccluded, and with a second depth of field when occluded that is different from the first depth of field.

Referring to FIG. 14, in some examples, rather than (or in addition to) being occludable, the at least one optical portion 415 can have an adjustable morphology, and the optical element 413 can include a morphology adjustment mechanism 517 operable by the controller 428 to transition the optical portion 415 between at least a first morphology for providing a first depth of field for the eye and a second morphology for providing a second depth of field for the eye, the second depth of field being different from the first depth of field. In the example illustrated in FIG. 14, the at least one optical portion 415 comprises a lens surface 425 adjustable between the first morphology (shown schematically in dashed lines in FIG. 14) and the second morphology (shown schematically in solid lines in FIG. 14). In the example illustrated, the first morphology corresponds to a spheric shape of the lens surface 425', and the second morphology corresponds to an aspheric shape (relative to the spheric shape) of the lens surface 425.

In such embodiments, the optical portion 415 can be deformable between the first morphology and the second morphology. For example, the optical portion 415 can be formed of a smart material capable of holding the first morphology when at rest, and deformable by the morphology adjustment mechanism 517 toward the second morphology. In some example, the material can be deformable from the first morphology to the second morphology through application of an electrical current via electrodes (shown schematically at 517a, 517b) of the morphology adjustment mechanism 517, and can revert back to the first morphology in absence of the electrical current. In some examples, the material can be deformable from the first morphology to the second morphology through application of a mechanical force, and can have sufficient elasticity to revert back to the first morphology when the mechanical force is relieved. In some examples, the first morphology corresponds to a relaxed state or shape of the optical portion, and the second morphology corresponds to a deformed (e.g. stretched, compressed, bent, etc.) state or shape.

In some examples, the at least one optical portion 415 can comprise one or more diffractive zones adjustable between a first morphology and a second morphology for varying the depth of field. For example, referring to FIGS. 14B and 14C, diffractive zones 432 can comprise portions of (e.g. concentric stepped portions on) a diffractive lens surface 434 when in the first morphology, and the diffractive lens surface 434 can be stretched to provide a relatively smooth lens surface 434' (FIG. 14C) when in the second morphology (e.g. by reducing the stepped portions), which can adjust diffractive properties of the optical portion for varying the depth of field. In some examples, the at least one optical portion 415 can comprise an array of meta-lens wave-guide structures adjustable between the first morphology and the second morphology (described in more detail below).

Referring to FIG. 15, in some examples, rather than (or in addition to) being occludable and/or having an adjustable morphology, the optical portion 415 can have an adjustable refractive index, and the optical element 413 can include a refraction adjustment mechanism 617 operable by the controller 428 to adjust the refractive index for varying the depth of field. In the example illustrated, the at least one optical portion 415 comprises a lens casing 427 having an internal chamber 429 containing nematic liquid crystal (or other suitable material having an adjustable refractive index), and the refraction adjustment mechanism 617 comprises one or more electrodes (shown schematically at 617*a*, 617*b*) adjacent the chamber 429 and operable by the controller 428 to apply an electric field to the nematic liquid crystal for adjusting the refractive index.

The lens casing 427 and the nematic liquid crystal (or other suitable material) can have a common first refractive index corresponding to a first depth of field for the eye in absence of the electric field, and when the electric field is applied, the lens casing 427 has the first refractive index and the nematic liquid crystal transitions to having a second refractive index different from the first refractive index to provide a second depth of field for the eye. In the example illustrated, the lens casing 427 has an exterior lens surface 427*a* having a first lens shape, and an interior lens surface 427*b* defining at least a portion of the internal chamber 429 and having a second lens shape different from the first lens shape. In the example illustrated, the first lens shape is spherical relative to the second lens shape, and the second lens shape is aspherical relative to the first lens shape. When both the lens casing 427 and the nematic liquid crystal have the common first refractive index, the optical portion 415 acts as a spherical lens for providing the first depth of field, and when the nematic liquid crystal is transitioned to have the second refractive index, the internal chamber 429 (and interior lens surface 427*b*) acts as an aspherical lens to provide the second depth of field different from the first depth of field.

Referring to FIG. 16A, in some examples, the at least one optical portion 415 of the optical element 413 can include a dynamically adjustable meta-lens assembly 480 operable to vary the one or more optical properties for the eye (e.g. the depth of field for the eye), and the controller 428 can be configured to control adjustment of the meta-lens assembly 480 for varying the one or more optical properties (e.g. the depth of field).

Referring to FIG. 17, in the example illustrated, the meta-lens assembly 480 includes at least one substrate 481 (shown schematically and not to scale) and at least one array 482 of meta-lens wave-guide structures 484 (shown schematically and not to scale) projecting from a side of the substrate 481. In the example illustrated, the substrate 481 is generally transparent at least in the wave-guide gaps 488 (FIG. 17A) between adjacent wave guide structures 484. The wave-guide structures 484 are shaped and arranged for guiding (e.g. refracting or diffracting) electromagnetic radiation toward at least one focal point of the meta-lens assembly 480. The wave-guide structures 484 can comprise nanostructures, such as, for example, nanopillars and/or nanofins having a suitable arrangement and geometry (e.g. a rectangular or other suitable cross-sectional shape) for guiding electromagnetic radiation toward the at least one focal point. In some examples, the meta-lens assembly 480 can include a wave-guide adjustment mechanism for adjusting properties of the wave-guide structures 484 to vary the one or more optical properties.

In the example illustrated in FIGS. 16A and 16B, the wave-guide adjustment mechanism comprises an occlusion mechanism 417 configured to reversibly occlude at least a portion of the at least one array for varying the one or more optical properties. The occlusion mechanism can be configured to reversibly occlude the at least a portion of the array through at least one of, for example, electrodeposition and/or electrochromism.

In the example illustrated, the at least one array 482 comprises at least one first set of wave-guide structures 482*a* and at least one second set of wave-guide structures 482*b*, and the occlusion mechanism is configured to reversibly occlude at least one of the first set and the second set of wave-guide structures 482*a*, 482*b* while the other one of the first set and the second set of wave-guide structures 482*a*, 482*b* remains unoccluded to vary the one or more optical properties.

In some examples, the at least one first set 482*a* can be configured for near vision focus, and the at least one second set 482*b* can be configured for distance vision focus, and the occlusion mechanism 417 can be operable to reversibly occlude the first set of wave-guide structures 482*a* while the second set 482*b* remains unoccluded to facilitate distance vision focus. In some examples, the occlusion mechanism 417 is operable to reversibly occlude the second set of wave-guide structures 482*b* while the first set 482*a* remains unoccluded. In the example illustrated, each of the first set and the second set of wave-guide structures 482*a*, 482*b* is concentric with a visual axis 423 of the optical portion 415 (and meta-lens assembly 480 in the example illustrated), and the second set 482*b* is radially inward of the first set 482*a*.

In such examples, when the optical portion 415 is in an unoccluded state, the meta-lens assembly 480 is generally bifocal which can provide an extended depth of field for the eye. In some cases, however, when looking at light sources in the distance, such a bifocal arrangement can produce visual artifacts, such as halos, which can interfere with activities in low ambient light (e.g. night-time) conditions, such as, for example driving. In some examples, the occlusion mechanism 417 can be configured to occlude a radially outer portion of the array (e.g. through nanoplating the second set 482*b*) and the radially inner portion can remain unoccluded, so that the meta-lens assembly 480 is focused for distance only, which can help reduce visual artifacts (e.g. halos).

In other examples, the sets of wave-guide structures 484 may be arranged differently. For example, in some embodiments, the array 482 may include a plurality of sets of wave-guide structures interspersed with (or arranged in another manner relative to) each other. Each set can be configured for a specific focal distance for objects at a certain distance. When all sets are active for focusing electromagnetic radiation, the meta-lens assembly 480 can provide an extended depth of field, and the wave-guide adjustment mechanism can be operable to deactivate one or more of the sets of wave-guide structures 484 (e.g. by occluding a corresponding portion or portions of the array via the occlusion mechanism) while the remaining sets remain active to provide a narrowed depth of field.

In some examples in which the depth of field is varied, at least one first set of wave-guide structures can be configured to correspond to a first depth-of-field near limit and first depth-of-field far limit and at least one second set of wave-guide structures can be configured to correspond to a second depth-of-field near limit and a second depth-of-field far limit. The second depth-of-field near and far limits can be greater than the first depth-of-field near and far limits, respectively. When both the first set and second set of wave-guide structures are active (e.g. the portion of the array 482 corresponding to the first and second sets is generally unoccluded), the optical device 410 can provide an extended depth of field for the eye having the first depth-of-field near limit and the second depth-of-field far limit. In some examples it may be useful to provide a narrower depth of field. In such cases, the first set of wave-guide structures can be dynamically deactivated (e.g. the portion of the array 482 corresponding to the first set can be occluded) to provide a narrower depth of field for the eye having the second depth-of-field near limit and the second depth-of-field far limit (which in some examples, may be at infinity).

Referring to FIG. 17A, each wave-guide structure 484 projects from the substrate 481 along a central axis 486 and has a cross-sectional area normal to the axis 486. In the example illustrated, each wave-guide structure 484 has a height 487 along the axis 486 between the substrate 481 and a tip of the wave-guide structure 484. In the example illustrated, the height 487 is shown measured from a first surface of the substrate 481 from which the structure 484 project to the tip of the structure 484. In some examples, the effective height of the structures 484 can be measured from a second surface of the substrate 481 opposite the first surface to the tip of the structure 484. The height 487 can be on the nanoscale, and can be, for example, between 200 nm and 600 nm. Adjacent wave-guide structures 484 are spaced apart by a wave-guide gap 488 through which electromagnetic radiation is guided, and have a center-to-center distance 490 between respective axes 486. In some examples, at least one of the cross-sectional area, the wave-guide gap 488, and the center-to-center distance 490 is adjustable for varying the one or more optical properties.

For example, referring to FIGS. 17B and 17C, the wave-guide adjustment mechanism can comprise electrodeposition sites on the wave-guide structures 484 that are platable with ions from an electrolyte medium to increase a dimension of the wave-guide structures 484, and strippable of the ions to reduce the dimension. The dimension can comprise, for example, the cross-sectional area (FIG. 17B) and/or the height 487 (FIG. 17C). For example, Referring to FIG. 17B, the electrodeposition sites may be formed on sides of the wave-guide structures 484 and platable to increase the effective cross-sectional area, and strippable to reduce the cross-sectional area, thereby adjusting the size of the wave-guide gap 488 between at least some of the adjacent wave-guide structures to vary the one or more optical properties. Referring to FIG. 17C, the electrodeposition sites may be formed on the tip of the wave-guide structures 484 and platable to increase the effective height 487 and strippable to reduce the height 487 to vary the one or more optical properties. In such examples, the sides of the wave-guide structures 484 can be free of electrodeposition sites so that the height 487 can be adjusted via plating without necessarily increasing the cross-sectional area.

Referring to FIG. 17D, in some examples, electrodeposition sites can be provided on the substrate in the wave-guide gaps 488, and the electrodeposition sites can be electroplated to occlude the transparent portion of the substrate 481 in the gaps 488 and reduce (or completely block) transmission of electromagnetic radiation through the wave-guide gaps 488. In some examples, in addition to or instead of electroplating the portion of the substrate 481 in the wave-guide gaps 488, electroplating can be carried out on a side of the substrate 481 opposite the wave-guide structures 484 (and gaps 488) to reduce transmission of electromagnetic radiation through portions of the meta-lens assembly 480. In other examples, portions of the meta-lens assembly 480 can be occluded through other mechanisms such as, for example, electrochromism.

Referring to FIG. 17E, in some examples, the wave-guide adjustment mechanism can comprise a morphology adjustment mechanism (in addition to or in lieu of other adjustment mechanisms) configured to adjust a morphology of the at least one array 482 of meta-lens wave-guide structures 484 for varying the one or more optical properties. In the example illustrated, the morphology adjustment mechanism is operable to adjust the center-to-center distance of at least some of the wave-guide structures for varying the optical properties (e.g. by increasing or decreasing the wave-guide gaps 488 to activate or deactivate portions of the array and/or otherwise adjust the one or more optical properties). In some examples, at least a portion of the substrate 481 is deformable, and the morphology adjustment mechanism 517 is configured to deform the portion of the substrate 481 for adjusting the center-to-center distance between at least some of the wave-guide structures 484 (e.g. by stretching, compressing, and/or bending the substrate material via electrodes and/or mechanical actuators to adjust the center-to-center distance 490, and in turn, the wave-guide gaps 488).

Some of the elements of the devices or methods described in accordance with the teachings herein may be implemented as a combination of hardware or software. For example, the embodiments described herein may be implemented, at least in part, by using one or more computer programs, executing on one or more programmable devices comprising at least one processing element, and at least one data storage element (including volatile and non-volatile memory). It should also be noted that there may be some elements that are used to implement at least part of the embodiments described herein that may be, but not limited to being implemented via software that is written in a high-level procedural language such as object-oriented programming. The program code may be written in C, C++ or any other suitable programming language and may comprise modules or classes, as is known to those skilled in object-oriented programming. Alternatively, or in addition thereto, some of these elements implemented via software may be written in assembly language, machine language or firmware as needed.

At least some of these software programs may be stored on a storage media (e.g., a computer readable medium such as, but not limited to, ROM or RAM) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the devices and methods of the embodiments described herein may be capable of being preinstalled and embedded during manufacture and/or may later be installed as an update for an already deployed device. The medium may be provided in various forms, including non-transitory forms such as, but not limited to, one or more chips or magnetic and electronic storage. In alternative embodiments, the medium may be transitory in nature such as, but not limited to, wire-line transmissions, satellite transmissions, internet transmissions (e.g. downloads), digital and analog signals, and the like. The computer useable instructions may also be in various formats, including compiled and non-compiled code.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments described herein, the general scope of which is defined in the appended claims.

The invention claimed is:

1. An intraocular prosthesis system, comprising:
   a) an intraocular device implantable in an eye, the intraocular device having at least one adjustable optical element operable to vary a depth of field for the eye;
   b) a controller configured to control adjustment of the at least one adjustable optical element for varying the depth of field, wherein the at least one adjustable optical element comprises at least one optical portion having an adjustable morphology, and a morphology adjustment mechanism operable by the controller to transition the at least one optical portion between at least a first morphology for providing a first depth of field for the eye and a second morphology for providing a second depth of field for the eye, the second depth of field different from the first depth of field; and
   c) one or more environment sensors for detecting environmental conditions and generating environment sensor signals indicative of the environmental conditions, and wherein the controller is configured to control adjustment of the optical element based at least on the environment sensor signals to provide a suitable depth of field for the environmental conditions,
   wherein the optical portion is formed of a deformable material configured to hold the first morphology when at rest and deformable by the morphology adjustment mechanism toward the second morphology,
   wherein the morphology adjustment mechanism comprises one or more electrodes coupled to the material, and the material is deformable from the first morphology to the second morphology through application of an electrical current via the electrodes, and
   wherein the first morphology corresponds to an aspheric shape, and the second morphology corresponds to a spheric shape relative to the aspheric shape.

2. The intraocular prosthesis system of claim 1, wherein the at least one optical portion comprises a lens surface adjustable between the first morphology and the second morphology.

3. The intraocular prosthesis system of claim 1, wherein the deformable material reverts back to the first morphology absent the electrical current.

4. The intraocular prosthesis system of claim 1, wherein the environmental conditions comprise a distance to one or more objects of interest.

5. The intraocular prosthesis system of claim 1, wherein the environmental conditions comprise environmental illumination.

6. The intraocular prosthesis system of claim 1, further comprising one or more intraocular sensors for detecting intraocular conditions and generating intraocular sensor signals indicative of the intraocular conditions, and wherein the controller is configured to control adjustment of the optical element based on the intraocular sensor signals to provide a suitable depth of field for the intraocular conditions.

7. An intraocular prosthesis system, comprising:
   a) an intraocular device implantable in an eye, the intraocular device having at least one adjustable optical element operable to vary a depth of field for the eye;
   b) a controller configured to control adjustment of the at least one adjustable optical element for varying the depth of field, wherein the at least one adjustable optical element comprises at least one optical portion having an adjustable morphology, and a morphology adjustment mechanism operable by the controller to transition the at least one optical portion between at least a first morphology for providing a first depth of field for the eye and a second morphology for providing a second depth of field for the eye, the second depth of field different from the first depth of field; and
   c) one or more environment sensors for detecting environmental conditions and generating environment sensor signals indicative of the environmental conditions, and wherein the controller is configured to control adjustment of the optical element based at least on the environment sensor signals to provide a suitable depth of field for the environmental conditions,
   wherein the optical portion is formed of a deformable material configured to hold the first morphology when at rest and deformable by the morphology adjustment mechanism toward the second morphology,
   wherein the morphology adjustment mechanism comprises one or more electrodes coupled to the material, and the material is deformable from the first morphology to the second morphology through application of an electrical current via the electrodes, and
   wherein the at least one optical portion comprises one or more diffractive zones adjustable between the first morphology and the second morphology.

8. The intraocular prosthesis system of claim 7, wherein the diffractive zones comprise portions of a diffractive lens surface.

9. The intraocular prosthesis system of claim 8, wherein the diffractive lens surface is deformable by the morphology adjustment mechanism from the first morphology to the second morphology to smoothen the diffractive lens surface for adjusting diffractive properties of the optical portion to vary the depth of field.

10. The intraocular prosthesis system of claim 7, wherein the deformable material reverts back to the first morphology absent the electrical current.

11. The intraocular prosthesis system of claim 7, wherein the environmental conditions comprise a distance to one or more objects of interest.

12. The intraocular prosthesis system of claim 7, wherein the environmental conditions comprise environmental illumination.

13. The intraocular prosthesis system of claim 7, further comprising one or more intraocular sensors for detecting intraocular conditions and generating intraocular sensor signals indicative of the intraocular conditions, and wherein the controller is configured to control adjustment of the optical element based on the intraocular sensor signals to provide a suitable depth of field for the intraocular conditions.

14. An intraocular prosthesis system, comprising:
   a) an intraocular device implantable in an eye, the intraocular device having at least one adjustable optical element operable to vary a depth of field for the eye;
   b) a controller configured to control adjustment of the at least one adjustable optical element for varying the depth of field, wherein the at least one adjustable optical element comprises at least one optical portion having an adjustable morphology, and a morphology adjustment mechanism operable by the controller to transition the at least one optical portion between at least a first morphology for providing a first depth of field for the eye and a second morphology for providing a second depth of field for the eye, the second depth of field different from the first depth of field; and
   c) one or more intraocular sensors for detecting intraocular conditions and generating intraocular sensor signals indicative of the intraocular conditions, and wherein the controller is configured to control adjustment of the optical element based on the intraocular sensor signals to provide a suitable depth of field for the intraocular conditions, wherein the optical portion is formed of a deformable material configured to hold the first morphology when at rest and deformable by the morphology adjustment mechanism toward the second morphology, wherein the morphology adjustment mechanism comprises one or more electrodes coupled to the material, and the material is deformable from the first morphology to the second morphology through application of an electrical current via the electrodes, and wherein the first morphology corresponds to an aspheric shape, and the second morphology corresponds to a spheric shape relative to the aspheric shape.

15. The intraocular prosthesis system of claim 14, wherein the at least one optical portion comprises a lens surface adjustable between the first morphology and the second morphology.

16. The intraocular prosthesis system of claim 14, wherein the intraocular conditions comprise electrical activity in the eye.

17. An intraocular prosthesis system, comprising:
a) an intraocular device implantable in an eye, the intraocular device having at least one adjustable optical element operable to vary a depth of field for the eye;
b) a controller configured to control adjustment of the at least one adjustable optical element for varying the depth of field, wherein the at least one adjustable optical element comprises at least one optical portion having an adjustable morphology, and a morphology adjustment mechanism operable by the controller to transition the at least one optical portion between at least a first morphology for providing a first depth of field for the eye and a second morphology for providing a second depth of field for the eye, the second depth of field different from the first depth of field; and
c) one or more intraocular sensors for detecting intraocular conditions and generating intraocular sensor signals indicative of the intraocular conditions, and wherein the controller is configured to control adjustment of the optical element based on the intraocular sensor signals to provide a suitable depth of field for the intraocular conditions, wherein the optical portion is formed of a deformable material configured to hold the first morphology when at rest and deformable by the morphology adjustment mechanism toward the second morphology, wherein the morphology adjustment mechanism comprises one or more electrodes coupled to the material, and the material is deformable from the first morphology to the second morphology through application of an electrical current via the electrodes, and wherein the at least one optical portion comprises one or more diffractive zones adjustable between the first morphology and the second morphology.

18. The intraocular prosthesis system of claim 17, wherein the diffractive zones comprise portions of a diffractive lens surface.

19. The intraocular prosthesis system of claim 18, wherein the diffractive lens surface is deformable by the morphology adjustment mechanism from the first morphology to the second morphology to smoothen the diffractive lens surface for adjusting diffractive properties of the optical portion to vary the depth of field.

20. The intraocular prosthesis system of claim 17, wherein the intraocular conditions comprise electrical activity in the eye.

* * * * *